United States Patent
Kim et al.

(10) Patent No.: US 9,653,689 B2
(45) Date of Patent: *May 16, 2017

(54) CONDENSED-CYCLIC COMPOUND AND ORGANIC LIGHT-EMITTING DIODE INCLUDING THE SAME

(71) Applicants: Samsung Display Co., Ltd., Yongin (KR); SFC Co., Ltd., Cheongwon-gun, Chungbuk (KR)

(72) Inventors: Myeong-Suk Kim, Yongin (KR);
Jong-Tae Je, Cheongwon-gun (KR);
Se-Jin Lee, Cheongwon-gun (KR);
Seok-Bae Park, Cheongwon-gun (KR);
Se-Jin Yu, Cheongwon-gun (KR);
Jea-Geon Lim, Cheongwon-gun (KR);
Byoung-Ki Choi, Yongin (KR);
Tae-Kyung Kim, Yongin (KR);
Jeoung-In Yi, Yongin (KR)

(73) Assignees: Samsung Display Co., Ltd., Samsung-ro, Giheung-Gu, Yongin-si, Gyeonggi-Do (KR); SFC CO., LTD., Ochang-Eup, Cheongwon-Gun, Chungbuk (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/969,767

(22) Filed: Dec. 15, 2015

(65) Prior Publication Data

US 2016/0099411 A1 Apr. 7, 2016

Related U.S. Application Data

(63) Continuation-in-part of application No. 13/352,150, filed on Jan. 17, 2012, now Pat. No. 9,238,623.

(30) Foreign Application Priority Data

Jan. 17, 2011 (KR) .................. 10-2011-0004523
Oct. 13, 2011 (KR) .................. 10-2011-0104825

(51) Int. Cl.
H01L 51/50 (2006.01)
H01L 51/00 (2006.01)
(Continued)

(52) U.S. Cl.
CPC .......... *H01L 51/006* (2013.01); *C07B 59/001* (2013.01); *C07C 211/61* (2013.01);
(Continued)

(58) Field of Classification Search
None
See application file for complete search history.

(56) References Cited

U.S. PATENT DOCUMENTS 7,074,801 B1 7/2006 Yoshida et al.
2003/0132703 A1 7/2003 Sakaguchi
(Continued)

FOREIGN PATENT DOCUMENTS

CN 101153036 4/2008
CN 101570536 11/2009
(Continued)

OTHER PUBLICATIONS

Chinese Granted Document issued by SIPO on Dec. 14, 2016 in corresponding Chinese Patent Application No. 201210023181.0 which also claims Korean Patent Application Nos. 10-2011-0004523 and 10-2011-0104825 as its priority applications, together with Request for Entry attached herewith.

*Primary Examiner* — Gregory Clark
(74) *Attorney, Agent, or Firm* — Robert E. Bushnell, Esq.

(57) ABSTRACT

A condensed-cyclic compound represented by Formula 1 below, and an organic light-emitting diode including the condensed-cyclic compound.

(Continued)

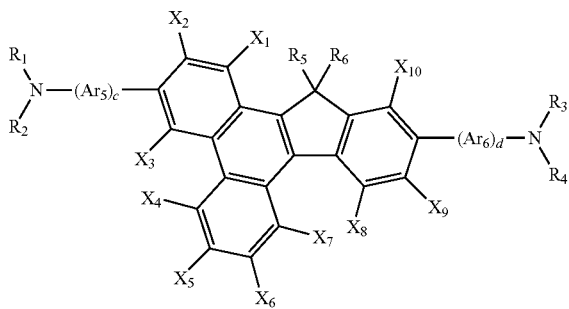

Formula 1 wherein $R_1$ through $R_6$, $Ar_5$ and $Ar_6$, and $X_1$ through $X_{10}$ are defined as in the specification.

16 Claims, 5 Drawing Sheets

(51) Int. Cl.
  *C07C 211/61* (2006.01)
  *C09K 11/06* (2006.01)
  *C09K 11/02* (2006.01)
  *C07F 7/08* (2006.01)
  *C07D 213/74* (2006.01)
  *C07D 487/14* (2006.01)
  *C07C 255/58* (2006.01)
  *C07B 59/00* (2006.01)
  *C07D 209/86* (2006.01)
  *C07D 403/10* (2006.01)

(52) U.S. Cl.
  CPC .......... *C07C 255/58* (2013.01); *C07D 209/86* (2013.01); *C07D 213/74* (2013.01); *C07D 403/10* (2013.01); *C07D 487/14* (2013.01); *C07F 7/0818* (2013.01); *C09K 11/025* (2013.01); *C09K 11/06* (2013.01); *H01L 51/0055* (2013.01); *C07C 2101/14* (2013.01); *C07C 2102/08* (2013.01); *C07C 2102/10* (2013.01); *C07C 2103/52* (2013.01); *C07C 2103/97* (2013.01); *C09K 2211/1007* (2013.01); *C09K 2211/1011* (2013.01); *C09K 2211/1014* (2013.01); *C09K 2211/1022* (2013.01); *C09K 2211/1029* (2013.01); *H01L 51/0052* (2013.01); *H01L 51/0058* (2013.01); *H01L 51/0061* (2013.01); *H01L 51/0067* (2013.01); *H01L 51/0085* (2013.01); *H01L 51/0087* (2013.01); *H01L 51/5012* (2013.01); *H01L 51/5076* (2013.01)

(56) References Cited

U.S. PATENT DOCUMENTS

| | | | |
|---|---|---|---|
| 2007/0072002 | A1 | 3/2007 | Kim et al. |
| 2008/0176099 | A1 | 7/2008 | Hatwar et al. |
| 2009/0108746 | A1 | 4/2009 | Park et al. |
| 2010/0109555 | A1 | 5/2010 | Ichimura et al. |
| 2010/0176377 | A1 | 7/2010 | Fukushima et al. |
| 2011/0031484 | A1 | 2/2011 | Lee et al. |
| 2011/0084256 | A1 | 4/2011 | Kim et al. |

FOREIGN PATENT DOCUMENTS

| | | |
|---|---|---|
| EP | 1860097 A1 | 11/2007 |
| JP | 2006-135146 A | 5/2006 |
| JP | 4164514 B2 | 10/2008 |
| JP | 2009-266927 A | 11/2009 |
| KR | 1020070038110 A | 4/2007 |
| KR | 1020080003413 A | 1/2008 |
| KR | 1020080015865 A | 2/2008 |
| KR | 1020080109000 A | 12/2008 |
| KR | 1020100012808 A | 2/2010 |
| KR | 10-2010-0112903 A | 10/2010 |

CONDENSED-CYCLIC COMPOUND AND ORGANIC LIGHT-EMITTING DIODE INCLUDING THE SAME

CLAIM OF PRIORITY

This application is a continuation in part under 35 U.S.C. §120 of U.S. application Ser. No. 13/352,150, filed on Jan. 17, 2012 which is herein incorporated by reference. This application also makes reference to, incorporates the same herein, and claims all benefits accruing under 35 U.S.C. §119 from applications for CONDENSED-CYCLIC COMPOUND AND ORGANIC LIGHT-EMITTING DIODE INCLUDING THE SAME earlier filed in the Korean Intellectual Property Office on 17 Jan. 2011 and 13 Oct. 2011 and there duly assigned Serial Nos. 10-2011-0004523 and 10-2011-0104825, respectively.

BACKGROUND OF THE INVENTION

Field of the Invention

The present invention relates to a condensed-cyclic compound represented by Formula 1 and an organic light-emitting diode including the same.

Description of the Related Art

Organic light-emitting diodes (OLEDs), which are self-emitting devices, have advantages such as a wide viewing angle, excellent contrast, quick response, high brightness, and excellent driving voltage. The OLEDs can provide multicolored images.

A general OLED has a structure including a substrate, an anode, a hole transport layer (HTL), an emission layer (EML), an electron transport layer (ETL), and a cathode which are sequentially stacked on the substrate. In this regard, the HTL, the EML, and the ETL are organic layers formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY OF THE INVENTION

The present invention provides a condensed-cyclic compound having a novel structure.

The present invention also provides an organic light-emitting diode including the above condensed-cyclic compound.

According to an aspect of the present invention, there is provided a condensed-cyclic compound represented by Formula 1 below:

Formula 1

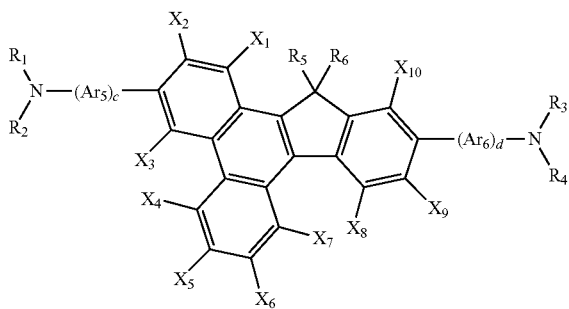

wherein $R_1$ may be represented by $-(Ar_1)_{a1}-(R_{11})_{b1}$, $R_2$ may be represented by $-(Ar_2)_{a2}-(R_{12})_{b2}$, $R_3$ may be represented by $-(Ar_3)_{a3}-(R_{13})_{b3}$, and $R_4$ may be represented by $-(Ar_4)_{a4}-(R_{14})_{b4}$; $Ar_1$ through $Ar_4$ may be each independently a substituted or unsubstituted $C_6$-$C_{60}$ aromatic linking group or a substituted or unsubstituted $C_2$-$C_{60}$ heteroaromatic linking group; $Ar_y$ and $Ar_6$ may be each independently a substituted or unsubstituted $C_6$-$C_{60}$ arylene group or a substituted or unsubstituted $C_2$-$C_{60}$ heteroarylene group; $R_5$, $R_6$, and $R_{11}$ through $R_{14}$ may be each independently non-covalent electron pairs, hydrogen, deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, or a substituted or unsubstituted $C_2$-$C_{60}$ condensed-cyclic group; $a_1$ through $a_4$ may be each independently an integer of 0 to 3; $b_1$ through $b_4$ may be each independently an integer of 1 to 5; c and d may be each independently an integer of 0 to 3; $X_1$ through $X_{10}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, $-Si(R_{21})(R_{22})(R_{23})$, or $-N(R_{24})(R_{25})$; and $R_{21}$ through $R_{25}$ may be each independently hydrogen, deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group.

In some embodiments of the present invention, $R_{11}$ through $R_{14}$ in Formula 1 may be each independently hydrogen, deuterium, a substituted or unsubstituted $C_1$-$C_{10}$ alkyl group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted cyclopentyl group, a substituted or unsubstituted cyclohexyl group, a substituted or unsubstituted cycloheptyl group, a substituted or unsubstituted dihydronaphthyl group, a substituted or unsubstituted tetrahydronaphthyl group, or a substituted or unsubstituted dihydro-indenyl group.

In some embodiments of the present invention, $Ar_1$ through $Ar_4$ in Formula 1 may be each independently a substituted or unsubstituted benzene linking group, a substituted or unsubstituted pentalene linking group, a substituted or unsubstituted indene linking group, a substituted or unsubstituted naphthalene linking group, a substituted or unsubstituted azulene linking group, a substituted or unsubstituted heptalene linking group, a substituted or unsubstituted indacene linking group, a substituted or unsubstituted acenaphthylene linking group, a substituted or unsubstituted fluorene linking group, a substituted or unsubstituted phenalene linking group, a substituted or unsubstituted phenanthrene linking group, a substituted or unsubstituted anthracene linking group, a substituted or unsubstituted fluoranthene linking group, a substituted or unsubstituted triphenylene linking group, a substituted or unsubstituted pyrene linking group, a substituted or unsubstituted crycene linking group, a substituted or unsubstituted naphthacene linking group, a substituted or unsubstituted pycene linking group, a substituted or unsubstituted perylene linking group, a substituted or unsubstituted pentacene linking group, or a substituted or unsubstituted hexacene linking group.

In some embodiments of the present invention, $a_1$ through $a_4$ in Formula 1 may be each independently 0, 1, or 2, and $b_1$ through $b_4$ may be each independently 1 or 2.

In some embodiments of the present invention, $R_{11}$ through $R_{14}$ in Formula 1 may be each independently one of hydrogen; deuterium; a $C_1$-$C_{10}$ alkyl group; a phenyl group; a naphthyl group; a phenanthrenyl group; a fluorenyl group; a pyrenyl group; a cyclopentyl group; a cyclohexyl group; a tetrahydronaphthyl group; a dihydro-indenyl group; and a phenyl group, a naphthyl group, a phenanthrenyl group, a fluorenyl group, a pyrenyl group, a cyclopentyl group, a cyclohexyl group, a tetrahydronaphthyl group, and a dihydro-indenyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, and —Si($Q_1$)($Q_2$)($Q_3$); $Q_1$ through $Q_3$ may be each independently a $C_1$-$C_{10}$ alkyl group or a $C_6$-$C_{14}$ aryl group; $Ar_1$ through $Ar_4$ may be each independently represented by one of Formulae 3A through 3G below.

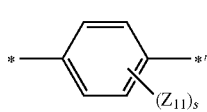

Formula 3A

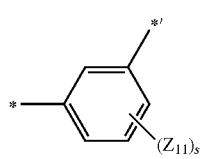

Formula 3B

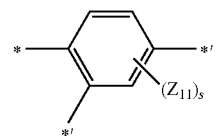

Formula 3C

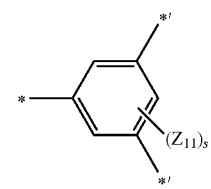

Formula 3D

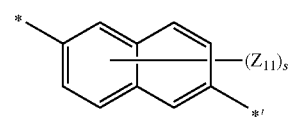

Formula 3E

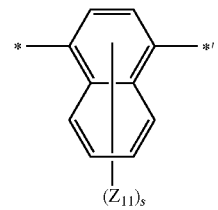

Formula 3F

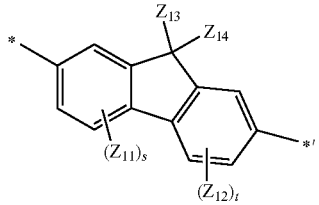

Formula 3G

Wherein $Z_{11}$ through $Z_{14}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group; s may be an integer of 1 to 6; and t may be an integer of 1 to 3.

In some embodiments of the present invention, $R_5$ and $R_6$ in Formula 1 may be each independently hydrogen, deuterium, a substituted or unsubstituted $C_1$-$C_{10}$ alkyl group, or a substituted or unsubstituted $C_6$-$C_{20}$ aryl group.

In some embodiments of the present invention, $R_5$ and $R_6$ in Formula 1 may be each independently one of hydrogen; deuterium; a $C_1$-$C_{10}$ alkyl group; a phenyl group; a naphthyl group; and a phenyl group and a naphthyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group.

In some embodiments of the present invention, $R_5$ and $R_6$ in Formula 1 may be linked to each other via a single bond, a linking group represented by Formula 4A below, or a linking group represented by Formula 4B below.

Formula 4A

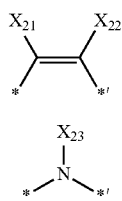

Formula 4B

Wherein $X_{21}$ through $X_{23}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group.

In some embodiments of the present invention, the condensed-cyclic compound of Formula 1 may include one of the compounds represented by Formulae 1A through 1D below:

Formula 1A

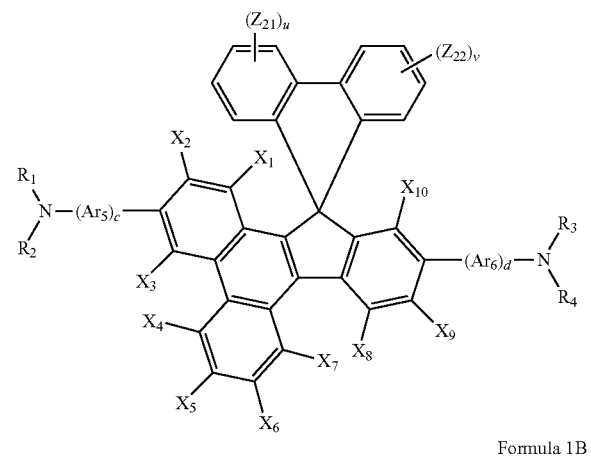

Formula 1B

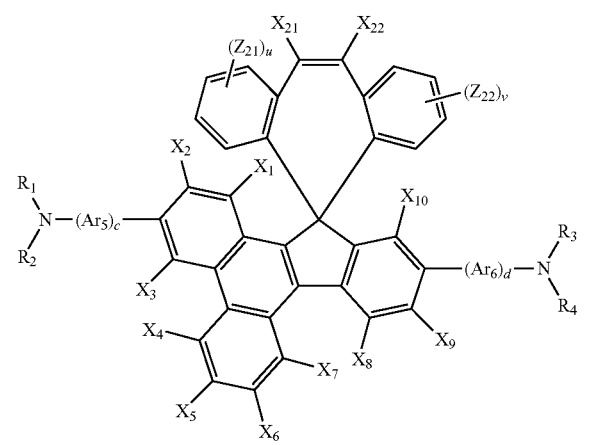

Formula 1C

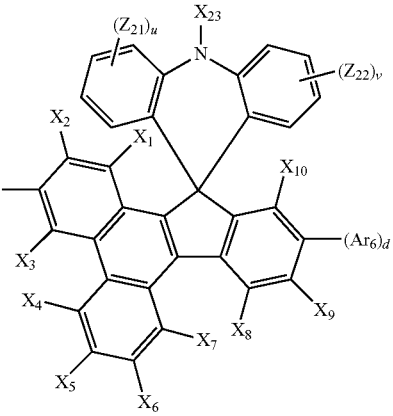

Formula 1D

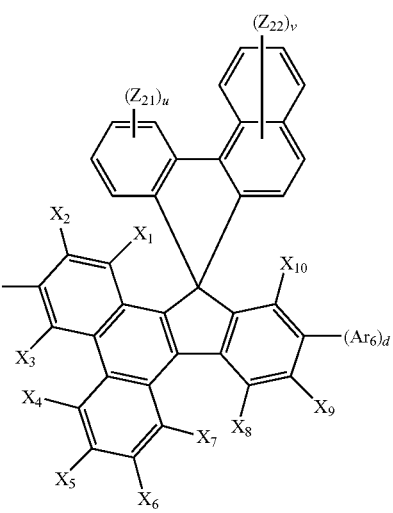

wherein $R_1$ through $R_4$, $Ar_5$, $Ar_6$, c, d, $X_1$ through $X_{10}$, and $X_{21}$ through $X_{23}$ are the same as defined above.

$Z_{21}$ and $Z_{22}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, or a substituted or unsubstituted $C_1$-$C_{60}$ alkoxy group; u may be an integer of 1 to 4; and v may be an integer of 1 to 6.

In some embodiments of the present invention, at least one of a combination of $R_1$ and $R_2$ and a combination of $R_3$ and $R_4$ in Formula 1 may be linked to each other.

In some embodiments of the present invention, at least one of —N($R_1$)($R_2$) and —N($R_3$)($R_4$) in Formula 1 may be represented by one of Formulae 5A through 5F below.

Formula 5A

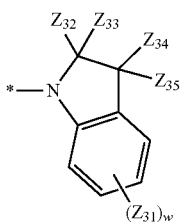

Formula 5B
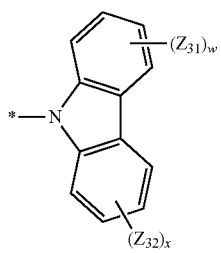

Formula 5C
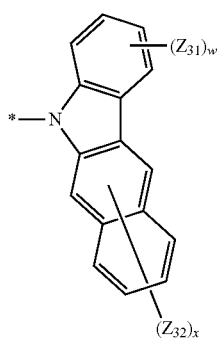

Formula 5D
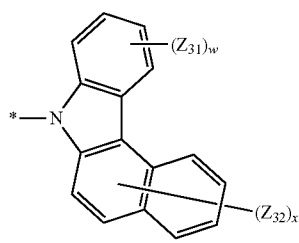

Formula 5E
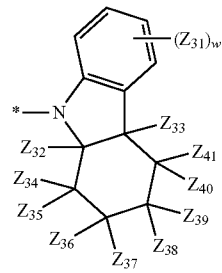

Formula 5F
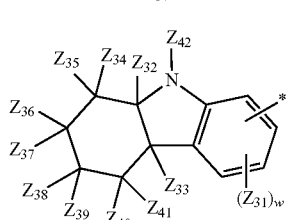

Wherein $Z_{31}$ through $Z_{42}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, or a substituted or unsubstituted $C_1$-$C_{60}$ alkoxy group, or a substituted or unsubstituted $C_6$-$C_{60}$ aryl group; and w and x may be each independently an integer of 1 to 8.

In some embodiments of the present invention, the condensed-cyclic compound may be one of Compounds 1, 3, 9, 10, 11, 12, 14, 17, 22, 26, 28, 29, 54, 64, and 68:

Compound 1
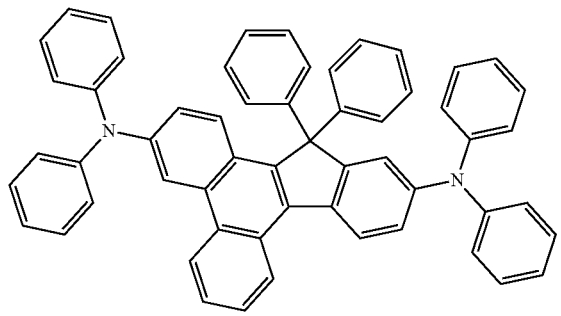

Compound 3
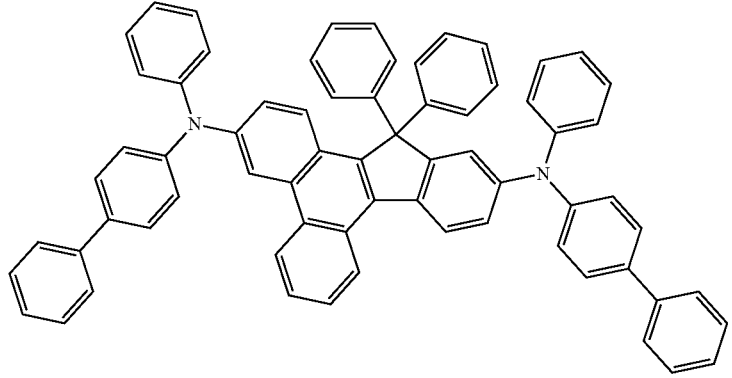

-continued
Compound 9
Compound 10
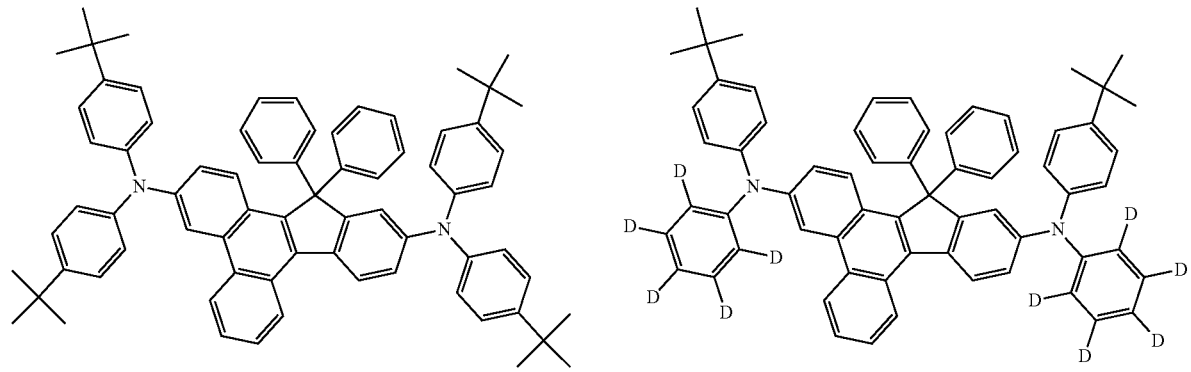
Compound 11
Compound 12
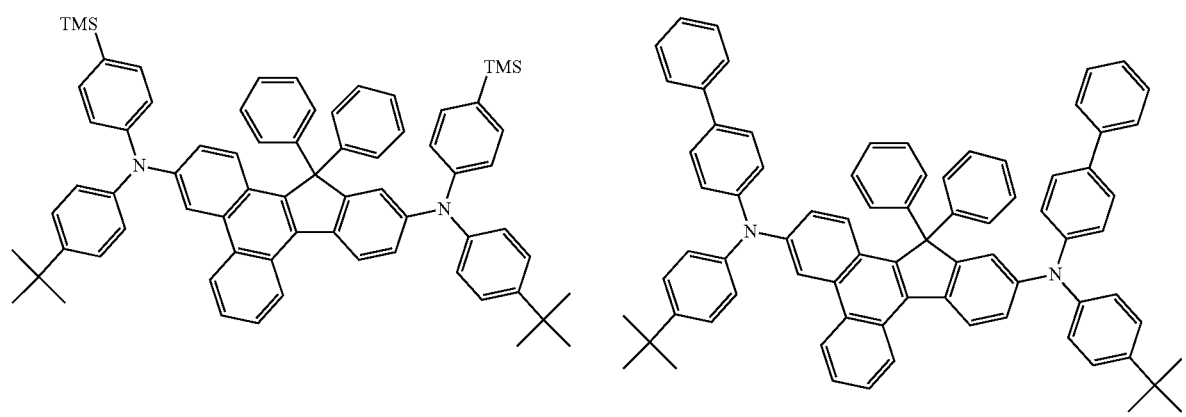
Compound 14
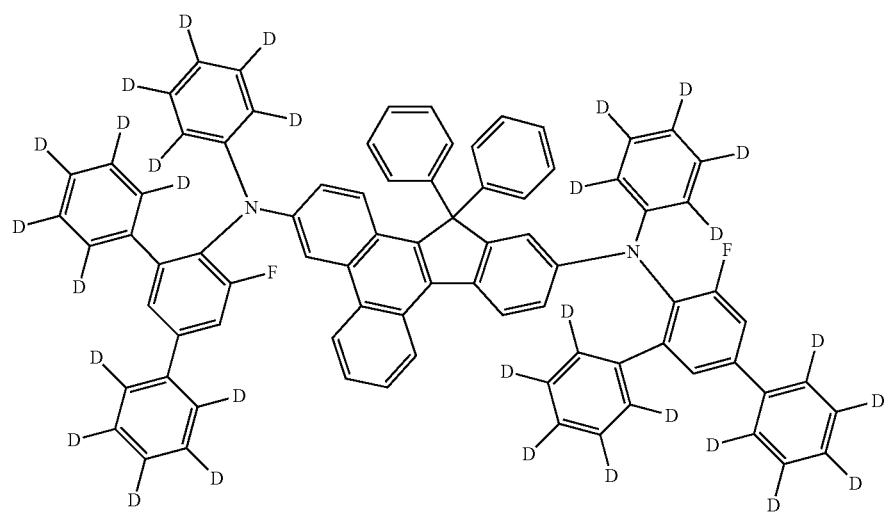

-continued
Compound 17
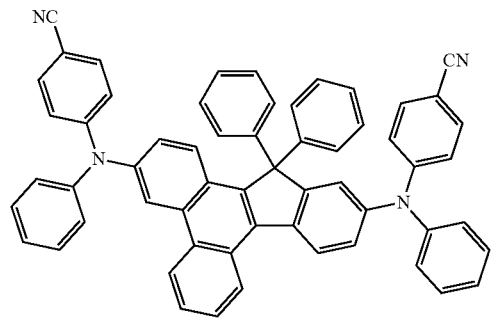
Compound 22
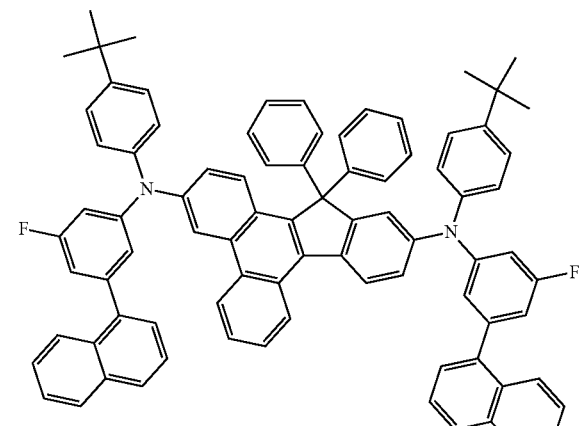
Compound 26
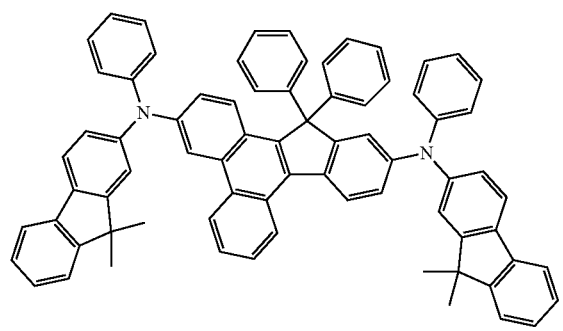
Compound 28
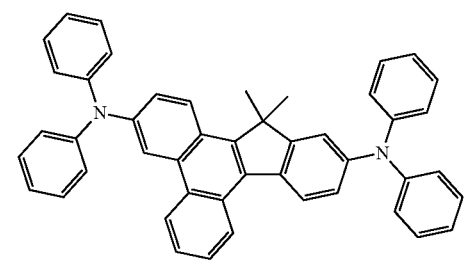
Compound 29
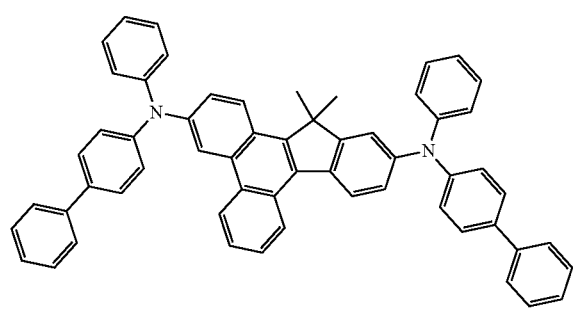
Compound 54
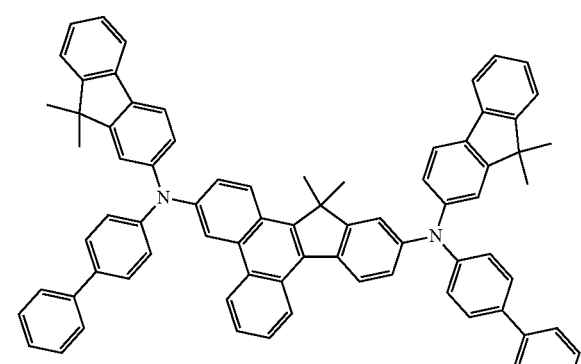
Compound 64
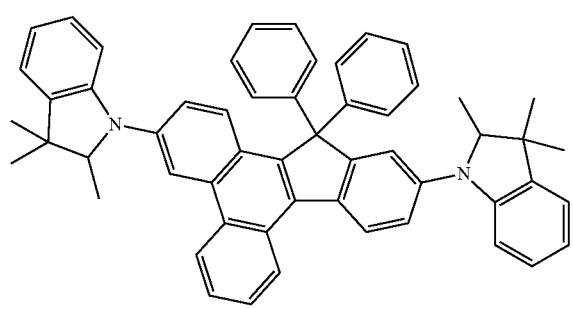

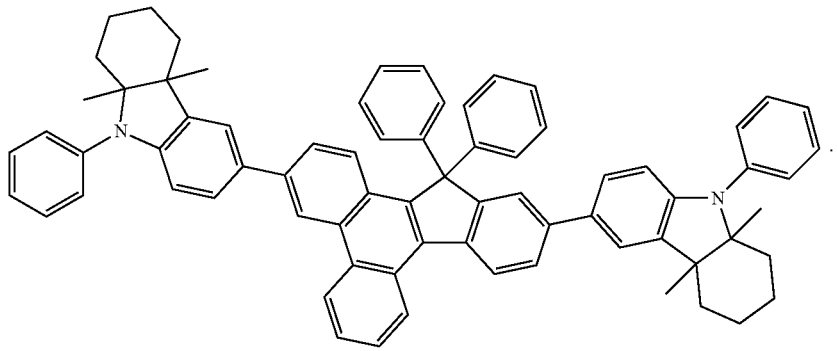

Compound 68

According to another aspect of the present invention, there is provided an organic light-emitting diode including a first electrode; a second electrode facing the first electrode; and an organic layer interposed between the first electrode and the second electrode, wherein the organic layer includes at least one of the condensed-cyclic compounds of Formula 1.

In some embodiments of the present invention, the organic layer may include at least one of a hole injection layer, a hole transport layer, a functional layer having hole injection and hole transport abilities, an emission layer, an electron transport layer, and an electron injection layer In some embodiments of the present invention, the emission layer may include the condensed-cyclic compound.

In some embodiments of the present invention, the emission layer may include a host and the condensed-cyclic compound in the emission layer acts as a dopant.

In some embodiments of the present invention, the host may include an anthracene-based compound represented by Formula 60 below.

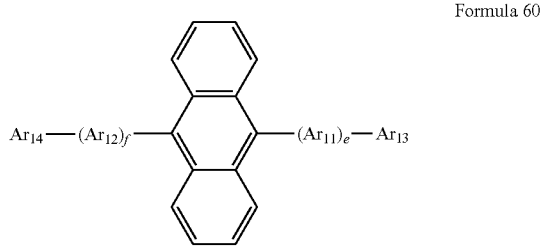

Formula 60

Wherein $Ar_{11}$ and $Ar_{12}$ may be each independently a substituted or unsubstituted $C_6$-$C_{60}$ arylene group; $Ar_{13}$ and $Ar_{14}$ may be each independently a substituted or unsubstituted $C_1$-$C_{10}$ alkyl group or a substituted or unsubstituted $C_6$-$C_{60}$ aryl group; and e and f may be each independently an integer of 0 to 5.

In some embodiments of the present invention, the electron transport layer may include an electron transport organic compound and a metal-containing material.

In some embodiments of the present invention, the metal-containing material may be a lithium complex.

In some embodiments of the present invention, the organic layer may include at least one of a hole injection layer, a hole transport layer, and a functional layer having hole injection and hole transport abilities, and at least one of the hole injection layer, the hole transport layer, and the functional layer having hole injection and hole transport abilities comprises a charge-generating material.

BRIEF DESCRIPTION OF THE DRAWINGS

A more complete appreciation of the present invention, and many of the attendant advantages thereof, will be readily apparent as the present invention becomes better understood by reference to the following detailed description when considered in conjunction with the accompanying drawings in which like reference symbols indicate the same or similar components, wherein.

DETAILED DESCRIPTION OF THE INVENTION

Figure 1:
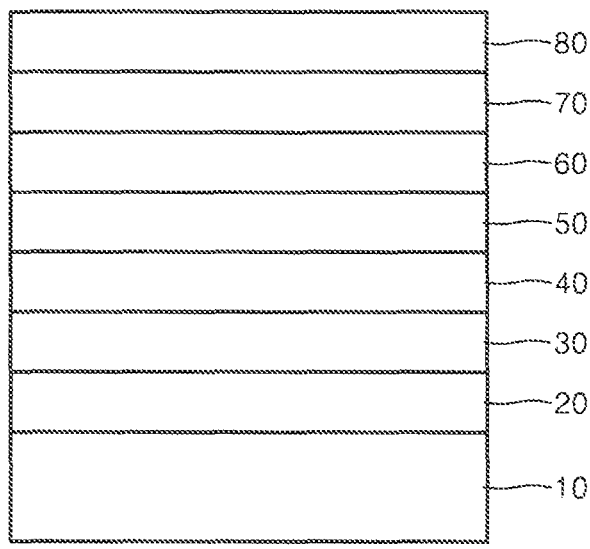
FIG. 1 is a schematic structure of an organic light-emitting diode (OLED) according to an embodiment of the present invention.

Hereinafter, the present invention will be described more fully with reference to the accompanying drawings, in which exemplary embodiments of the present invention are shown.

As used herein, the term "and/or" includes any and all combinations of one or more of the associated listed items. Expressions such as "at least one of" when preceding a list of elements, modify the entire list of elements and do not modify the individual elements of the list.

According to an embodiment of the present invention, there is provided a condensed-cyclic compound represented by Formula 1 below:

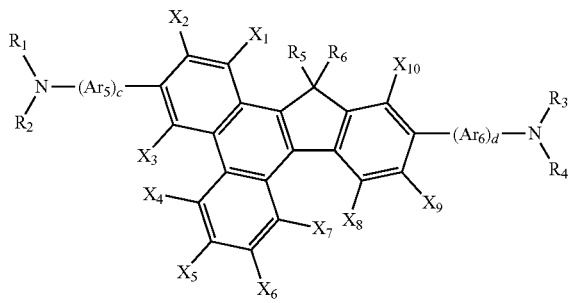

Formula 1

Wherein $R_1$ may be represented by $-(Ar_1)_{a1}-(R_{11})_{b1}$, $R_2$ may be represented by $-(Ar_2)_{a2}-(R_{12})_{b2}$, $R_3$ may be represented by $-(Ar_3)_{a3}-(R_{13})_{b3}$, and $R_4$ may be represented by $-(Ar_4)_{a4}-(R_{14})_{b4}$; $R_5$ and $R_6$ may be each independently non-covalent electron pairs, hydrogen, deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, or a substituted or unsubstituted $C_2$-$C_{60}$ condensed-cyclic group.

In Formula 1, $R_{11}$ through $R_{14}$ may be each independently non-covalent electron pairs, hydrogen, deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, or a substituted or unsubstituted $C_2$-$C_{60}$ condensed-cyclic group.

For example, $R_{11}$ through $R_{14}$ may be each independently hydrogen, deuterium, a substituted or unsubstituted $C_1$-$C_{10}$ alkyl group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted cyclopentyl group, a substituted or unsubstituted cyclohexyl group, a substituted or unsubstituted cycloheptyl group, a substituted or unsubstituted dihydronaphthyl group, a substituted or unsubstituted tetrahydronaphthyl group, or a substituted or unsubstituted dihydro-indenyl group, but are not limited thereto.

$R_{11}$ through $R_{14}$ may be each independently one of hydrogen; deuterium; a $C_1$-$C_{10}$ alkyl group; a phenyl group; a naphthyl group; a phenanthrenyl group; a fluorenyl group; a pyrenyl group; a cyclopentyl group; a cyclohexyl group; a tetrahydronaphthyl group; a dihydro-indenyl group; and a phenyl group, a naphthyl group, a phenanthrenyl group, a fluorenyl group, a pyrenyl group, a cyclopentyl group, a cyclohexyl group, a tetrahydronaphthyl group, and a dihydro-indenyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, and $-Si(Q_1)(Q_2)(Q_3)$; $Q_1$ through $Q_3$ are each independently a $C_1$-$C_{10}$ alkyl group or a $C_6$-$C_{14}$ aryl group.

For example, $R_{11}$ through $R_{14}$ may be each independently hydrogen, deuterium, or a group represented by one of Formulae 2A through 2K below, but are not limited thereto:

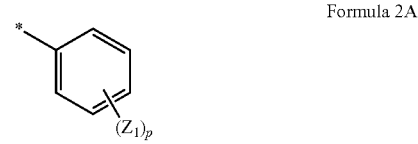

Formula 2A

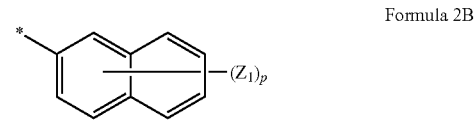

Formula 2B

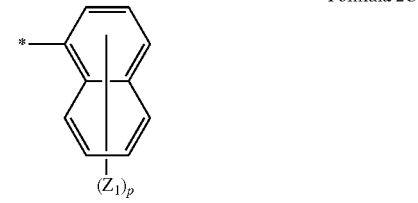

Formula 2C

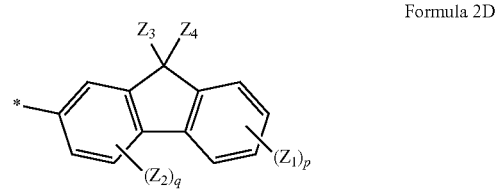

Formula 2D

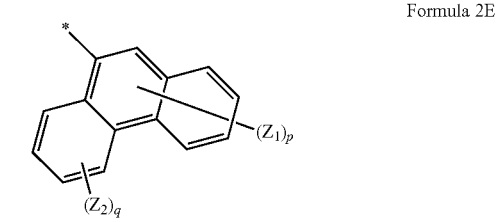

Formula 2E

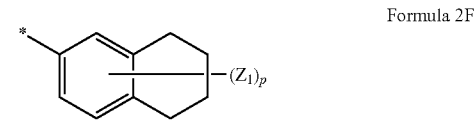

Formula 2F

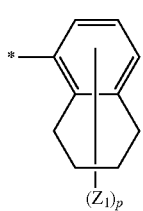
Formula 2G

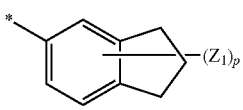
Formula 2H

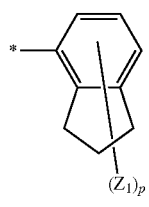
Formula 2I

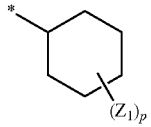
Formula 2J

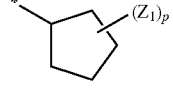
Formula 2K

In Formulae 2A through 2K, $Z_1$ through $Z_4$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group (e.g., a $C_1$-$C_{10}$ alkyl group), a $C_2$-$C_{60}$ alkenyl group (e.g., $C_2$-$C_{10}$ alkenyl group), a $C_2$-$C_{60}$ alkynyl group (e.g., a $C_2$-$C_{10}$ alkynyl group), a $C_1$-$C_{60}$ alkoxy group (e.g., a $C_1$-$C_{10}$ alkoxy group), or —Si($Q_1$)($Q_2$)($Q_3$); p is an integer of 1 to 11; and q is an integer of 1 to 4. In this regard, $Q_1$ through $Q_3$ may be each independently a $C_1$-$C_{10}$ alkyl group or a $C_6$-$C_{14}$ aryl group.

For example, in Formulae 2A through 2K, $Z_1$ through $Z_4$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a methyl group, an ethyl group, a propyl group, a butyl group, a pentyl group, a methoxy group, an ethoxy group, a propoxy group, a butoxy group, a pentoxy group, or —Si($Q_1$)($Q_2$)($Q_3$) where $Q_1$ through $Q_3$ may be each independently a $C_1$-$C_{10}$ alkyl group (e.g., a methyl group, an ethyl group, a propyl group, a butyl group, a pentyl group, and the like).

In Formulae 2A through 2K, * denotes a binding site with "N" of Formula 1 when each of a1 through a4 is 0 and denotes a binding site with each of $Ar_1$ through $Ar_4$ when each of a1 through a4 is not 0.

In Formula 1, $Ar_1$ through $Ar_4$ may be each independently a substituted or unsubstituted $C_6$-$C_{60}$ aromatic linking group or a substituted or unsubstituted $C_2$-$C_{60}$ heteroaromatic linking group. $Ar_1$ through $Ar_4$ may be each independently a divalent linking group (refer to Formula 3A below), a trivalent linking group (refer to Formula 3C below), a tetravalent linking group, or a pentavalent group according to the number of each of $R_{11}$ groups to $R_{14}$ groups that are respectively linked to $Ar_1$ through $Ar_4$, and this may be easily understood with reference to Compounds 1 through 78 below, which are condensed-cyclic compounds.

In Formula 1, $Ar_1$ through $Ar_4$ may be each independently a substituted or unsubstituted benzene linking group, a substituted or unsubstituted pentalene linking group, a substituted or unsubstituted indene linking group, a substituted or unsubstituted naphthalene linking group, a substituted or unsubstituted azulene linking group, a substituted or unsubstituted heptalene linking group, a substituted or unsubstituted indacene linking group, a substituted or unsubstituted acenaphthylene linking group, a substituted or unsubstituted fluorene linking group, a substituted or unsubstituted phenalene linking group, a substituted or unsubstituted phenanthrene linking group, a substituted or unsubstituted anthracene linking group, a substituted or unsubstituted fluoranthene linking group, a substituted or unsubstituted triphenylene linking group, a substituted or unsubstituted pyrene linking group, a substituted or unsubstituted crycene linking group, a substituted or unsubstituted naphthacene linking group, a substituted or unsubstituted pycene linking group, a substituted or unsubstituted perylene linking group, a substituted or unsubstituted pentacene linking group, or a substituted or unsubstituted hexacene linking group.

For example, $Ar_1$ through $Ar_4$ may be each independently represented by one of Formulae 3A through 3G below:

Formula 3A

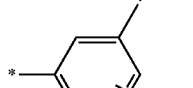
Formula 3B

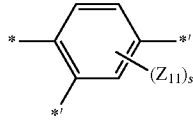
Formula 3C

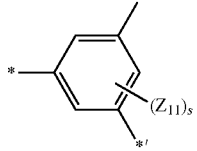
Formula 3D

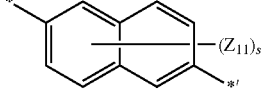
Formula 3E

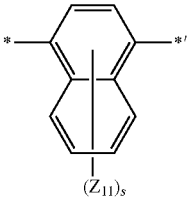
Formula 3F

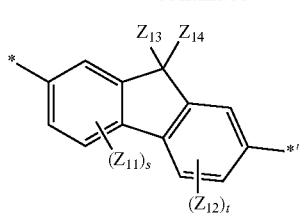

Formula 3G

In Formulae 3A through 3G, $Z_{11}$ through $Z_{14}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group (e.g., a $C_1$-$C_{10}$ alkyl group), a $C_2$-$C_{60}$ alkenyl group (e.g., $C_2$-$C_{10}$ alkenyl group), a $C_2$-$C_{60}$ alkynyl group (e.g., a $C_2$-$C_{10}$ alkynyl group), or a $C_1$-$C_{60}$ alkoxy group (e.g., a $C_1$-$C_{10}$ alkoxy group); s is an integer of 1 to 6; and t is an integer of 1 to 3.

For example, in Formulae 3A through 3G, $Z_{11}$ through $Z_{14}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a methyl group, an ethyl group, a propyl group, a butyl group, a pentyl group, a methoxy group, an ethoxy group, a propoxy group, a butoxy group, or a pentoxy group, but are not limited thereto.

In Formulae 3A through 3G, * denotes a binding site with "N" of Formula 1 and *' denotes a binding site with each of $R_{11}$ through $R_{14}$.

In Formula 1, $a_1$ through $a_4$ may be each independently an integer of 0 to 3 and $b_1$ through $b_4$ may be each independently an integer of 1 to 5. For example, $a_1$ through $a_4$ may be each independently an integer of 0, 1, or 2 and $b_1$ through $b_4$ may be each independently an integer of 1 or 2, but they are not limited thereto. If $a_1$ is 2 or more, two or more $Ar_1$ groups may be identical to or different from each other. If $a_2$ is 2 or more, two or more $Ar_2$ groups may be identical to or different from each other. If $a_3$ is 2 or more, two or more $Ar_3$ groups may be identical to or different from each other. If $a_4$ is 2 or more, two or more $Ar_4$ groups may be identical to or different from each other. If $b_1$ is 2 or more, two or more $R_{11}$ groups may be identical to or different from each other. If $b_2$ is 2 or more, two or more $R_{12}$ groups may be identical to or different from each other. If $b_3$ is 2 or more, two or more $R_{13}$ groups may be identical to or different from each other. If $b_4$ is 2 or more, two or more $R_{14}$ groups may be identical to or different from each other.

With reference to the description above, in Formula 1, $R_1$ through $R_4$ may be selected. For example, $R_1$ through $R_4$ may be each independently selected such that $R_{11}$ through $R_{14}$ are each independently one selected from hydrogen; deuterium; a $C_1$-$C_{10}$ alkyl group; a phenyl group; a naphthyl group; a phenanthrenyl group; a fluorenyl group; a pyrenyl group; a cyclopentyl group; a cyclohexyl group; a tetrahydronaphthyl group; a dihydro-indenyl group; and a phenyl group, a naphthyl group, a phenanthrenyl group, a fluorenyl group, a pyrenyl group, a cyclopentyl group, a cyclohexyl group, a tetrahydronaphthyl group, and a dihydro-indenyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, and —Si($Q_1$)($Q_2$)($Q_3$) where $Q_1$ through $Q_3$ are each independently a $C_1$-$C_{10}$ alkyl group or a $C_6$-$C_{14}$ aryl group; and $Ar_1$ through $Ar_4$ are each independently represented by one of Formulae 3A through 3G.

Alternatively, $R_1$ through $R_4$ may be each independently selected such that $R_{11}$ through $R_{14}$ are each independently hydrogen or deuterium, or represented by one of Formulae 2A through 2K, and $Ar_1$ through $Ar_4$ are each independently represented by one of Formulae 3A through 3G, but are not limited thereto.

In Formula 1, $R_1$ through $R_4$ may be identical to or different from each other.

In Formula 1, $Ar_5$ and $Ar_6$ may be each independently a substituted or unsubstituted $C_6$-$C_{60}$ arylene group, or a substituted or unsubstituted $C_2$-$C_{60}$ heteroarylene group.

For example, $Ar_5$ and $Ar_6$ may be each independently a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted pycenylene group, a substituted or unsubstituted perylenylene group, a substituted or unsubstituted pentacenylene group, or a substituted or unsubstituted hexacenylene group.

For example, $R_5$ and $R_6$ are each independently hydrogen, deuterium, a substituted or unsubstituted $C_1$-$C_{10}$ alkyl group, or a substituted or unsubstituted $C_6$-$C_{20}$ aryl group.

For example, $R_5$ and $R_6$ may be each independently one of hydrogen; deuterium; a $C_1$-$C_{10}$ alkyl group; a phenyl group; a naphthyl group; and a phenyl group and a naphthyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group (e.g., methyl, ethyl, propyl, butyl, pentyl, and the like), a $C_2$-$C_{60}$ alkenyl group, a $C_2$-$C_{60}$ alkynyl group, and a $C_1$-$C_{60}$ alkoxy group (e.g., methoxy, ethoxy, propoxy, butoxy, pentoxy, and the like), but are not limited thereto.

In Formula 1, c and d may be each independently an integer of 0 to 3. For example, c and d may be each independently an integer of 0 or 1, but are not limited thereto.

In Formula 1, $R_5$ and $R_6$ may be linked to each other via a single bond, a linking group represented by Formula 4A below, or a linking group represented by Formula 4B below:

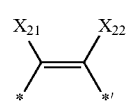

Formula 4A

Formula 4B

Wherein $X_{21}$ through $X_{23}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group.

For example, in Formulae 4A and 4B, $X_{21}$ through $X_{23}$ may be each independently one of hydrogen; deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group; a phenyl group; a naphthyl group; and a phenyl group and a naphthyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group (e.g., methyl, ethyl, propyl, butyl, pentyl, and the like), a $C_2$-$C_{60}$ alkenyl group, a $C_2$-$C_{60}$ alkynyl group, and a $C_1$-$C_{60}$ alkoxy group (e.g., methoxy, ethoxy, propoxy, butoxy, pentoxy, and the like), but are not limited thereto.

When $R_5$ and $R_6$ of Formula 1 are linked to each other via a single bond, a linking group of Formula 4A, or a linking group of Formula 4B as described above, the condensed-cyclic compound may be represented by one of Formulae 1A through 1D (in Formula 1, each of $R_5$ and $R_6$ is independently a substituted or unsubstituted phenyl group):

Formula 1A

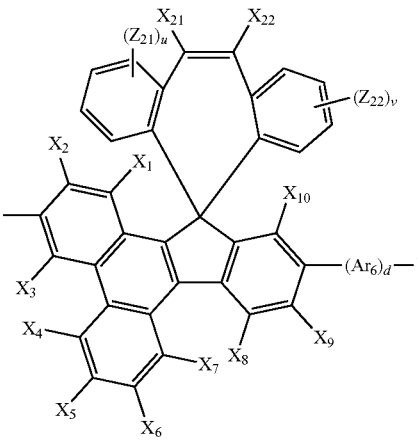

Formula 1B

Formula 1C

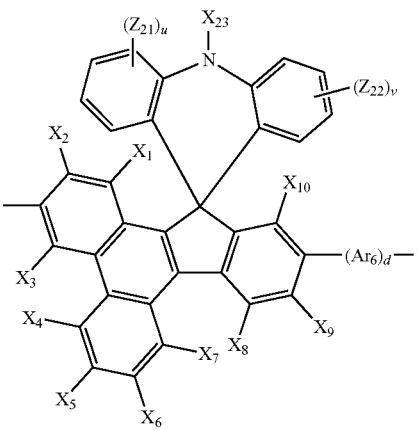

Formula 1D

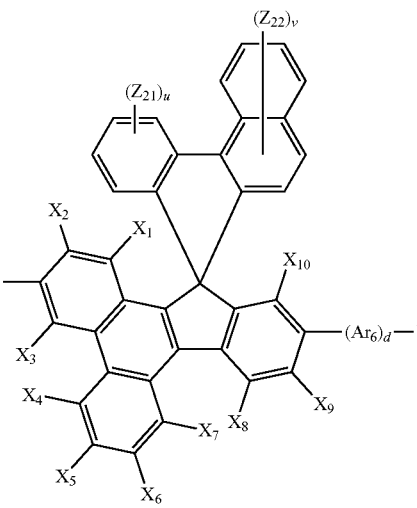

Wherein $R_1$ through $R_4$, $Ar_5$, $Ar_6$, c, d, $X_1$ through $X_{10}$, and $X_{21}$ through $X_{23}$ are the same as defined above; $Z_{21}$ and $Z_{22}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, or a substituted or unsubstituted $C_1$-$C_{60}$ alkoxy group; u may be an integer of 1 to 4; and v may be an integer of 1 to 6.

For example, in Formulae 1A through 1D, $Z_{21}$ and $Z_{22}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a methyl group, an ethyl group, a propyl group, a butyl group, a pentyl group, a methoxy group, an ethoxy group, a propoxy group, a butoxy group, or a pentoxy group, but are not limited thereto.

In Formula 1, at least one of a combination of $R_1$ and $R_2$ and a combination of $R_3$ and $R_4$ may be linked to each other. For example, in Formula 1, at least one of —$N(R_1)(R_2)$ and —$N(R_3)(R_4)$ may be represented by one of Formulae 5A through 5F below, but are not limited thereto:

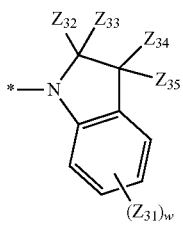

Formula 5A

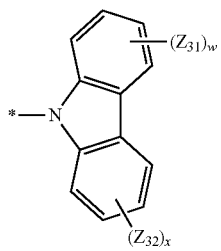

Formula 5B

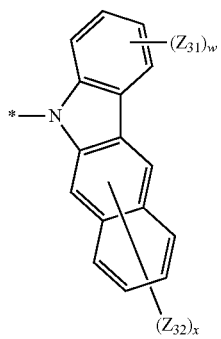

Formula 5C

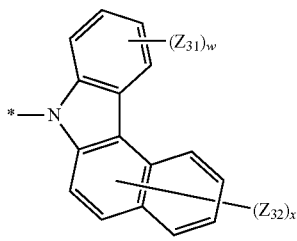

Formula 5D

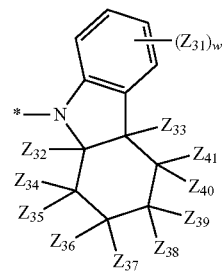

Formula 5E

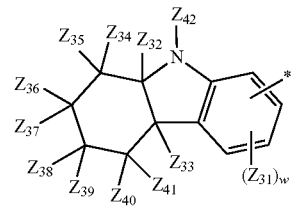

Formula 5F

Wherein $Z_{31}$ through $Z_{42}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, or a substituted or unsubstituted $C_1$-$C_{60}$ alkoxy group, or a substituted or unsubstituted $C_6$-$C_{60}$ aryl group; and w and x may be each independently an integer of 1 to 8.

For example, in Formulae 5A through 5F, $Z_{31}$ through $Z_{42}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a methyl group, an ethyl group, a propyl group, a butyl group, a pentyl group, a methoxy group, an ethoxy group, a propoxy group, a butoxy group, a pentoxy group, a phenyl group, a naphthyl group, or an anthryl group, but are not limited thereto.

For example, in Formula 1, at least one of —$N(R_1)(R_2)$ and —$N(R_3)(R_4)$ may be represented by one of Formulae 6A through 6F below, but are not limited thereto:

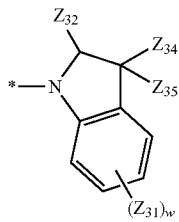

Formula 6A

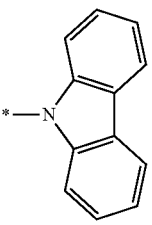

Formula 6B

-continued

Formula 6C
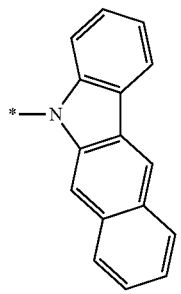

Formula 6D
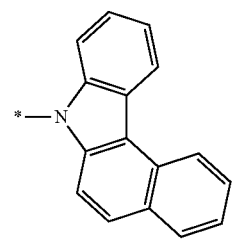

Formula 6E
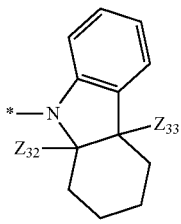

Formula 6F
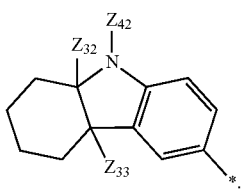

In Formulae 6A through 6F, a detailed description of $Z_{31}$, $Z_{32}$, $Z_{33}$, $Z_{34}$, $Z_{35}$, and $Z_{42}$ is already provided above. For example, $Z_{31}$, $Z_{32}$, $Z_{33}$, $Z_{34}$, and $Z_{35}$ may be each independently hydrogen or a substituted or unsubstituted $C_1$-$C_{10}$ alkyl group, and $Z_{42}$ may be a phenyl group, a naphthyl group, or an anthryl group.

In Formula 1, $X_1$ through $X_{10}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, —Si($R_{21}$)($R_{22}$)($R_{23}$), or —N($R_{24}$)($R_{25}$); and where $R_{21}$ through $R_{25}$ may be each independently hydrogen, deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group.

For example, in Formula 1, $X_1$ through $X_{10}$ may be each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{10}$ alkyl group, a substituted or unsubstituted $C_1$-$C_{10}$ alkoxy group, or a substituted or unsubstituted $C_6$-$C_{14}$ aryl group. At least two adjacent substituents of $X_1$ through $X_{10}$ may be linked to each other to form a saturated or unsaturated ring.

The condensed-cyclic compound may be one of Compounds 1 through 78 below, but is not limited thereto; wherein TMS is trimethyl silyl:

Compound 1

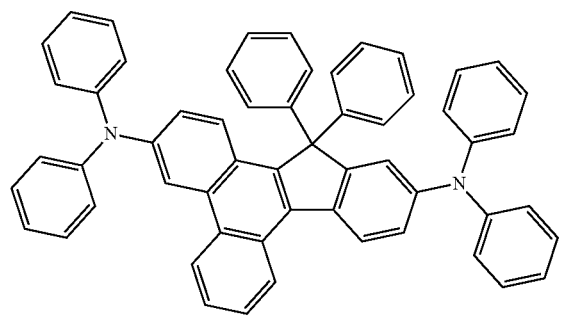

Compound 2

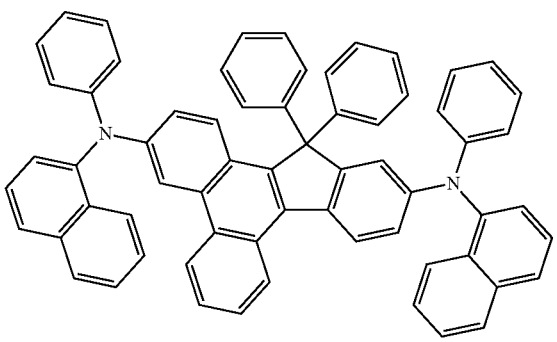

-continued
Compound 3
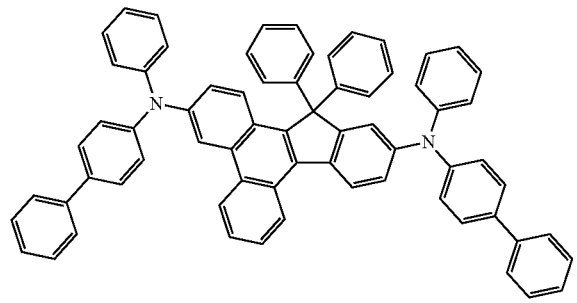
Compound 4
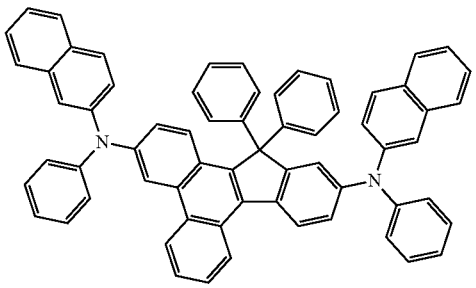
Compound 5
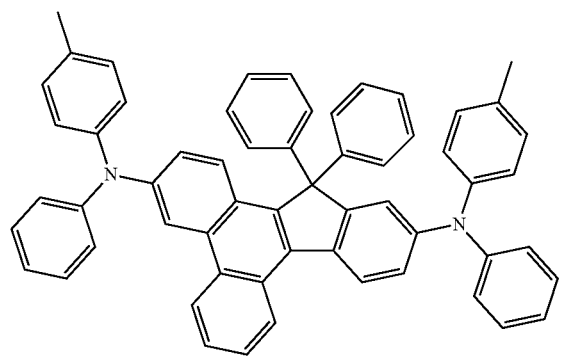
Compound 6
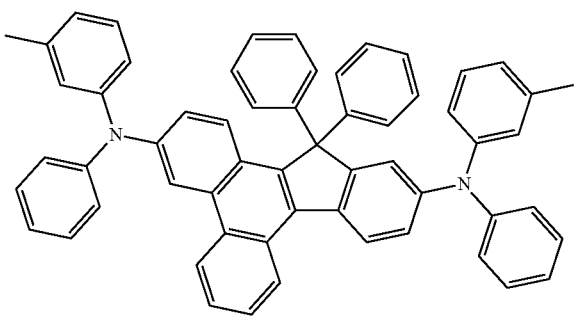
Compound 7
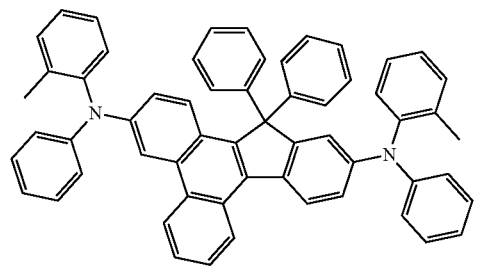
Compound 8
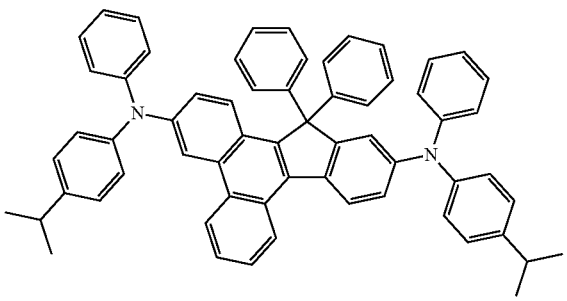
Compound 9
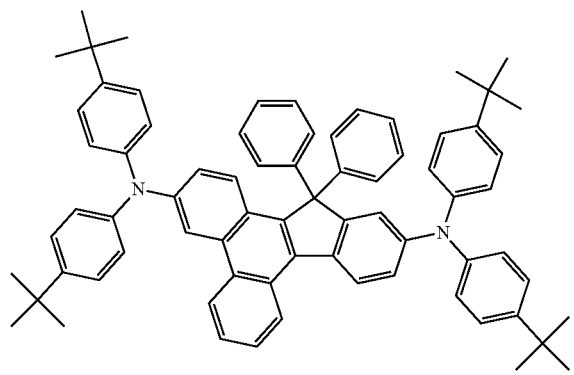
Compound 10
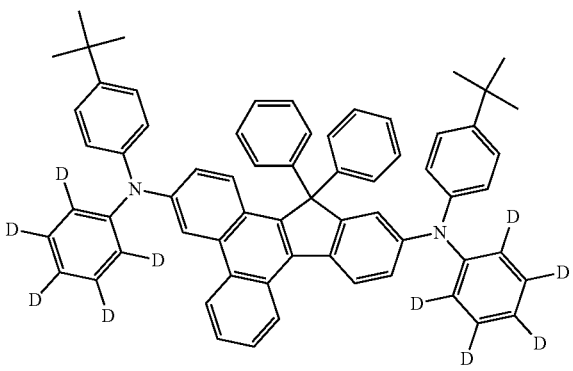

Compound 11
Compound 12
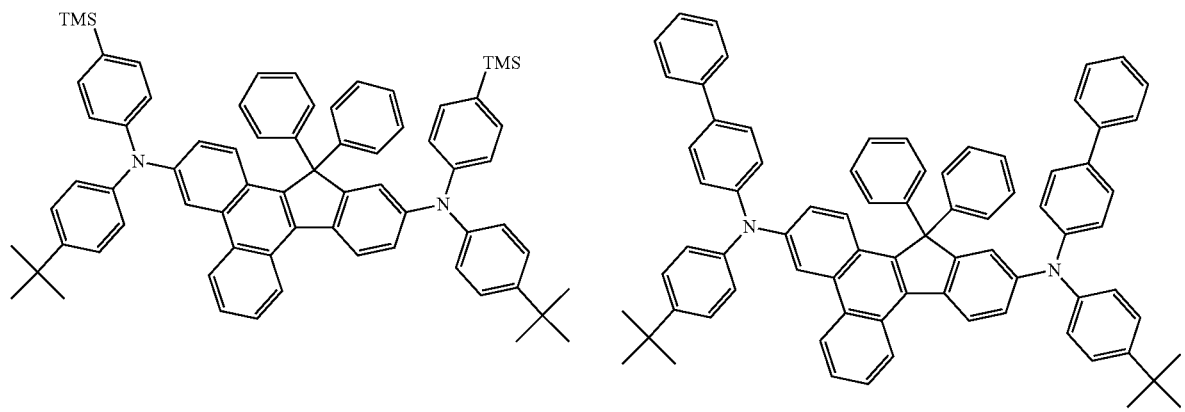
Compound 13
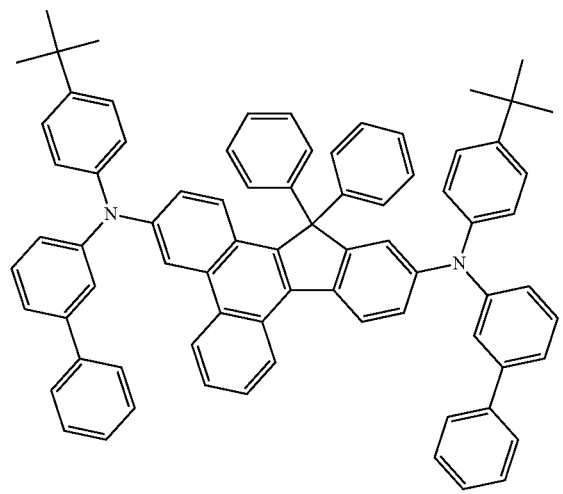
Compound 14
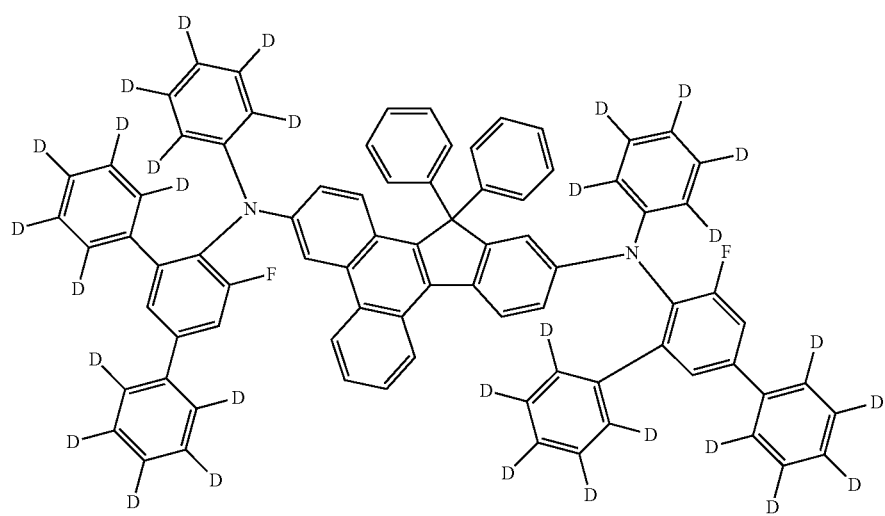

-continued
Compound 15
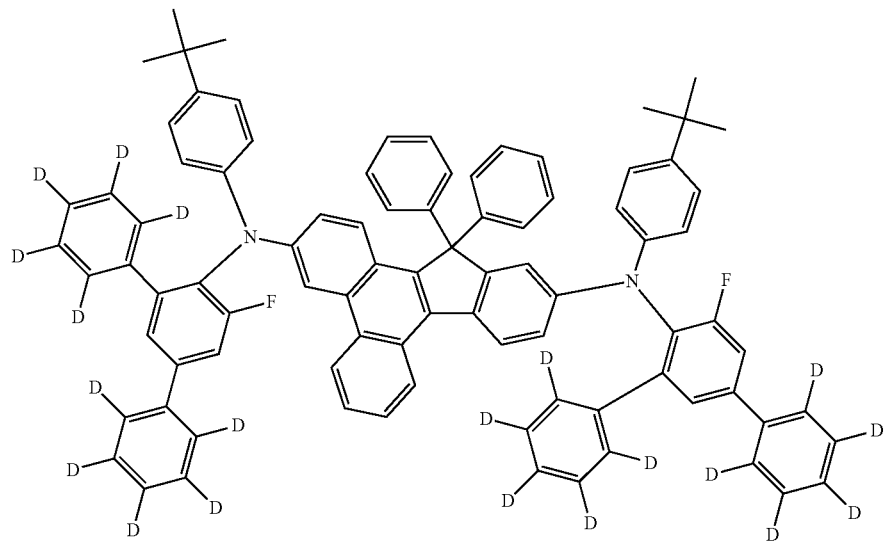
Compound 16
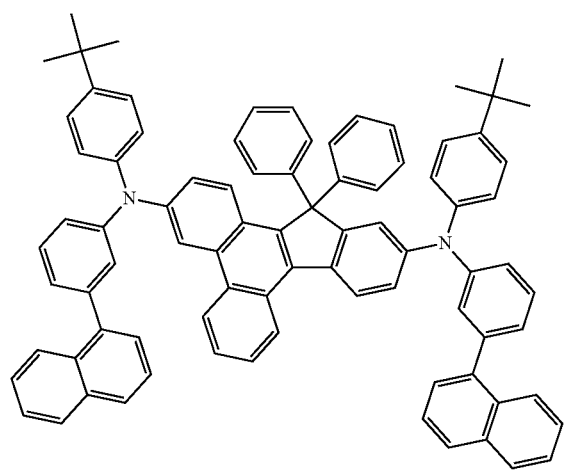
Compound 17
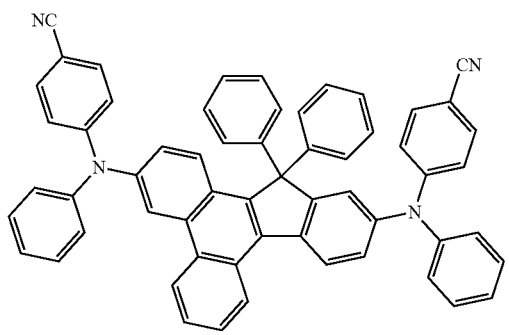
Compound 18
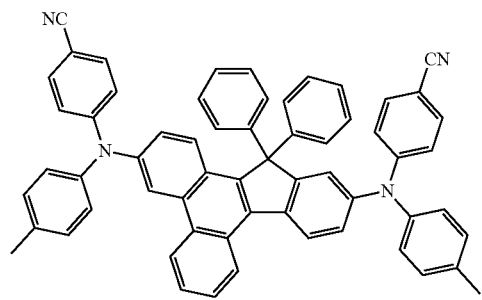
Compound 19
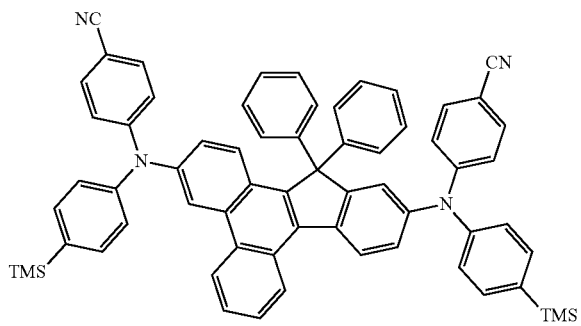

-continued
Compound 20
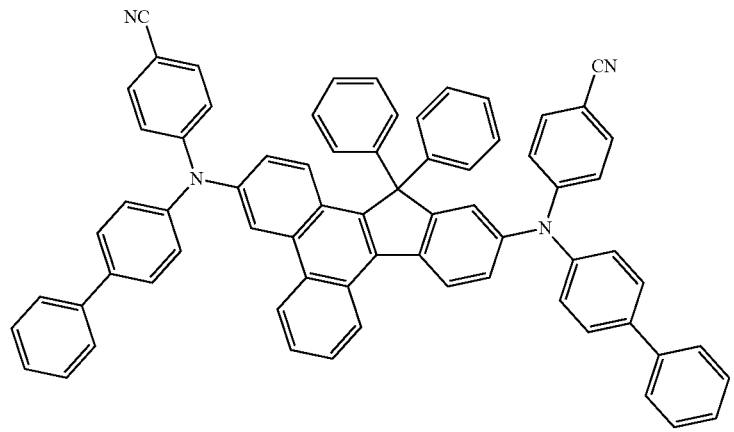
Compound 21
Compound 22
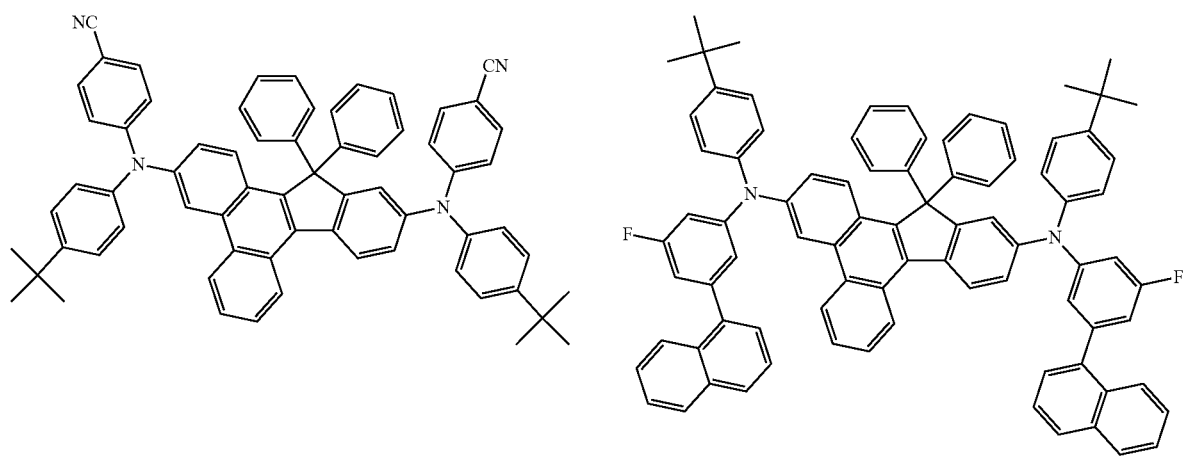
Compound 23
Compound 24
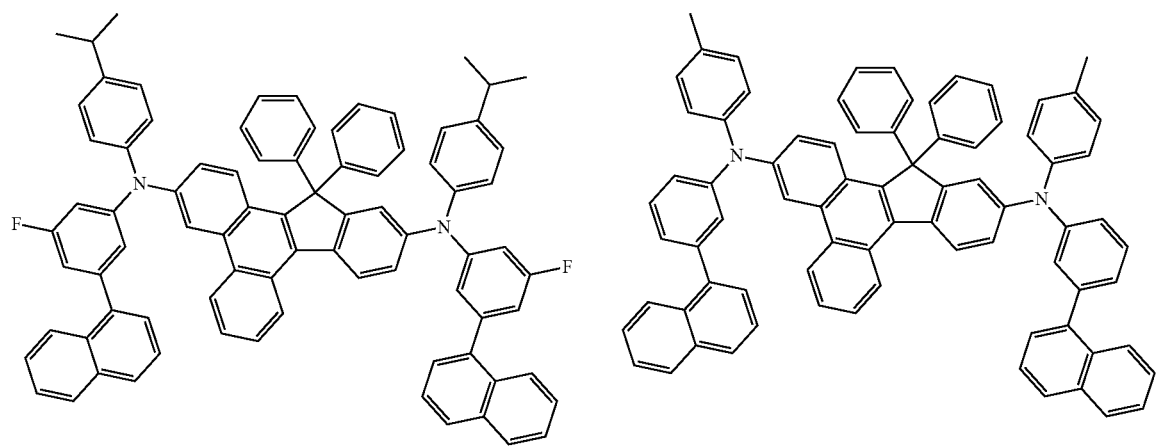

Compound 25
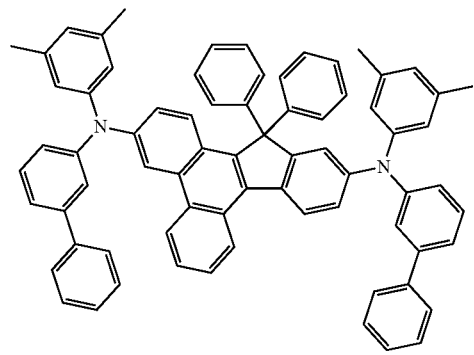
Compound 26
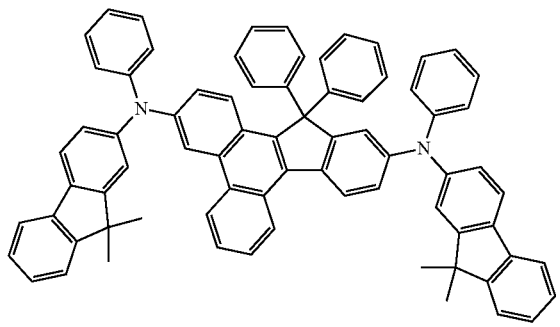
Compound 27
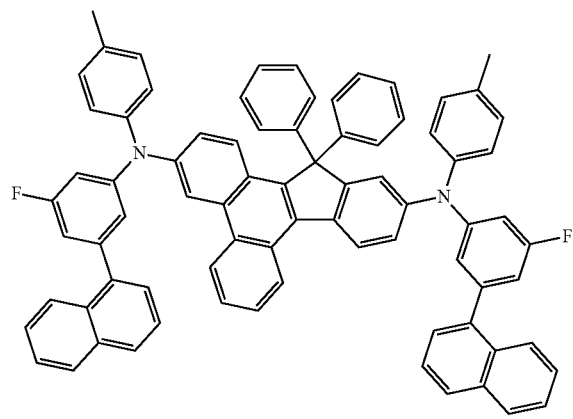
Compound 28
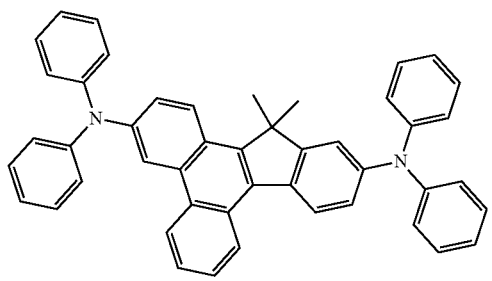
Compound 29
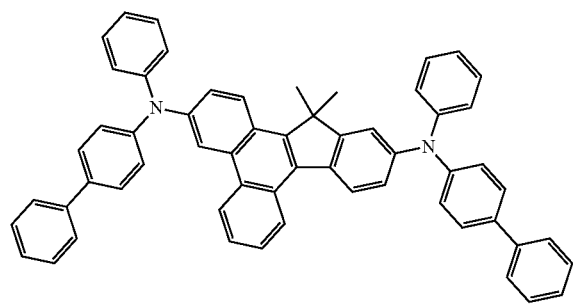
Compound 30
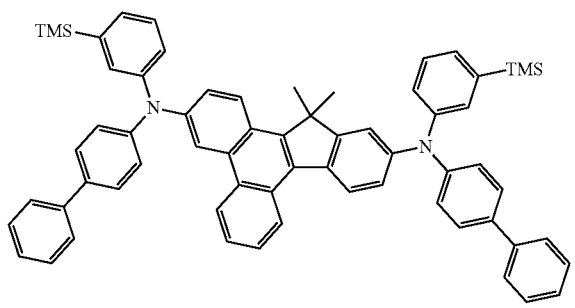
Compound 31
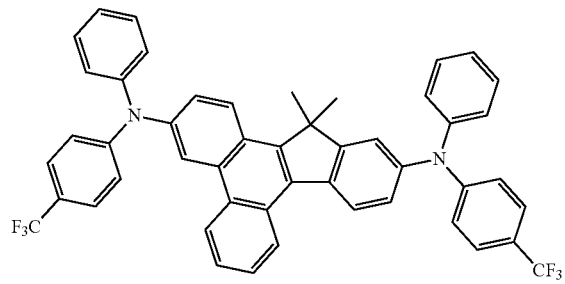
Compound 32
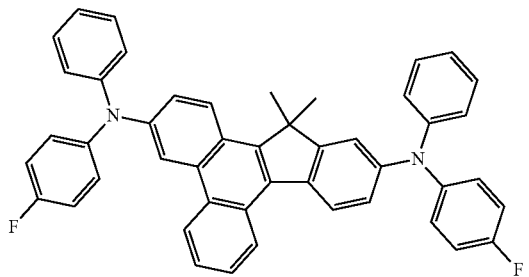

-continued
Compound 33
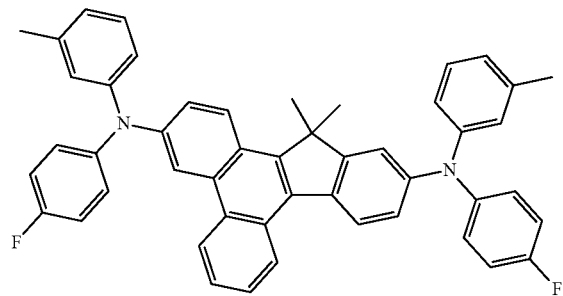
Compound 34
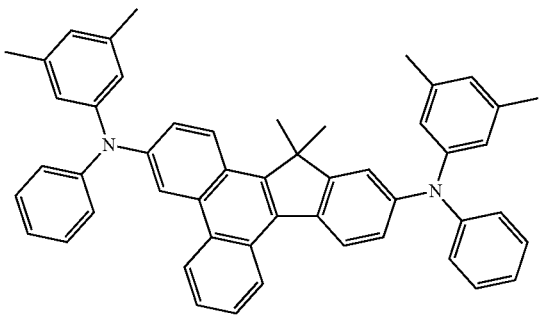
Compound 35
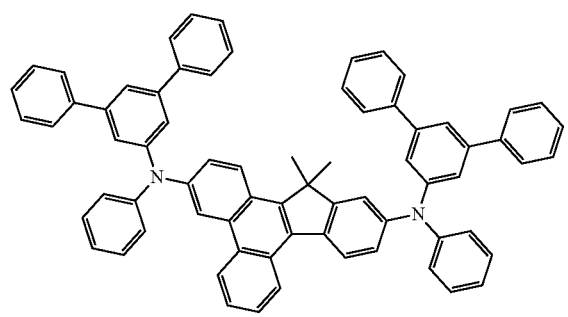
Compound 36
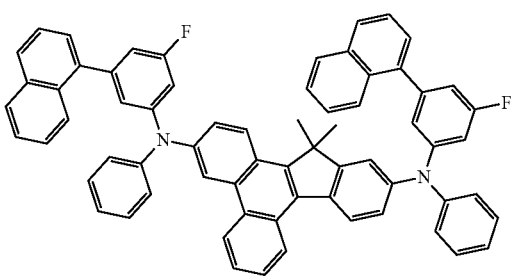
Compound 37
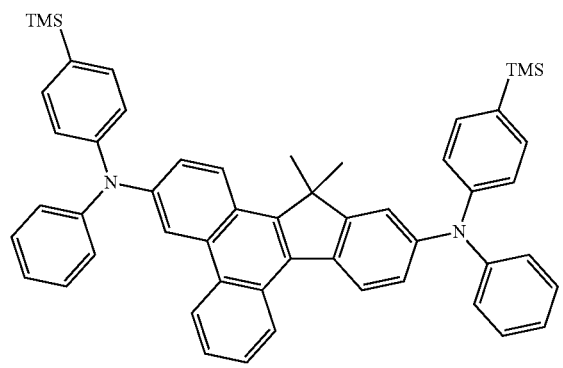
Compound 38
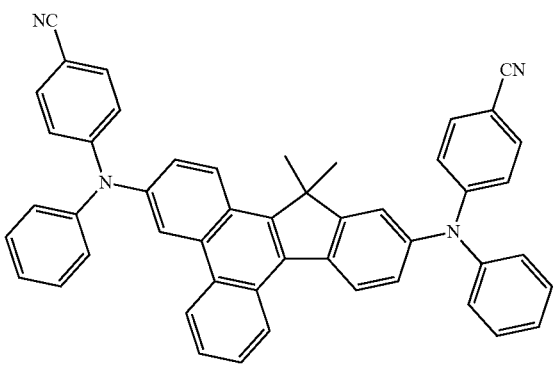
Compound 39
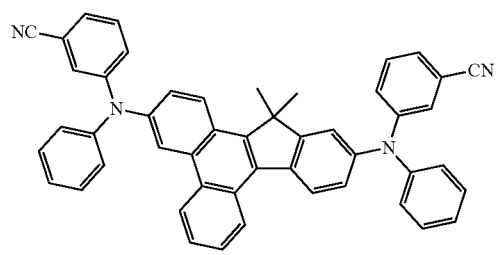
Compound 40
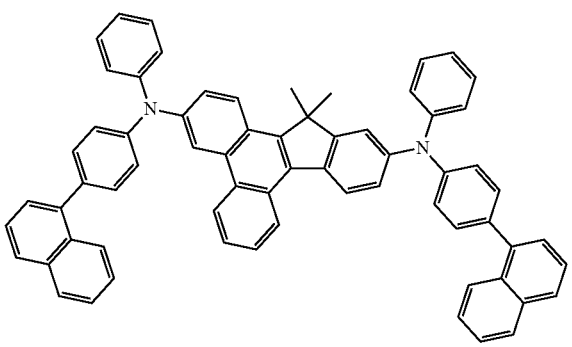

-continued
Compound 41
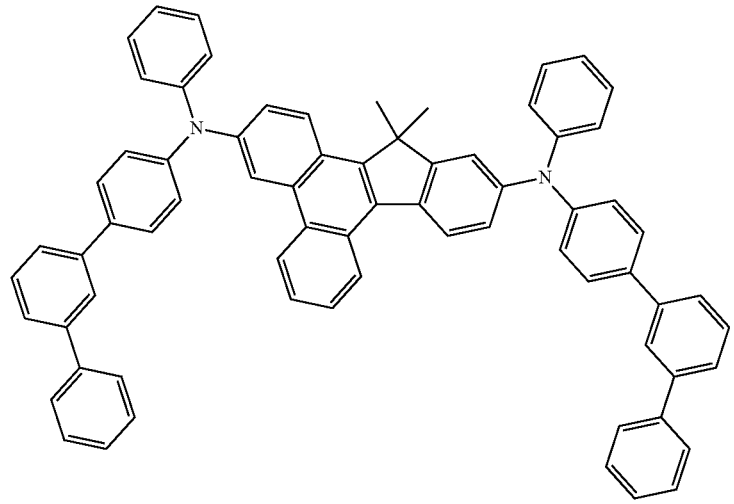
Compound 42
Compound 43
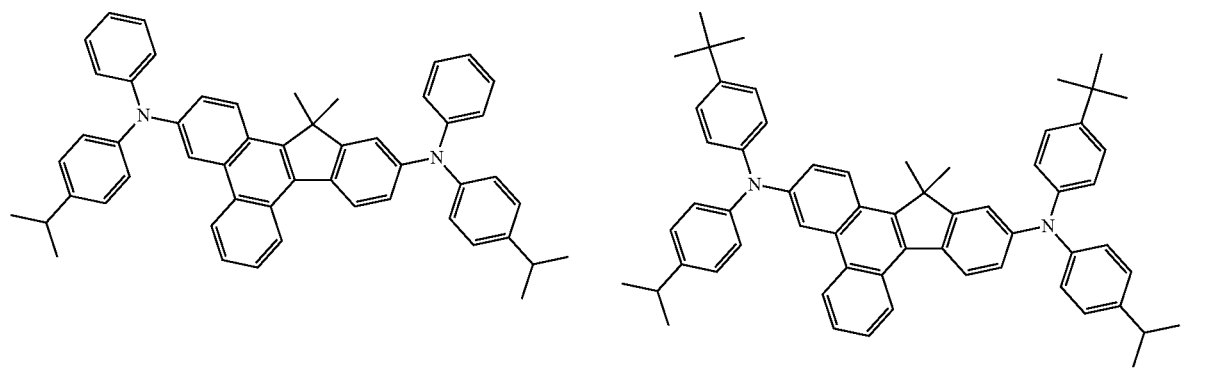
Compound 44
Compound 45
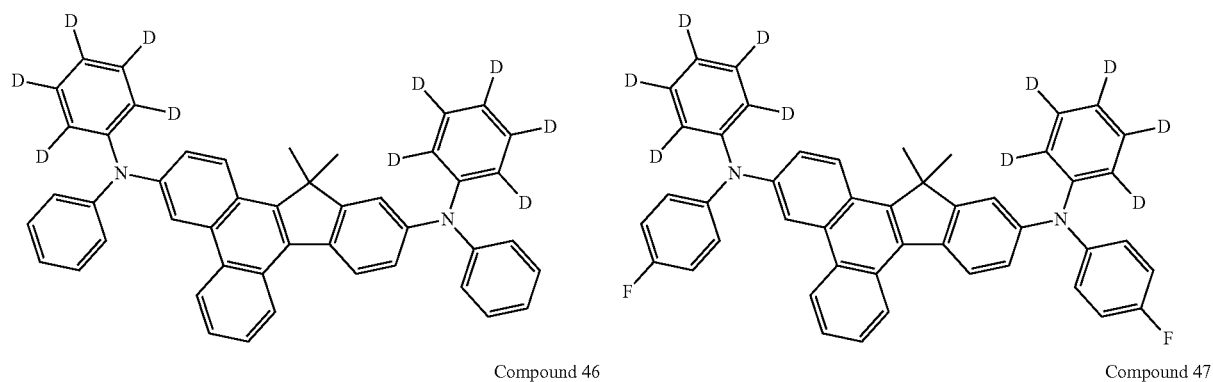
Compound 46
Compound 47
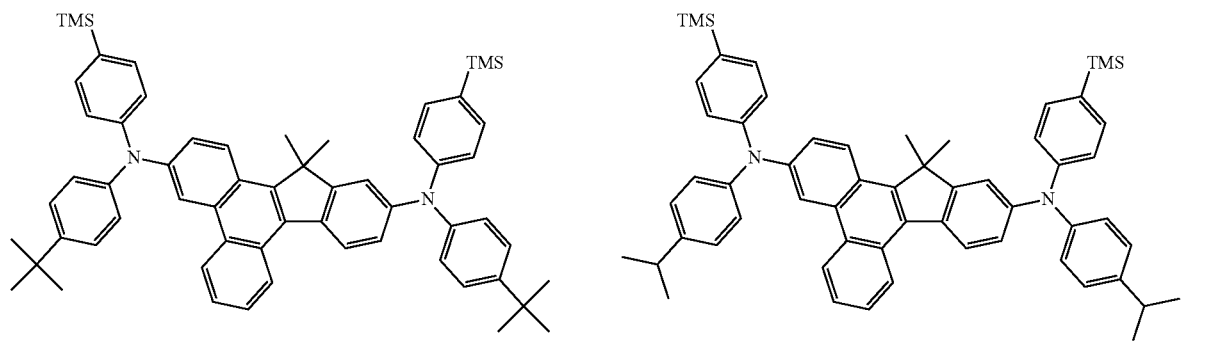

-continued
Compound 48
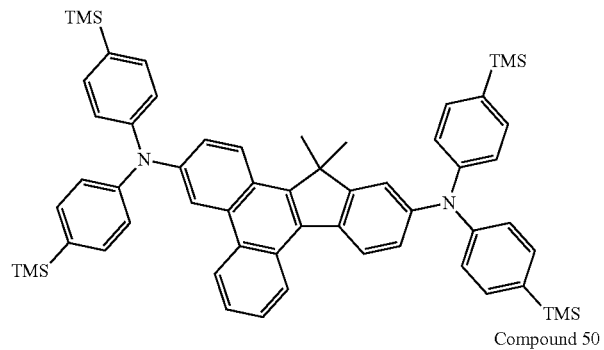
Compound 49
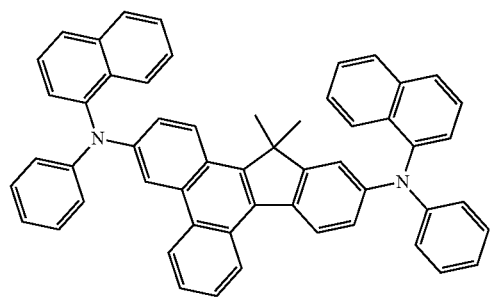
Compound 50
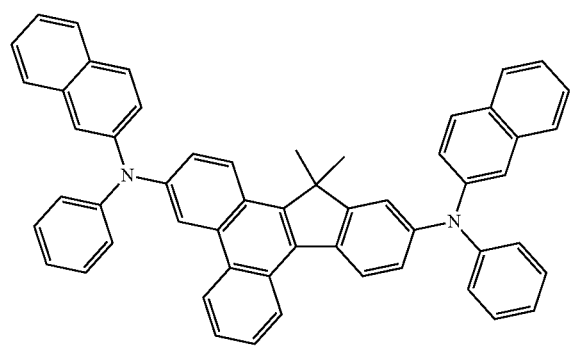
Compound 51
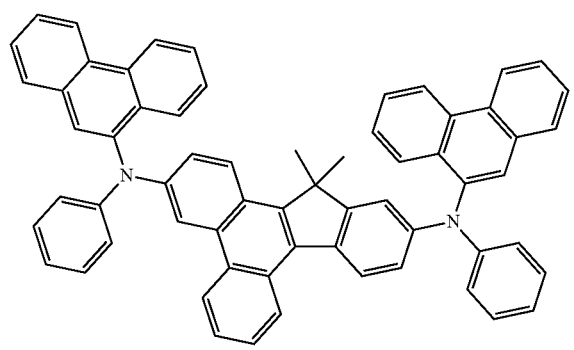
Compound 52
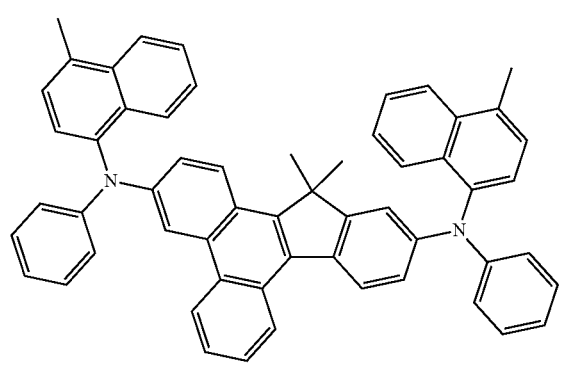
Compound 53
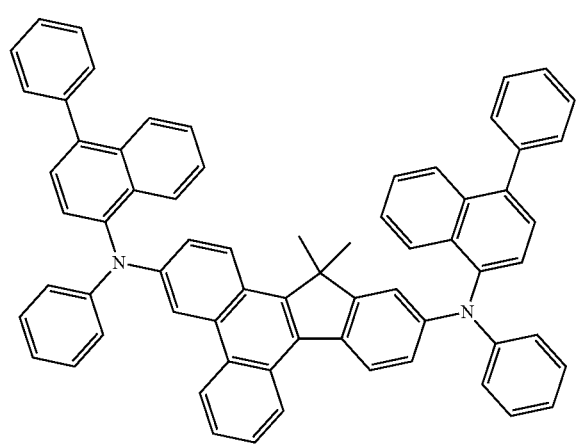
Compound 54
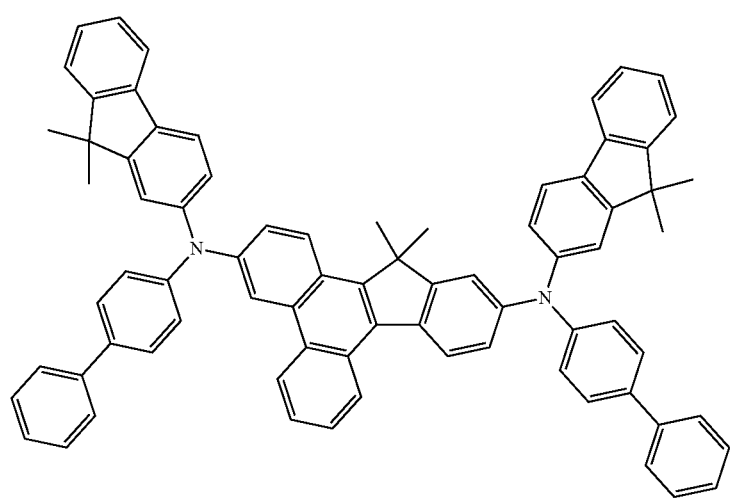

-continued
Compound 55
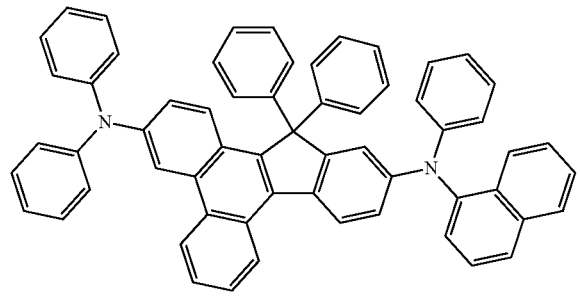
Compound 56
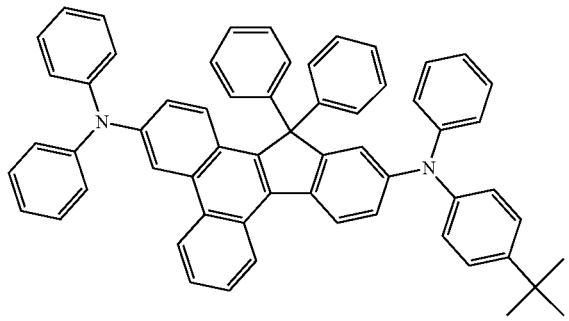
Compound 57
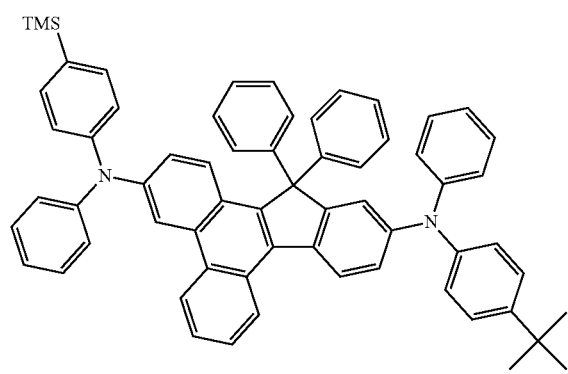
Compound 58
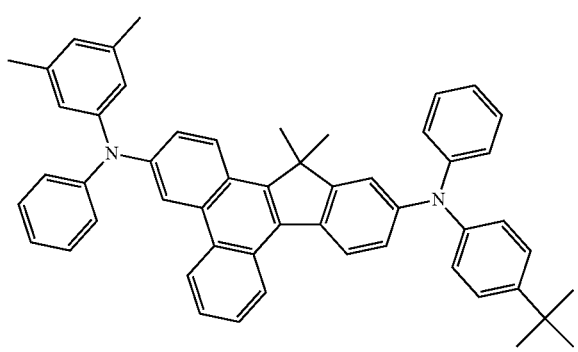
Compound 59
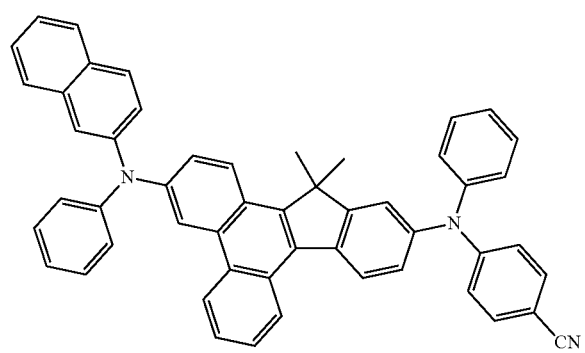
Compound 60
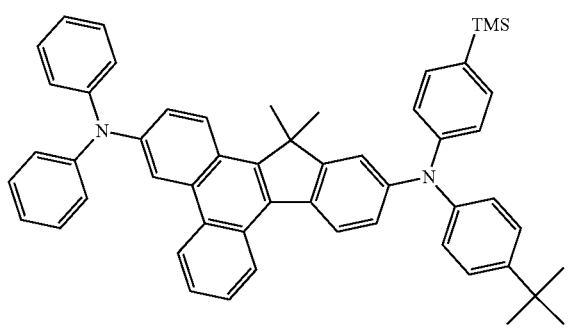
Compound 61
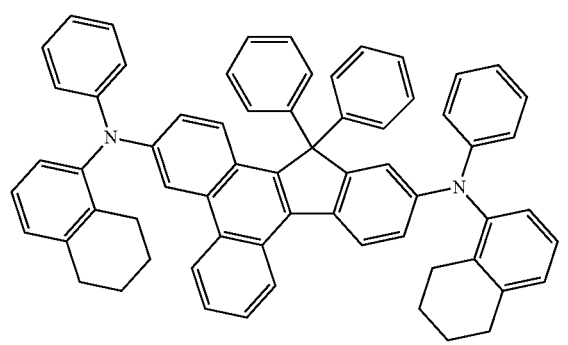
Compound 62
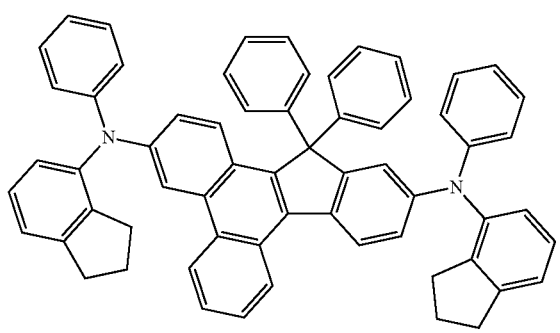

-continued
Compound 63
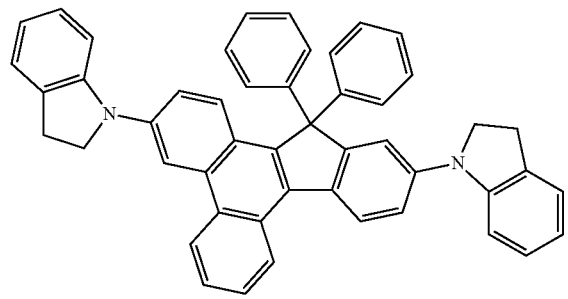
Compound 64
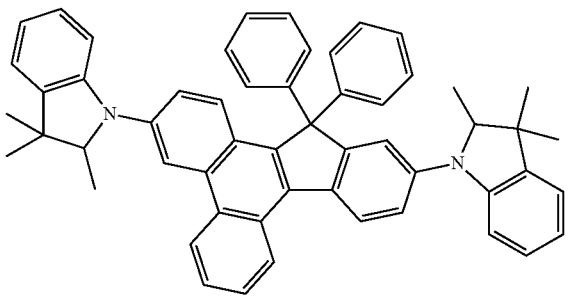
Compound 65
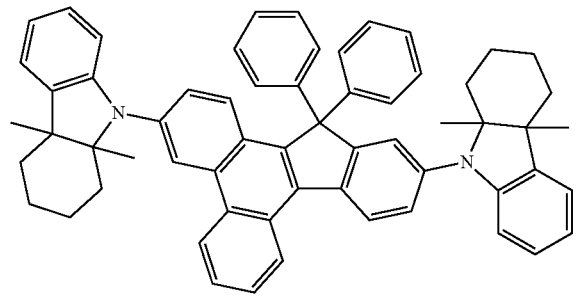
Compound 66
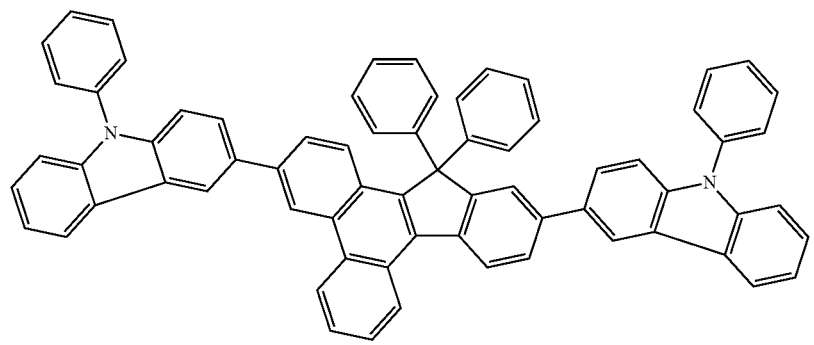
Compound 67
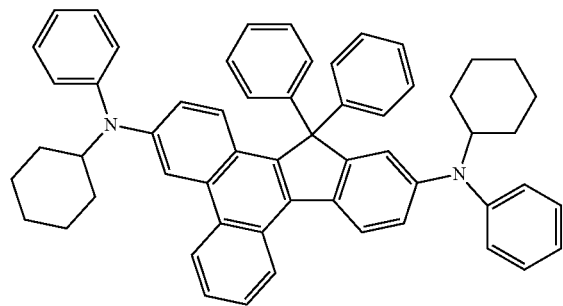
Compound 68
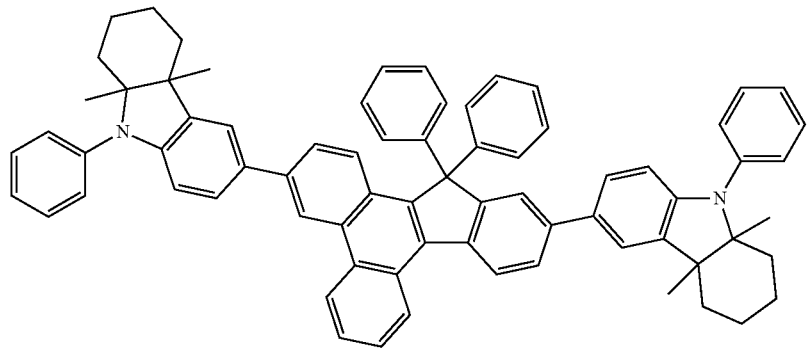

Compound 69
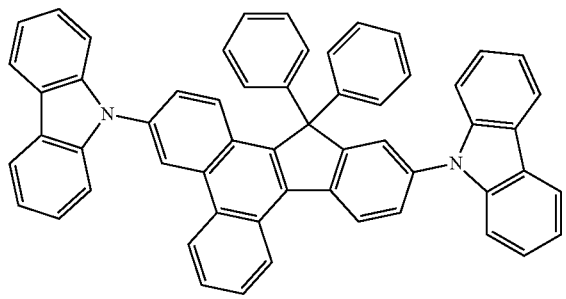
Compound 70
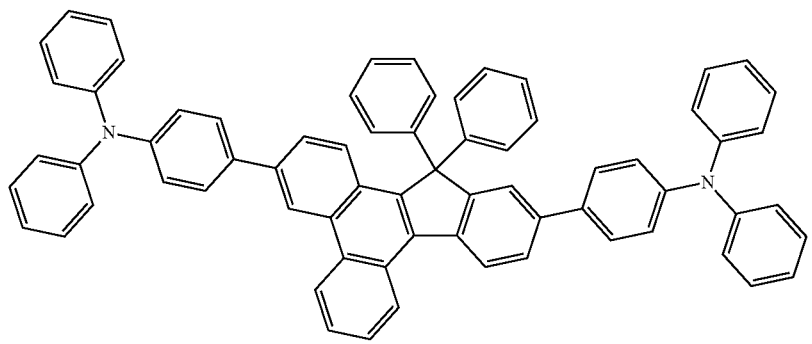
Compound 71
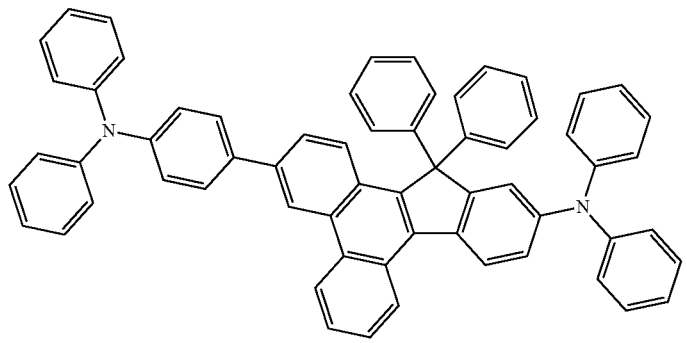
Compound 72
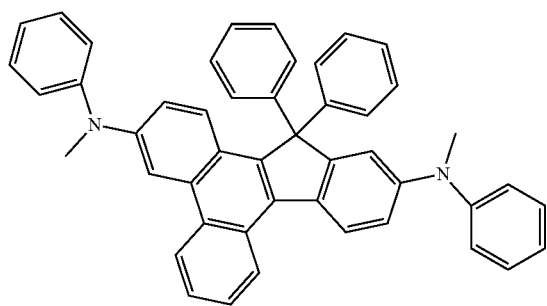
Compound 73
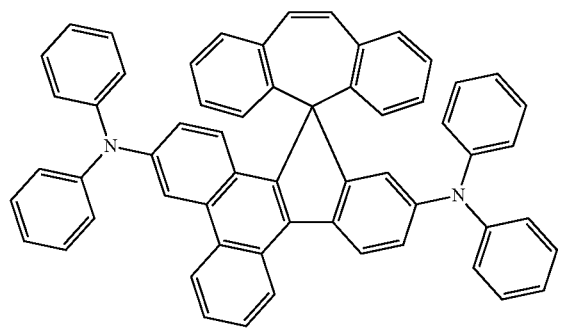

Compound 74
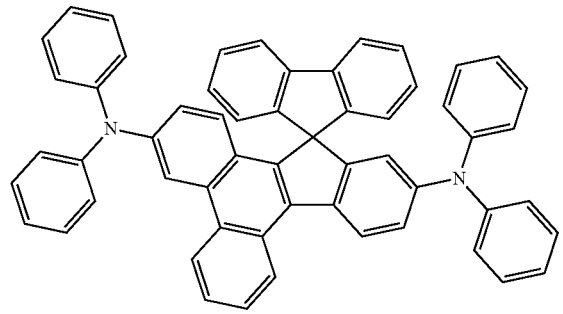
Compound 75
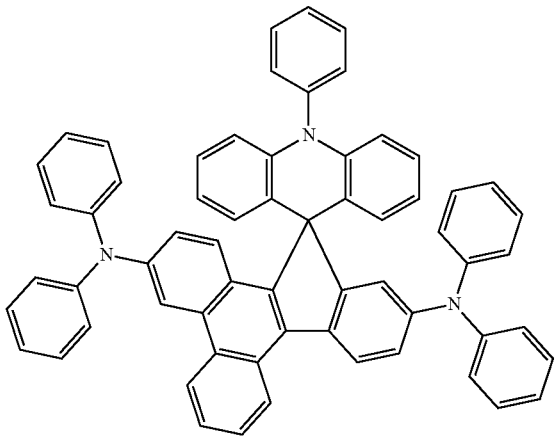
Compound 76
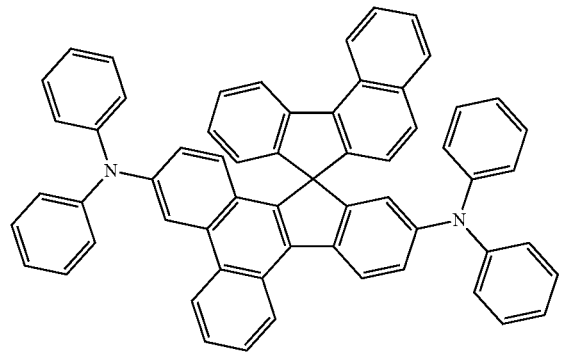
Compound 77
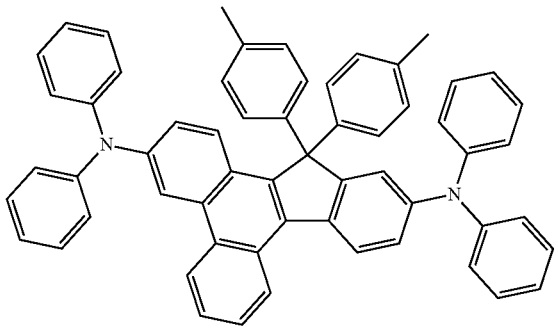
Compound 78
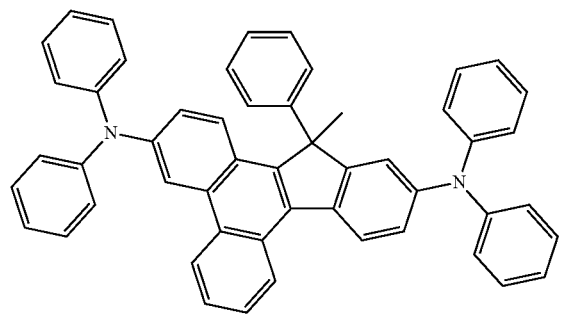
In some embodiments of the present invention, the condensed-cyclic compound may be one of Compounds 1A through 3A and 5A to 30A below, but is not limited thereto; wherein TMS is trimethyl silyl:
<Compound 1A>
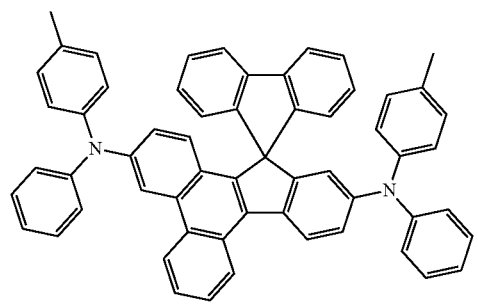
<Compound 2A>
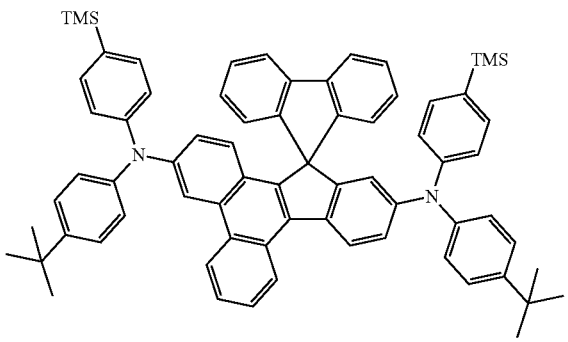

-continued
<Compound 3A>
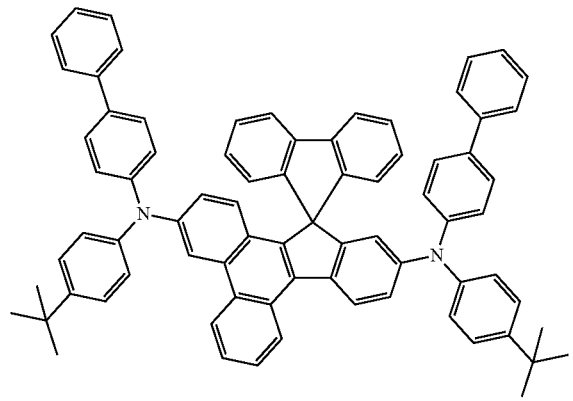
<Compound 5A>
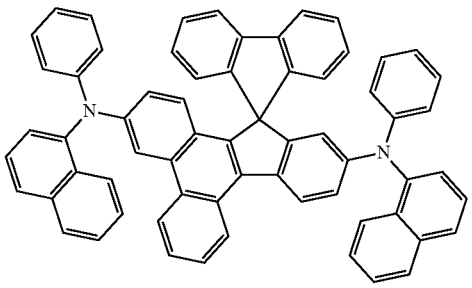
<Compound 6A>
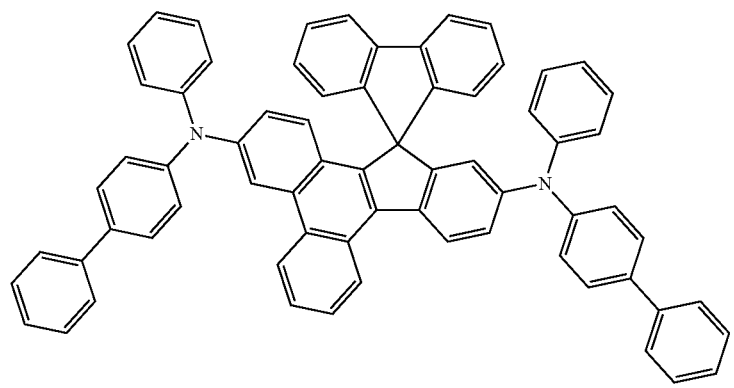
<Compound 7A>
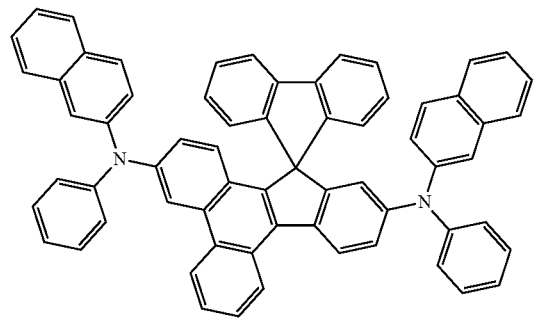
<Compound 8A>
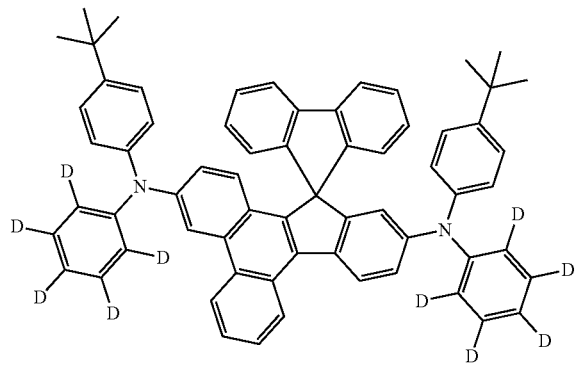
<Compound 9A>
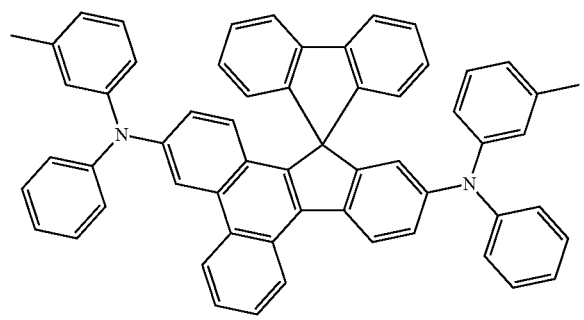
<Compound 10A>
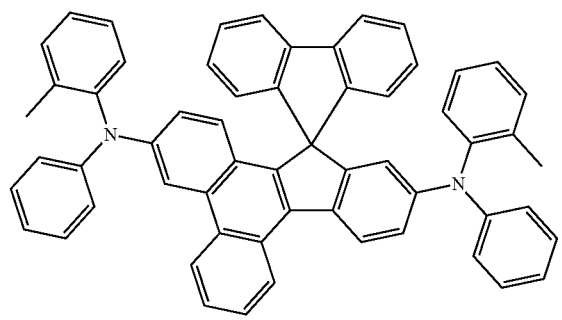

<Compound 11A>
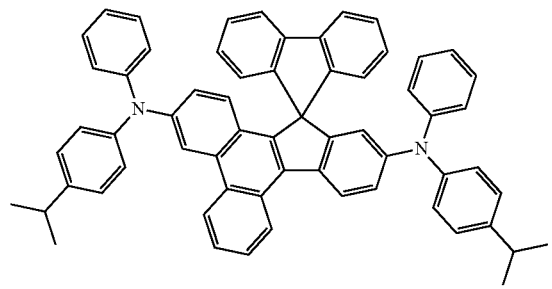
<Compound 12A>
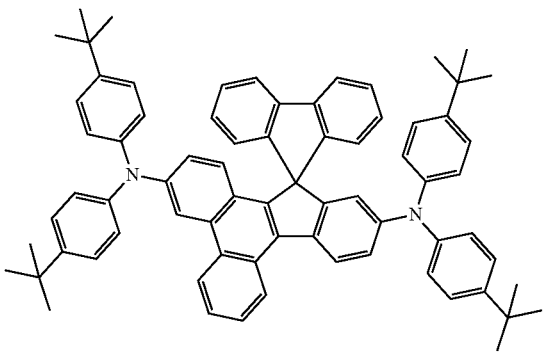
<Compound 13A>
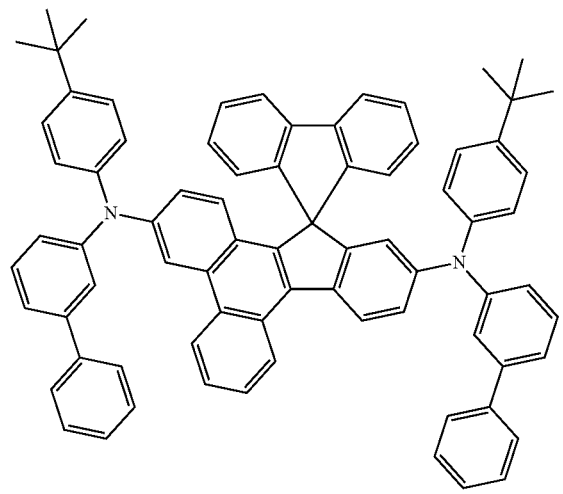
<Compound 14A>
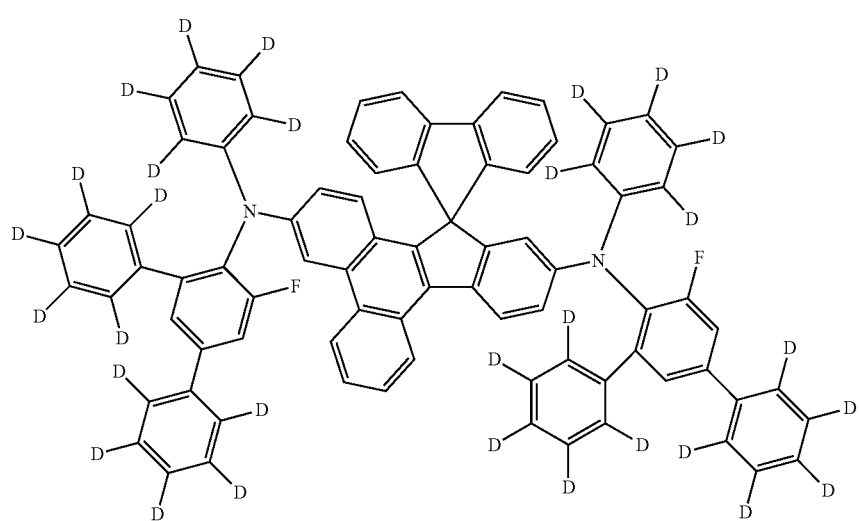

<Compound 15A>
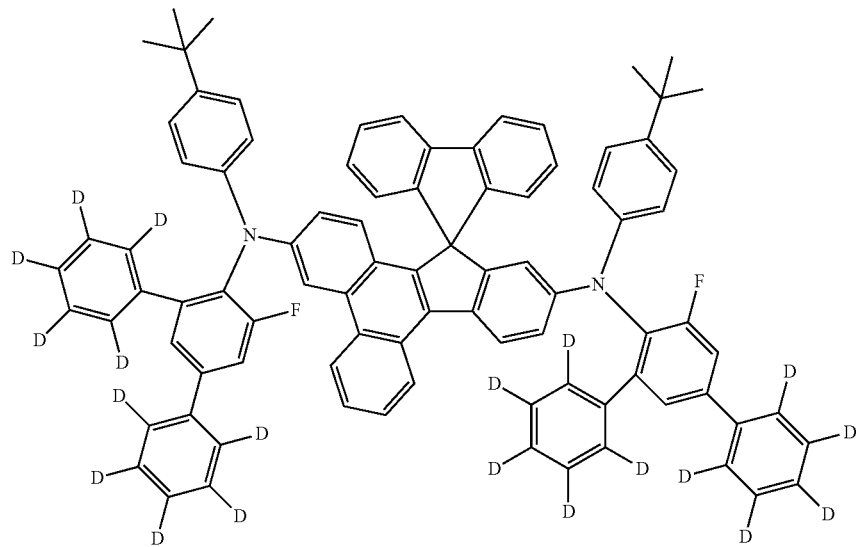
<Compound 16A>          <Compound 17A>
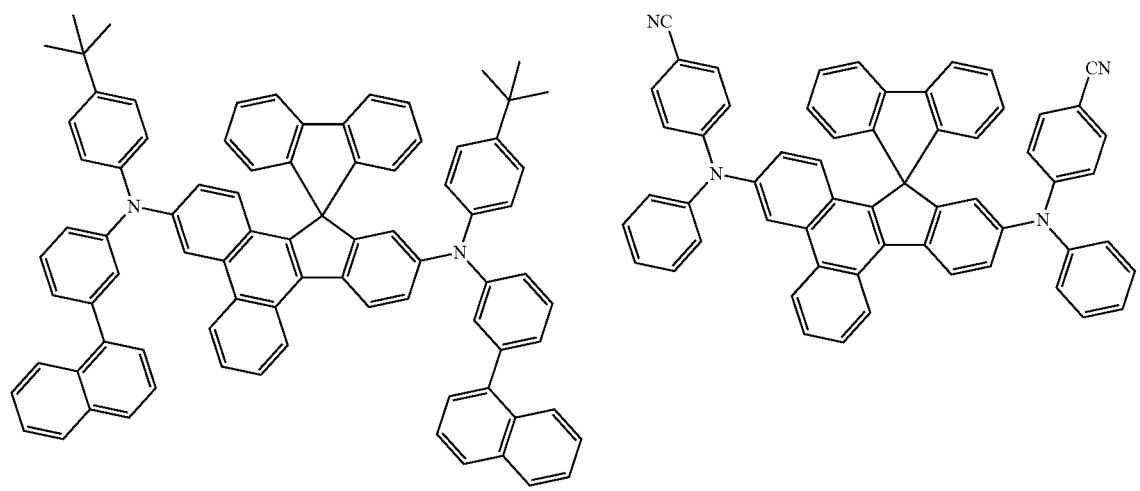
<Compound 18A>          <Compound 19A>
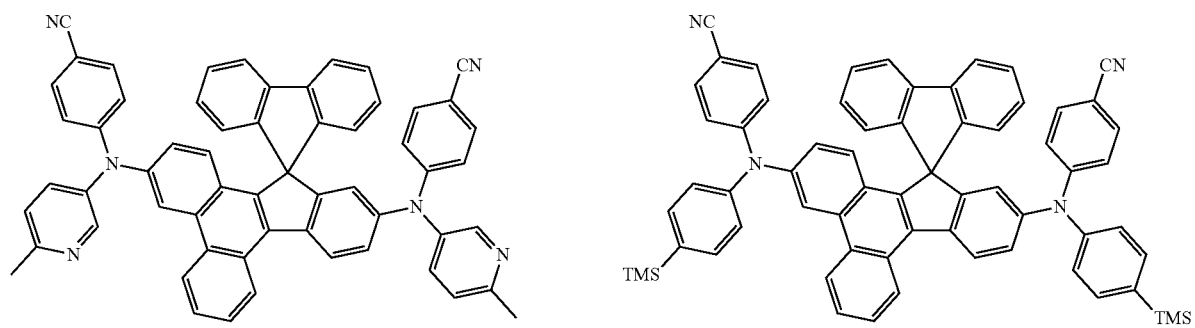

-continued
<Compound 20A>
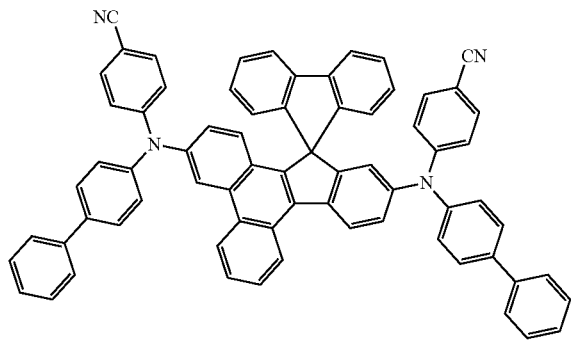
<Compound 21A>
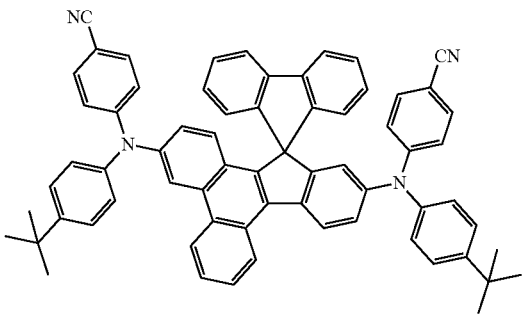
<Compound 22A>
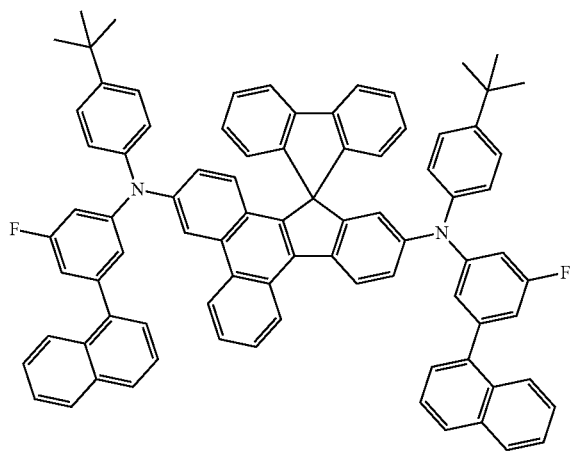
<Compound 23A>
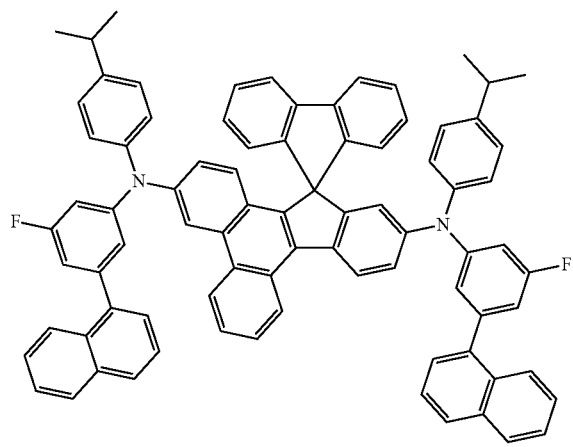
<Compound 24A>
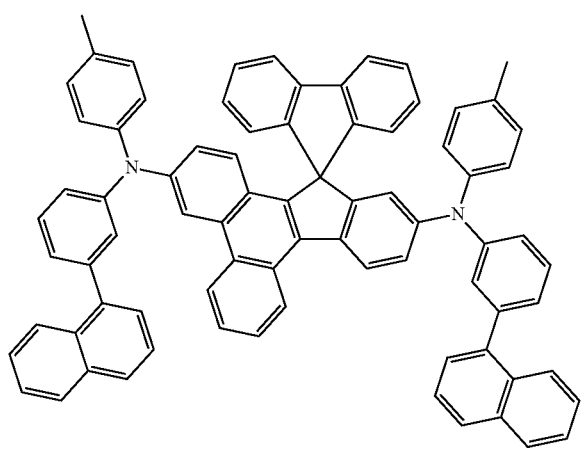
<Compound 25A>
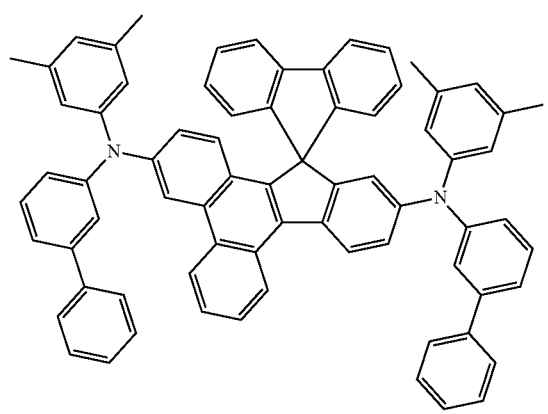

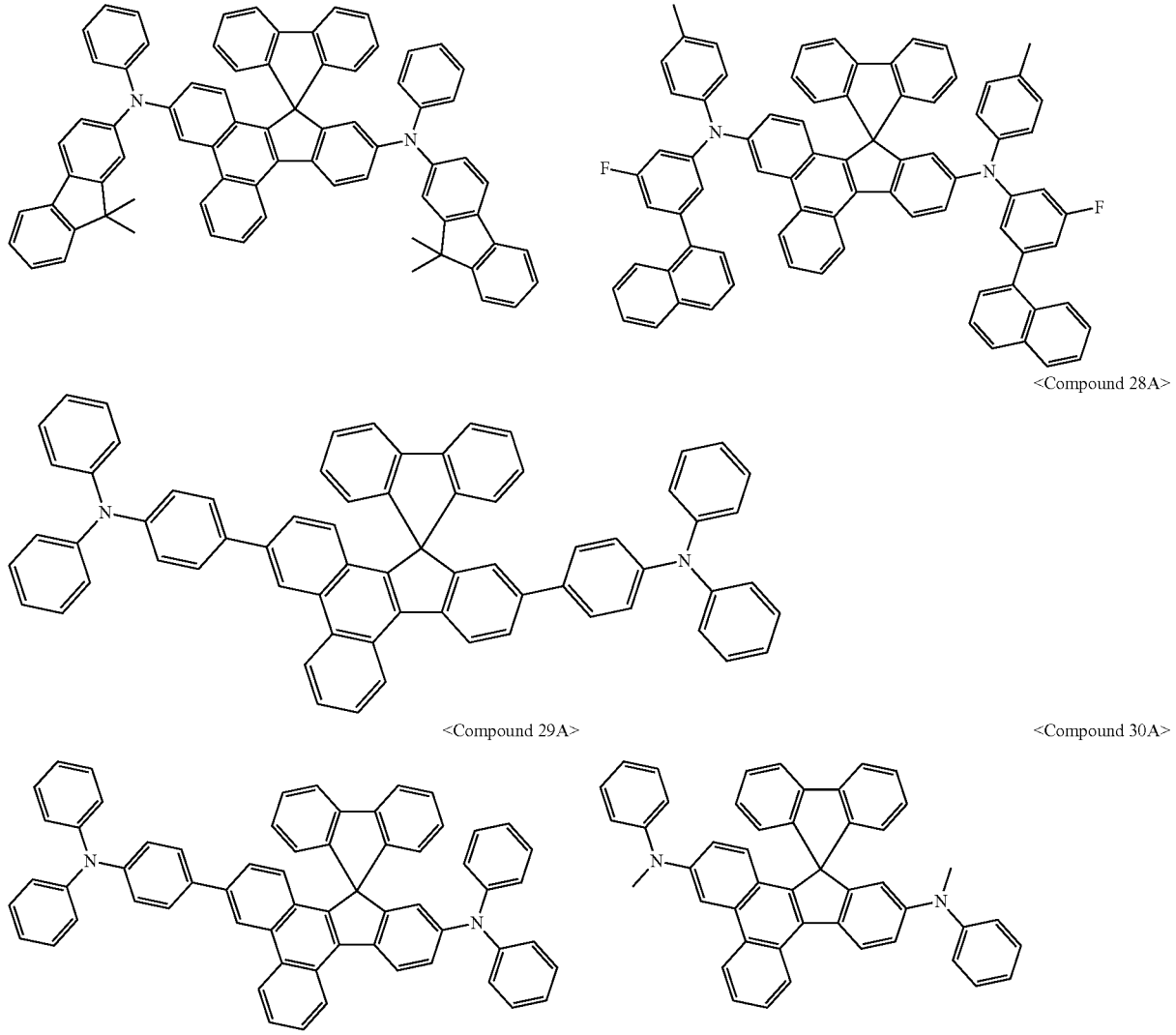

Examples of the unsubstituted $C_1$-$C_{60}$ alkyl group (or $C_1$-$C_{60}$ alkyl group) include methyl, ethyl, propyl, isobutyl, sec-butyl, pentyl, iso-amyl, hexyl, and the like. The substituted $C_1$-$C_{60}$ alkyl group may be a group in which at least one hydrogen of the unsubstituted $C_1$-$C_{60}$ alkyl group is substituted with deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ cycloalkyl group; a $C_6$-$C_{60}$ aryl group; a $C_6$-$C_{60}$ aryloxy group; a $C_6$-$C_{60}$ arylthio group; a $C_2$-$C_{60}$ heteroaryl group; a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_6$-$C_{60}$ aryl group, a $C_6$-$C_{60}$ aryloxy group, a $C_6$-$C_{60}$ arylthio group, or a $C_2$-$C_{60}$ heteroaryl group that is substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; —N($Q_1$)($Q_2$); or —Si($Q_3$)($Q_4$)($Q_5$) ($Q_1$ through $Q_5$ maybe be each independently a $C_3$-$C_{60}$ cycloalkyl group; a $C_6$-$C_{60}$ aryl group; a $C_6$-$C_{60}$ aryloxy group; a $C_6$-$C_{60}$ arylthio group; a $C_2$-$C_{60}$ heteroaryl group); and a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_3$-$C_{60}$ cycloalkyl group, a $C_6$-$C_{60}$ aryl group, a $C_6$-$C_{60}$ aryloxy group, a $C_6$-$C_{60}$ arylthio group, or a $C_2$-$C_{60}$ heteroaryl group that is substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group.

The unsubstituted $C_1$-$C_{60}$ alkoxy group (or $C_1$-$C_{60}$ alkoxy group) has a formula of —OA (in this regard, A is the unsubstituted $C_1$-$C_{60}$ alkyl group as described above) and examples thereof include methoxy, ethoxy, isopropyloxy, and the like. At least one hydrogen atom of the unsubstituted $C_1$-$C_{60}$ alkoxy group may be substituted with the same substituent as in the substituted $C_1$-$C_{60}$ alkyl group described above.

The unsubstituted $C_2$-$C_{60}$ alkenyl group (or $C_2$-$C_{60}$ alkenyl group) is interpreted to contain at least one carbon-carbon double bond in the center or at a terminal of the unsubstituted $C_2$-$C_{60}$ alkyl group. Examples of the unsubstituted $C_2$-$C_{60}$ alkenyl group include ethenyl, propenyl, butenyl, and the like. At least one hydrogen atom of the unsubstituted $C_2$-$C_{60}$ alkenyl group may be substituted with the substituents described with reference to the substituted $C_1$-$C_{60}$ alkyl group described above.

The unsubstituted $C_2$-$C_{60}$ alkynyl group (or $C_2$-$C_{60}$ alkynyl group) is interpreted to contain at least one carbon-carbon triple bond in the center or at a terminal of the $C_2$-$C_{60}$ alkyl group defined above. Examples of the unsubstituted $C_2$-$C_{60}$ alkynyl group include ethynyl, propynyl, and the like. At least one hydrogen atom of the unsubstituted $C_2$-$C_{60}$ alkynyl group may be substituted with the substituents described with reference to the substituted $C_1$-$C_{60}$ alkyl group described above.

The unsubstituted $C_6$-$C_{60}$ aryl group indicates a monovalent group having an aromatic carbocyclic system that has 5 to 60 carbon atoms and at least one aromatic ring and the unsubstituted $C_6$-$C_{60}$ arylene group indicates a divalent group having an aromatic carbocyclic system that has 5 to 60 carbon atoms and at least one aromatic ring. If the $C_6$-$C_{60}$ aryl group and the $C_6$-$C_{60}$ arylene group each independently have two or more aromatic rings, the rings may be fused with each other. At least one hydrogen atom of each of the unsubstituted $C_6$-$C_{60}$ aryl group and the unsubstituted $C_6$-$C_{60}$ arylene group may be substituted with the substituents described with reference to the substituted $C_1$-$C_{60}$ alkyl group described above.

Examples of the unsubstituted $C_6$-$C_{60}$ aryl group include, but are not limited to, a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- and p-fluorophenyl group, and a dichlorophenyl group), a dicyanophenyl group, a trifluoromethoxyphenyl group, an o-, m-, and p-tolyl group, an o-, m- and p-cumenyl group, a mesityl group, a phenoxyphenyl group, an ($\alpha,\alpha$-dimethylbenzene)phenyl group, a (N,N'-dimethyl) aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coroneryl group, a trinaphthylenyl group, a heptaphenyl group, a heptacenyl group, a pyranthrenyl group, and an ovalenyl group.

Examples of the substituted $C_6$-$C_{60}$ aryl group may be easily understood with reference to the examples of the unsubstituted $C_6$-$C_{60}$ aryl group described above and the substituents of the substituted $C_1$-$C_{60}$ alkyl group described above.

Examples of the substituted or unsubstituted $C_6$-$C_{60}$ arylene group may be easily understood with reference to the substituted or unsubstituted $C_6$-$C_{60}$ aryl group described above.

The unsubstituted $C_2$-$C_{60}$ heteroaryl group indicates a monovalent group having at least one aromatic ring system including carbon rings and at least one hetero atom selected from the group consisting of N, O, P, and S, and the unsubstituted $C_2$-$C_{60}$ heteroarylene group indicates a divalent group having at least one aromatic ring system including carbon rings and at least one hetero atom selected from the group consisting of N, O, P, and S. In this regard, if the $C_2$-$C_{60}$ heteroaryl group and the $C_2$-$C_{60}$ heteroarylene group each independently have two or more aromatic rings, the rings may be fused with each other. At least one hydrogen atom of each of the unsubstituted $C_2$-$C_{60}$ heteroaryl group and the unsubstituted $C_2$-$C_{60}$ heteroarylene group may be substituted with the substituents described with reference to the substituted $C_1$-$C_{60}$ alkyl group described above.

Examples of the unsubstituted $C_2$-$C_{60}$ heteroaryl group include, but are not limited to, a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, and an imidazopyrimidinyl group. Examples of the substituted or unsubstituted $C_2$-$C_{60}$ heteroarylene group may be easily understood with reference to the examples of the substituted or unsubstituted $C_2$-$C_{60}$ heteroarylene group described above.

The substituted or unsubstituted $C_6$-$C_{60}$ aryloxy group has a formula of —$OA_2$ wherein $A_2$ is the substituted or unsubstituted $C_6$-$C_{60}$ aryl group as described above, and the substituted or unsubstituted $C_6$-$C_{60}$ arylthio group has a formula of —$SA_3$ wherein $A_3$ is the substituted or unsubstituted $C_6$-$C_{60}$ aryl group described above.

The condensed-cyclic compound of Formula 1 may be synthesized using a well-known organic synthesis method. The synthesis method of the condensed-cyclic compound of Formula 1 may be easily understood by one of ordinary skill in the art with reference to Examples, which will be described later.

The condensed-cyclic compound of Formula 1 may have excellent thermal resistance and luminous properties. In particular, A-site carbon and B-site carbon of Formula 1 are linked respectively to —$N(R_1)(R_2)$ and —$N(R_3)(R_4)$, optionally, via $Ar_5$ and $Ar_6$, respectively.

In general, when conjugation lengths of backbone in condensed rings become longer, the band gap becomes smaller and thus the emission wavelength moves to longer wavelengths. On the other hand, the condensed-cyclic compound of Formula 1 has a structure in which the C-site carbon is broken conjugation of condensed rings between the A-site carbon and the B-site carbon as shown in Formula 1 below. Each of the C-site carbon, A-site carbon and B-site carbon is linked to an amine group and thus may form a wider band gap as compared to the conjugated structure. Thus, the condensed-cyclic compound of Formula 1 may be usefully used as a blue light-emitting material due to the wide band gap effected by an appropriate conjugation state.

Formula 1

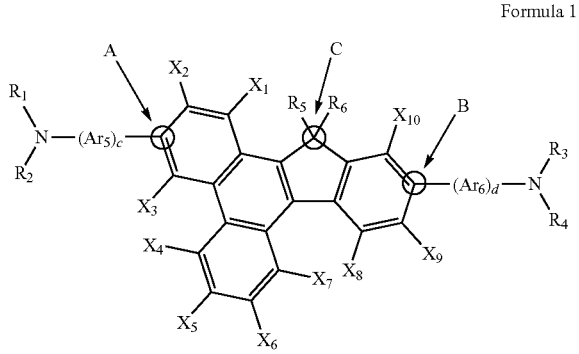

When an organic light-emitting diode (OLED) including the condensed-cyclic compound of Formula 1 between a pair of electrodes (anode and cathode) is operated, the OLED may exhibit excellent driving voltage, efficiency, brightness and life-time characteristics since the condensed-cyclic compound of Formula 1 has high heat resistance to Joule's heat generated between organic layers positioned between the pair of electrodes or between one of the organic layers and one of the electrodes.

The condensed-cyclic compound of Formula 1 may be used between a pair of electrodes of an OLED. For example, the condensed-cyclic compound of Formula 1 may be used as a light-emitting material, but is not limited thereto.

According to another embodiment of the present invention, there is provided an OLED including a first electrode, a second electrode facing the first electrode, and an organic layer interposed between the first electrode and the second electrode, wherein the organic layer includes at least one of the condensed-cyclic compound of Formula 1 described above.

The organic layer may include at least one of the condensed-cyclic compound of Formula 1. For example, an OLED manufactured according to Example 1, which will be described later, includes only Compound 1 (acting as a blue dopant) as the condensed-cyclic compound of Formula 1. Alternatively, an emission layer of the OLED may include Compounds 1 and 3 (acting as a blue dopant) as the condensed-cyclic compound of Formula 1. That is, various modifications are possible in this embodiment. As used herein, the expression "the organic layer may include at least one of the condensed-cyclic compound of Formula 1" may be easily understood by one of ordinary skill in the art with reference to the above description.

The organic layer may include at least one of a hole injection layer (HIL), a hole transport layer (HTL), a functional layer having hole injection and hole transport abilities, an electron blocking layer (EBL), an emission layer (EML), a hole blocking layer (HBL), an electron transport layer (ETL), an electron injection layer (EIL), and a functional layer having electron transport and electron injection abilities.

For example, the organic layer may have, but is not limited to, a HIL/HTL/EML/ETL/EIL structure or a functional layer having hole injection and hole transport abilities/EML/ETL/EIL structure.

The term "organic layer" used herein refers to a single layer or multiple layers interposed between the first electrode and the second electrode and may include a metal complex in addition to an organic material.

For example, the organic layer may include an EML including the condensed-cyclic compound of Formula 1. In other words, the condensed-cyclic compound of Formula 1 may be used as a light-emitting material. In this regard, the EML may further include a host and the condensed-cyclic compound of Formula 1 included in the EML may serve as a dopant.

The EML may be a red, green or blue EML. For example, the EML may be a blue EML. In this regard, the condensed-cyclic compound of Formula 1 is used as a blue dopant, whereby an OLED including the condensed-cyclic compound of Formula 1 may have high efficiency, brightness and color purity and long lifetime.

FIG. 1 is a schematic cross-sectional view of an OLED according to an embodiment of the present invention. Hereinafter, a structure and manufacturing method of an OLED will be described in more detail with reference to FIG. 1. The OLED includes a substrate 10, a first electrode 20, a HIL 30, a HTL 40, an EML 50, an ETL 60, an EIL 70, and a second electrode 80 that are sequentially formed.

First, the substrate 10 may be a substrate used in a general OLED, and may be a glass substrate or a transparent plastic substrate having excellent mechanical strength, thermal stability, transparency, surface smoothness, ease of handling, and waterproofness.

The first electrode 20 may be formed by applying a first electrode material on the substrate 10 by deposition or sputtering. When the first electrode 20 is an anode, the first electrode material may be selected from materials having a high work function so as to facilitate hole injection. The first electrode 20 may be a reflective electrode or a transparent electrode. Examples of the first electrode material may include indium-tin oxide (ITO), indium-zinc-oxide (IZO), tin oxide ($SnO_2$), and zinc oxide (ZnO). Also, when magnesium (Mg), aluminum (Al), aluminum-lithium (Al—Li), calcium (Ca), magnesium-indium (Mg—In), or magnesium-silver (Mg—Ag) is used as the first electrode material, the first electrode 20 may be formed as a reflective electrode.

The first electrode 20 may be formed as a single layer or have a multi-layered structure having at least two layers.

An organic layer including the HIL 30, HTL 40, the EML 50, the ETL 60, and the EIL 70 is formed on the first electrode 20 sequentially.

The HIL 30 may be formed on the first electrode 20 by using various methods such as vacuum deposition, spin coating, casting, or LB deposition.

When the HIL 30 is formed by vacuum deposition, the deposition conditions may vary according to a compound used as a material for forming the HIL 30, a structure of a desired HIL, and thermal characteristics. For example, the deposition conditions may be, but are not limited to, a deposition temperature of about 100° C. to about 500° C., a degree of vacuum of about $10^{-8}$ torr to about $10^{-3}$ torr, and a deposition speed of about 0.01 Å/sec to about 100 Å/sec.

When the HIL 30 is formed by spin coating, the coating conditions may vary according to a compound used as a material for forming the HIL 30, a structure of a desired HIL, and thermal characteristics. For example, the coating conditions may be, but are not limited to, a coating speed of about 2,000 rpm to about 5,000 rpm and a heat treatment temperature for removing a solvent after coating of about 80° C. to about 200° C.

The material for forming the HIL 30 may be a known hole injection material. Examples of the known hole injection material include, but are not limited to, N,N'-diphenyl-N, N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), 4,4' 4"-tris(N,N-diphenylamino)triphenylamine (TDATA), 4,4',4"-tris{N,-(2-naphthyl)-N-phenylamino}-triphenylamine (2T-NATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonicacid (PANI/CSA), and polyaniline/poly(4-styrenesulfonate) (PANI/PSS).

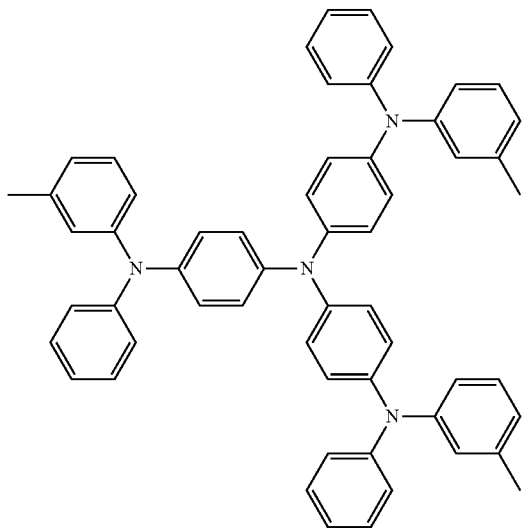

m-MTDATA

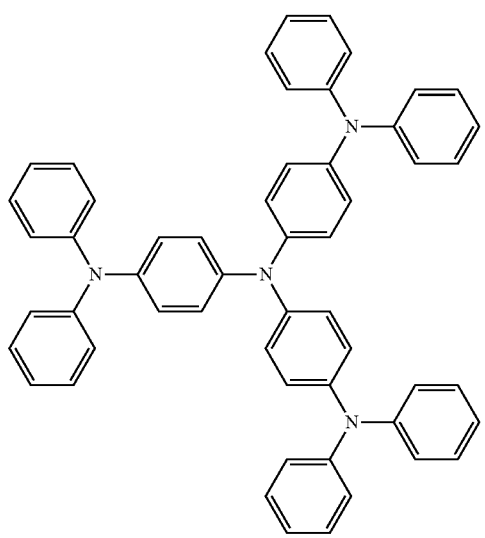

TDATA

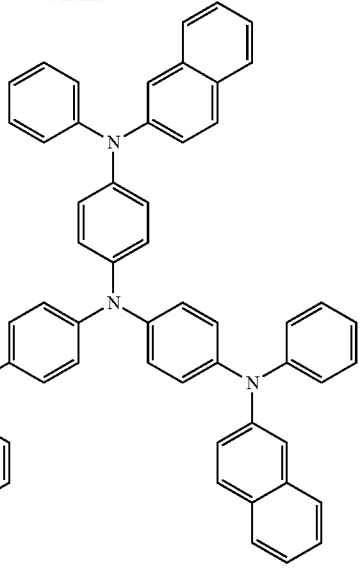

2-TNATA

The thickness of the HIL 30 may be in the range of about 100 Å to about 10,000 Å. In some embodiments, the thickness of the HIL 30 may be in the range of about 100 Å to about 1,000 Å. When the thickness of the HIL 30 is within these range, satisfactory hole injection properties may be obtained without a substantial increase in driving voltage.

Next, the HTL 40 may be formed on the HIL 30 by using various methods such as vacuum deposition, spin coating, casting, or LB deposition. When the HTL 40 is formed by vacuum deposition or spin coating, the deposition and coating conditions may vary according to used compounds. However, in general, the deposition and coating conditions may be almost the same as the conditions for forming the HIL 30.

A material for forming the HTL 40 may be a known hole transporting material. Examples of the known hole transporting material include, but are not limited to, carbazole derivatives such as N-phenylcarbazole and polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di-1-naphthyl-N,N'-diphenyl-1,1'-biphenyl-4,4'diamine (NPD).

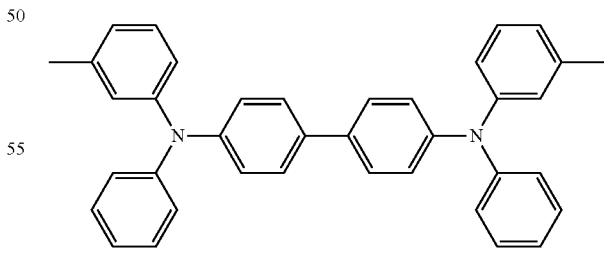

TPD

The thickness of the HTL 40 may be in the range of about 50 Å to about 2,000 Å. In some embodiments, the thickness of the HTL 40 may be in the range of about 100 Å to about 1,500 Å. When the thickness of the HTL 40 is within these ranges, satisfactory hole transport properties may be obtained without a substantial increase in driving voltage.

In addition, the functional layer having hole injection and hole transport abilities may be formed instead of the HIL and the HTL. A material for forming the functional layer having hole injection and hole transport abilities may be selected from known materials.

At least one of the HIL, the HTL, and the functional layer having hole injection and hole transport abilities may further include a charge-generating material so as to increase the conductivity of the layers, in addition to the known hole injection material, the known hole transport material and/or the material for forming the functional layer having hole injection and hole transport abilities.

The charge-generating material may be, for example, a p-dopant. Examples of the p-dopant may include, but are not limited to, quinone derivatives such as tetra-cyanoquinodimethane (TCNQ) and 2,3,5,6-tetrafluoro-tetracyano-1,4-benzoquinodimethane (F4TCNQ); metal oxides such as an tungsten oxide and a molybdenum oxide; and cyano-containing compounds such as Compound 200 below and the like.

Compound 200

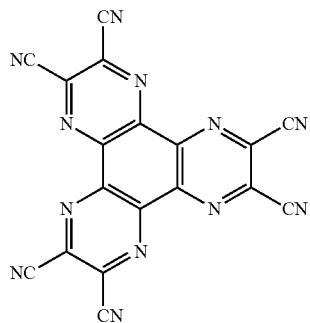

When the HIL, the HTL or the functional layer having hole injection and hole transport abilities further include the charge-generating material, the charge-generating material may be homogeneously or inhomogeneously dispersed in these layers.

The EML 50 may be formed on the HTL 40 (or the functional layer having hole injection and hole transport abilities, optionally) by vacuum deposition, spin coating, casting, or LB deposition. When the EML 50 is formed by vacuum deposition or spin coating, the deposition and coating conditions may vary according to used compounds. However, in general, the conditions may be almost the same as the conditions for forming the HIL 30.

A material for forming the EML 50 may be at least one of the condensed-cyclic compound of Formula 1 and a known light-emitting material (host and/or dopant). For example, the EML 50 may include a known host and the condensed-cyclic compound of Formula 1 as a dopant. In this regard, the condensed-cyclic compound of Formula 1 may act as a blue dopant.

Examples of the known host may include, but are not limited to, Tris(8-hydroxyquinolinato)aluminium (Alq3), 4,4'-N,N'-dicabazole-biphenyl (CBP), poly(n-vinylcabazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl)anthracene (TBADN), E3, and distyrylarylene (DSA).

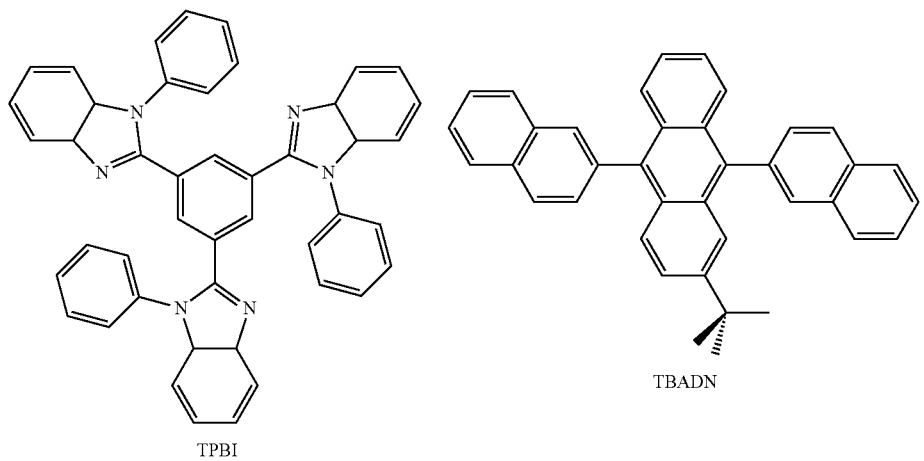

TPBI

TBADN

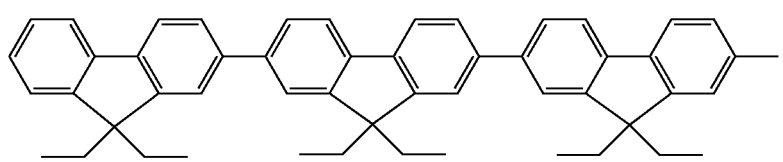

E3

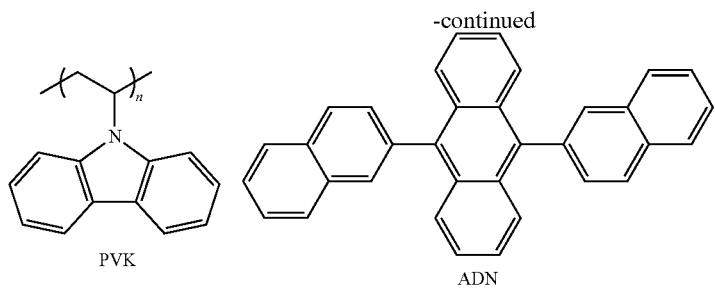

PVK

-continued

ADN

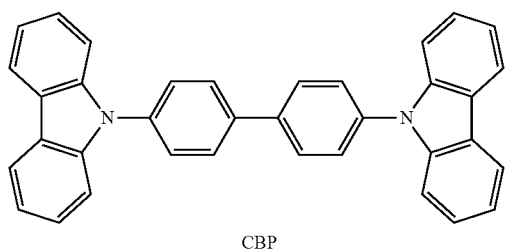

CBP

Alternatively, the host may be an anthracene-based compound represented by Formula 60 below:

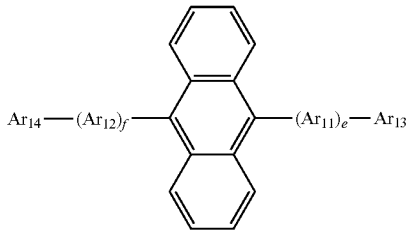

Formula 60

In Formula 60, $Ar_{11}$ and $Ar_{12}$ may be each independently a substituted or unsubstituted $C_6$-$C_{60}$ arylene group; $Ar_{13}$ and $Ar_{14}$ may be each independently a substituted or unsubstituted $C_1$-$C_{10}$ alkyl group or a substituted or unsubstituted $C_6$-$C_{60}$ aryl group; and e and f may be each independently an integer of 0 to 5.

For example, in Formula 60, $Ar_{11}$ and $Ar_{12}$ may be each independently a phenylene group; or a phenylene group that is substituted with at least one of a phenyl group, a naphthyl group, and an anthryl group, but are not limited thereto.

In Formula 60, e and f may be each independently 0, 1, or 2.

In Formula 60, $Ar_{13}$ and $Ar_{14}$ may be each independently a $C_1$-$C_{10}$ alkyl group that is substituted with at least one of a phenyl group, a naphthyl group, and an anthryl group; a phenyl group; a naphthyl group; an anthryl group; a pyrenyl group; a phenanthrenyl group; and a phenyl group, a naphthyl group, an anthryl group, a pyrenyl group, and a phenanthrenyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, but are not limited thereto.

For example, in Formula 60, $Ar_{11}$ and $Ar_{12}$ may be each independently a phenylene group; or a phenylene group that is substituted with at least one of a phenyl group, a naphthyl group, and an anthryl group; e and f may be each independently 0, 1, or 2; and $Ar_{13}$ and $Ar_{14}$ may be each independently one selected from a $C_1$-$C_{10}$ alkyl group that is substituted with at least one of a phenyl group, a naphthyl group, and an anthryl group; a phenyl group; a naphthyl group; an anthryl group; a pyrenyl group; and a phenanthrenyl group, but are not limited thereto.

For example, the anthracene-based compound of Formula 60 may be one of Compounds BH01 through BH39 below, but is not limited thereto:

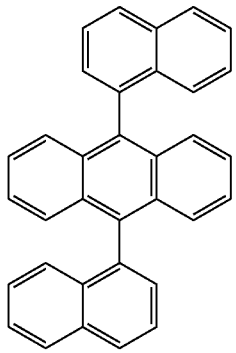

BH01

BH02
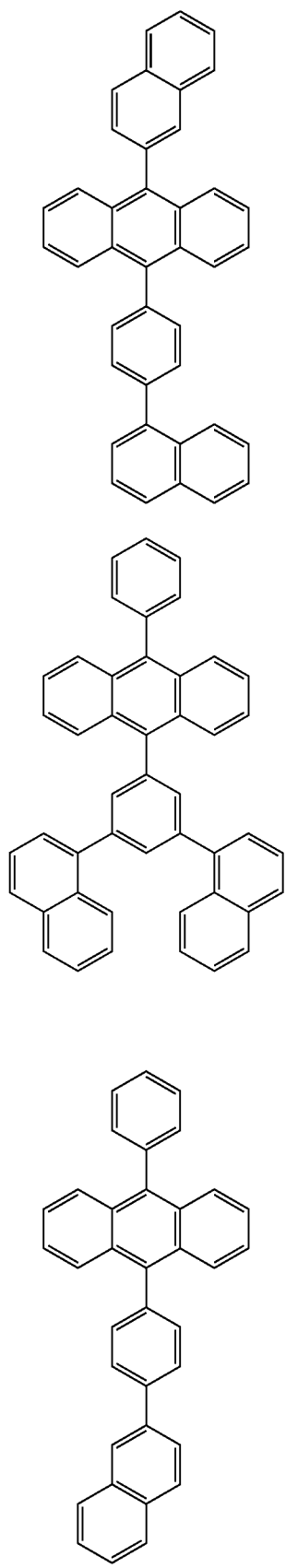
BH03
BH04
BH05
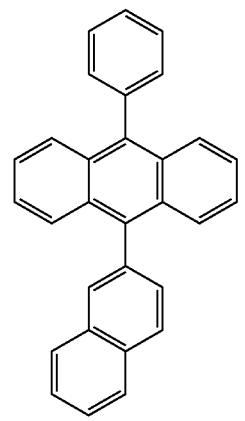
BH06
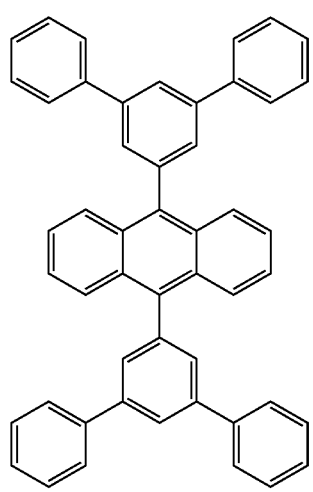
BH07
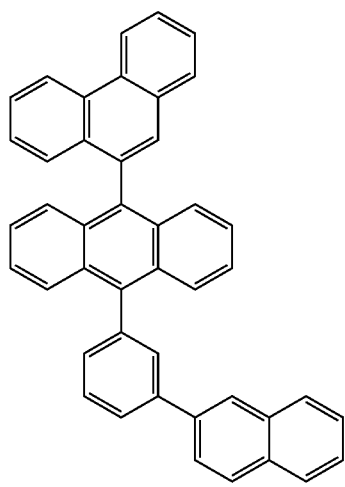

BH08
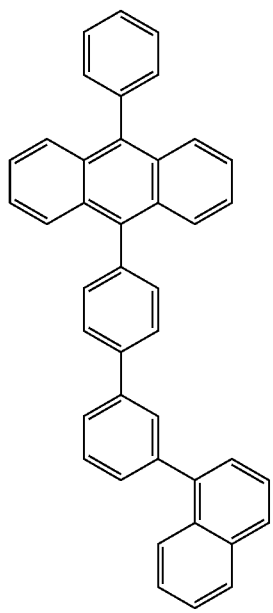
BH09
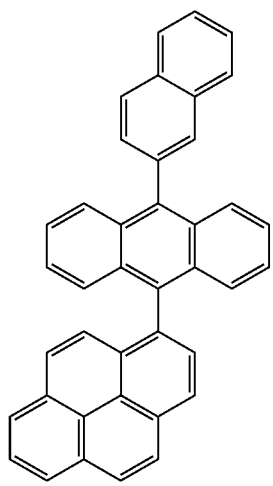
BH10
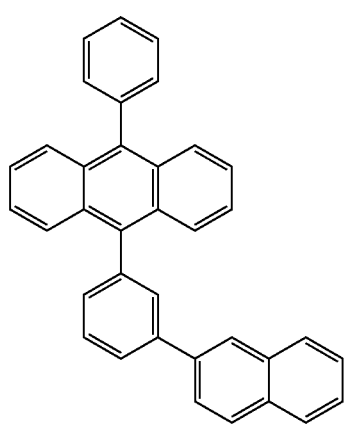
BH11
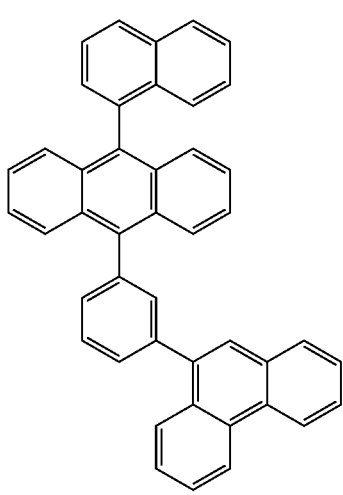
BH12
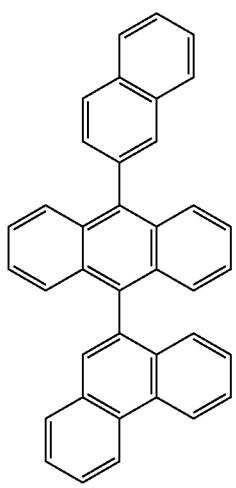
BH13
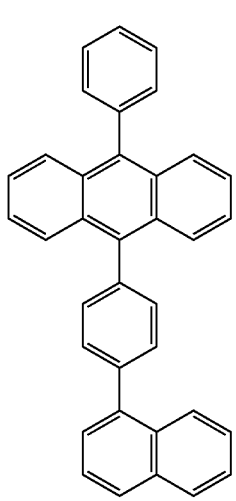

BH14
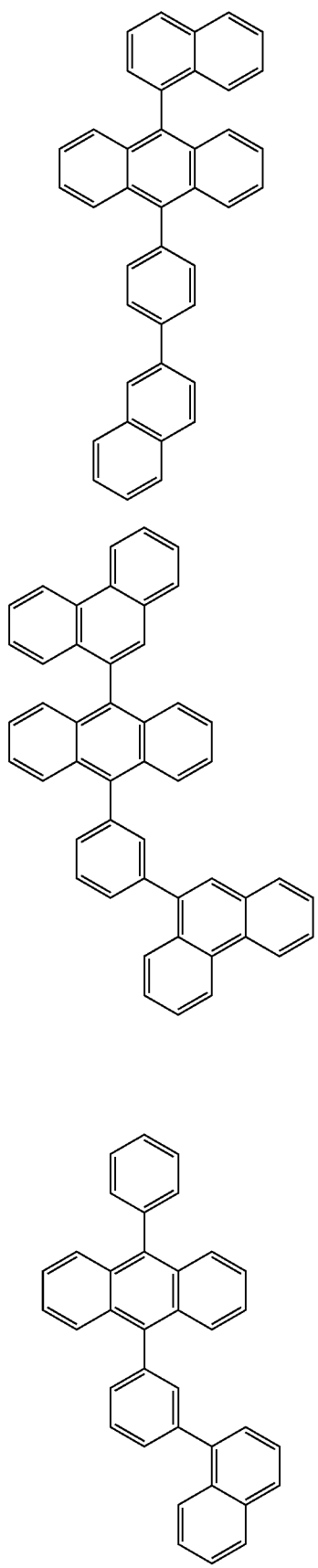
BH15
BH16
BH17
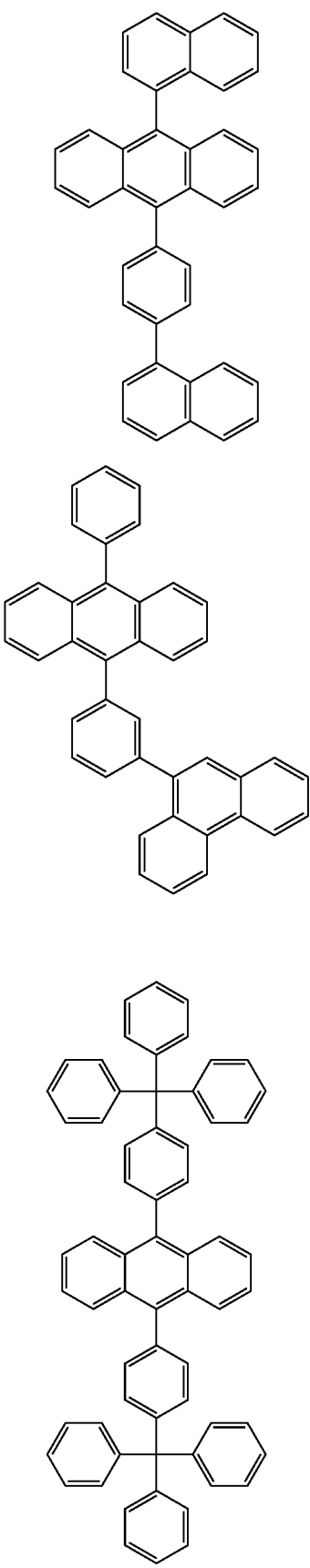
BH18
BH19

BH20
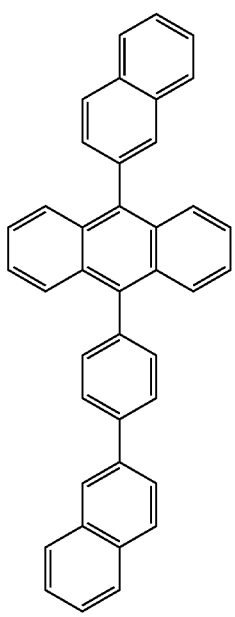
BH21
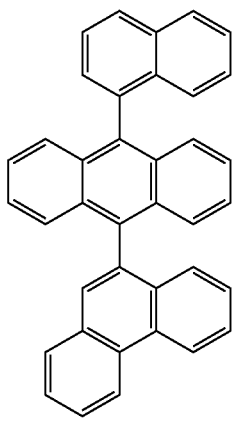
BH22
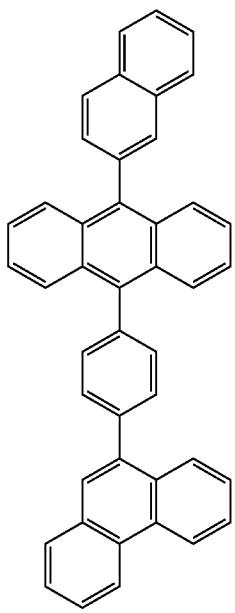
BH23
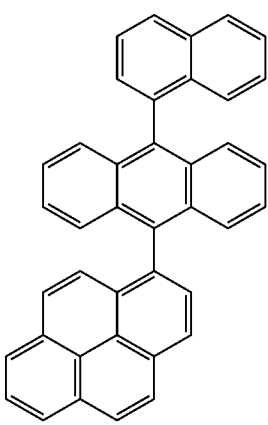
BH24
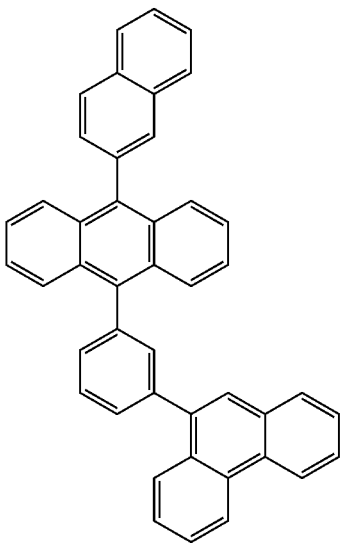
BH25
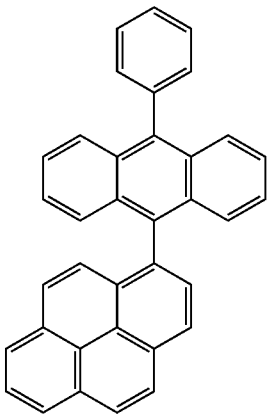

BH26
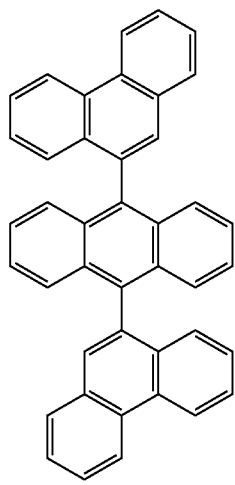
BH27
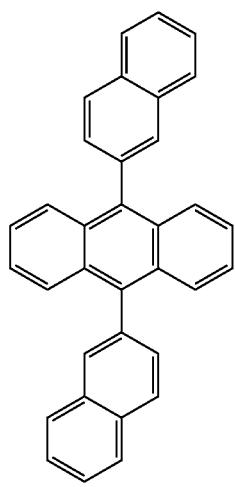
BH28
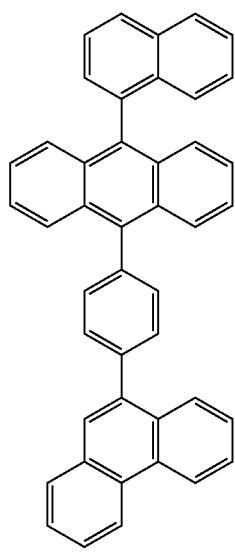
BH29
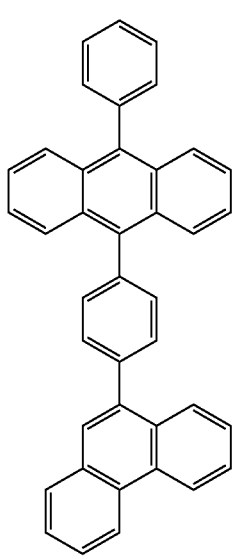
BH30
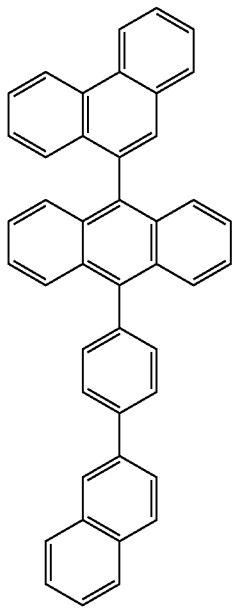

BH31
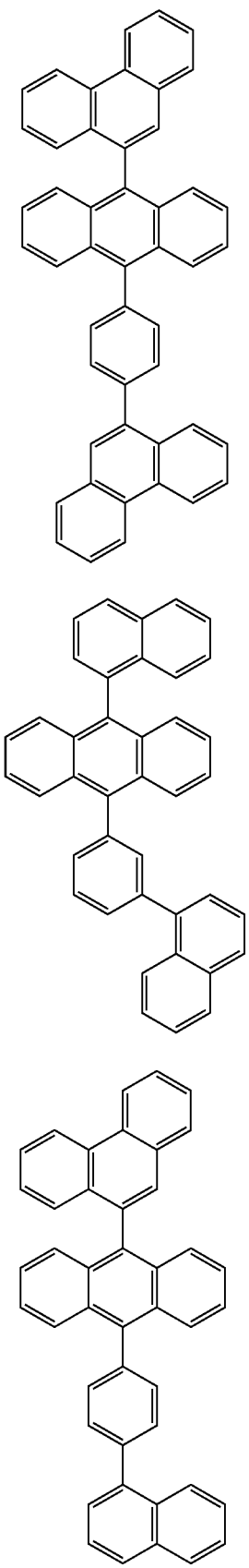
BH32
BH33
BH34
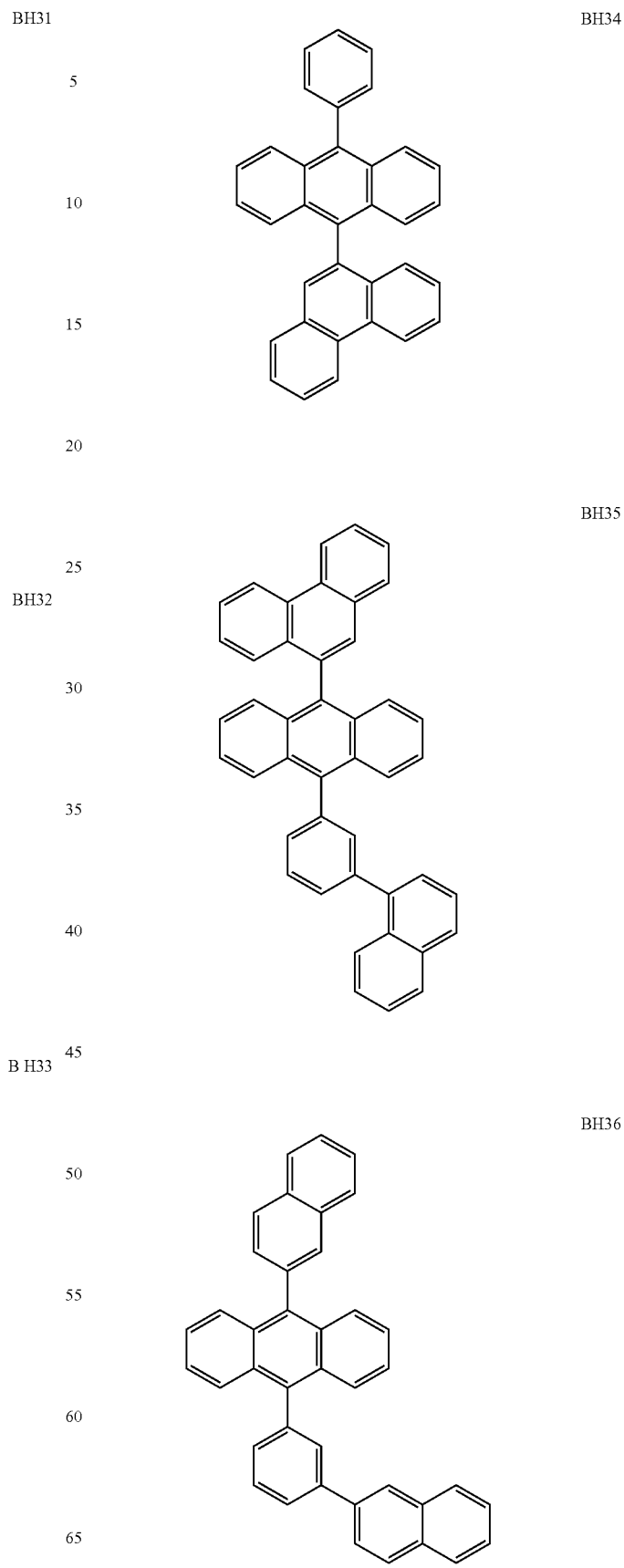
BH35
BH36

-continued

BH37

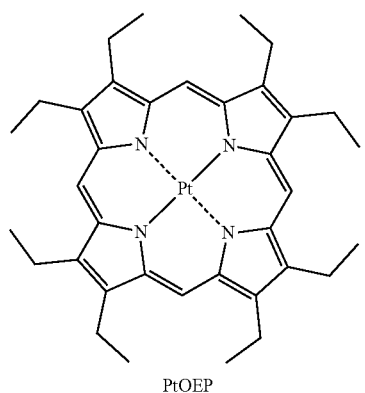

PtOEP

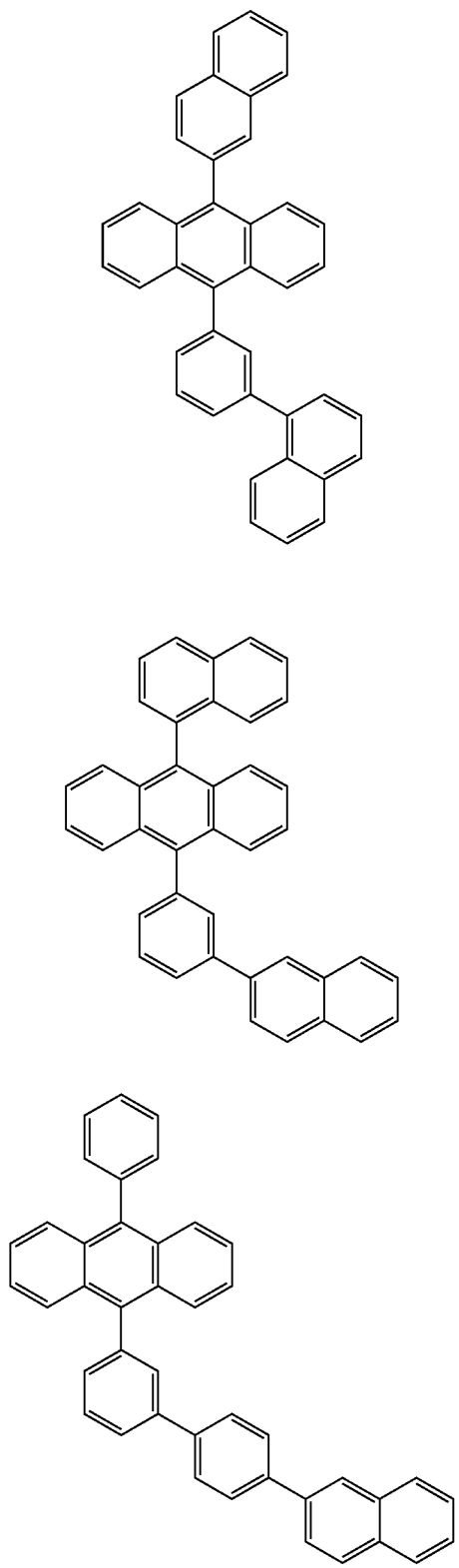

BH38

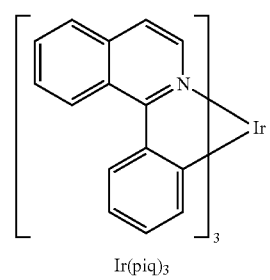

Ir(piq)₃

BH39

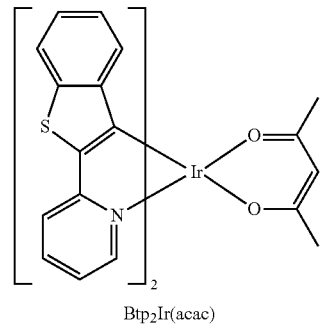

Btp₂Ir(acac)

Examples of known green dopants include, but are not limited to, Ir(ppy)₃ (ppy=phenylpyridine), Ir(ppy)₂(acac), Ir(mpyp)₃, and C545T.

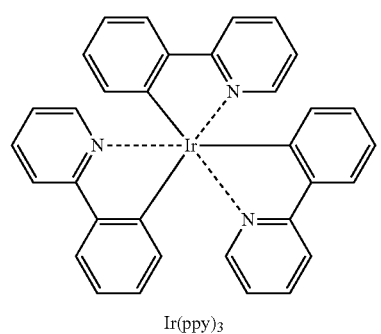

Ir(ppy)₃

Meanwhile, to manufacture a full-color OLED, a red EML and a green EML may be further patterned.

In this regard, examples of known red dopants include, but are not limited to, PtOEP, Ir(piq)₃, and Btp₂Ir(acac).

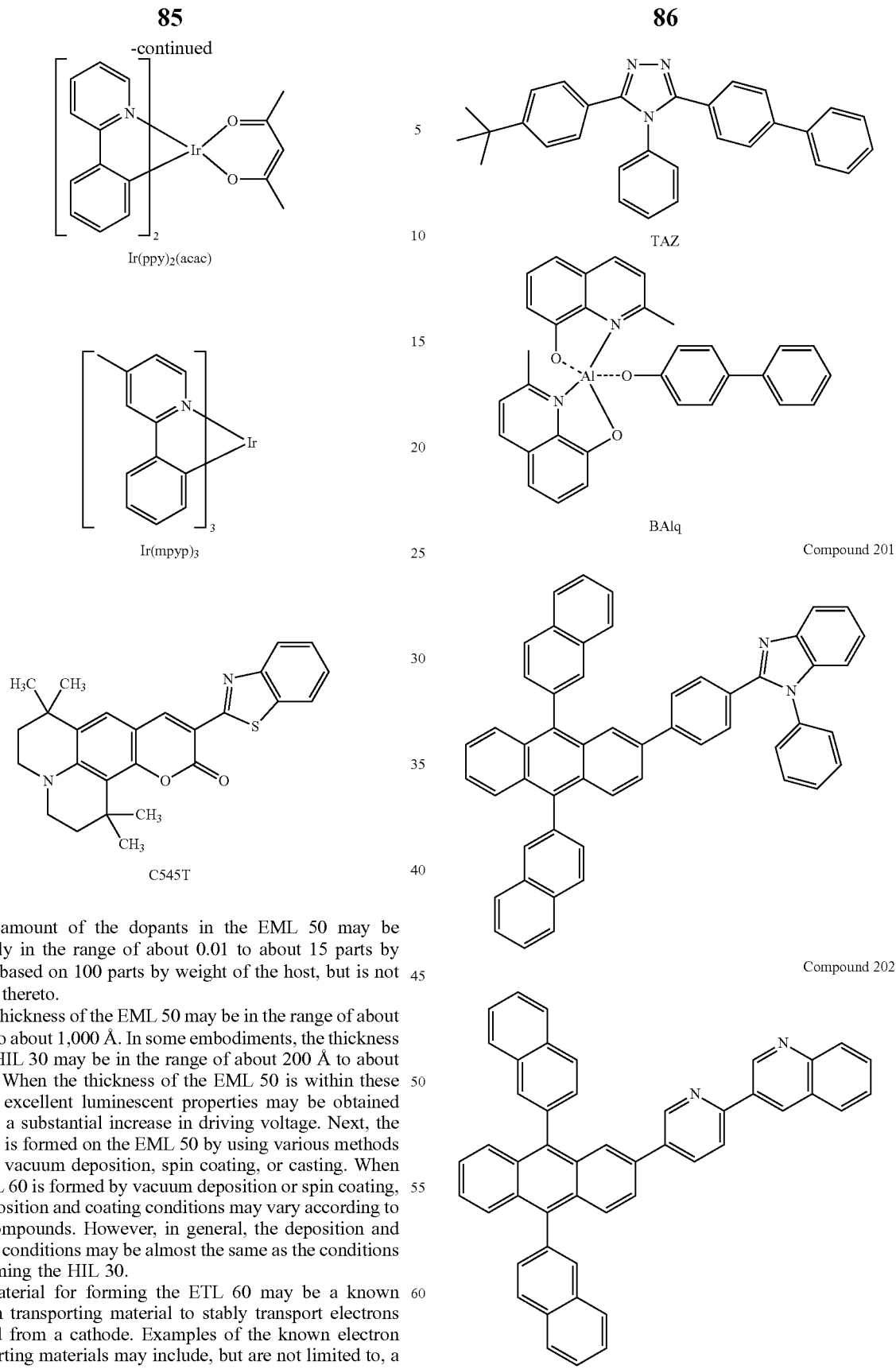

The amount of the dopants in the EML 50 may be generally in the range of about 0.01 to about 15 parts by weight based on 100 parts by weight of the host, but is not limited thereto.

The thickness of the EML 50 may be in the range of about 100 Å to about 1,000 Å. In some embodiments, the thickness of the HIL 30 may be in the range of about 200 Å to about 600 Å. When the thickness of the EML 50 is within these ranges, excellent luminescent properties may be obtained without a substantial increase in driving voltage. Next, the ETL 60 is formed on the EML 50 by using various methods such as vacuum deposition, spin coating, or casting. When the ETL 60 is formed by vacuum deposition or spin coating, the deposition and coating conditions may vary according to used compounds. However, in general, the deposition and coating conditions may be almost the same as the conditions for forming the HIL 30.

A material for forming the ETL 60 may be a known electron transporting material to stably transport electrons injected from a cathode. Examples of the known electron transporting materials may include, but are not limited to, a quinoline derivative such as tris(8-quinolinolate)aluminum ($Al_{q3}$), TAZ, Balq, beryllium bis(benzoquinolin-10-olate) ($Beb_{q2}$), AND, Compound 201 below, and Compound 202 below.

The thickness of the ETL 60 may be in the range of about 100 Å to about 1,000 Å. In some embodiment, the thickness of the ETL may be in the range of about 150 Å to about 500 Å. When the thickness of the ETL 60 is within these ranges, satisfactory electron transport properties may be obtained without a substantial increase in driving voltage.

In addition, the ETL 60 may include a known electron transporting organic compound and a metal-containing material.

The metal-containing material may include a Li-complex. Examples of the Li-complex may include lithium quinolate (LiQ) and Compound 203 below:

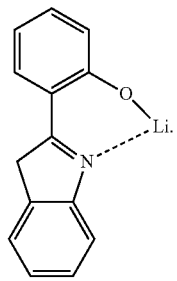

Compound 203

Also, the EIL 70, which facilitates electron injection from a cathode, may be formed on the ETL 60, and a material for forming the EIL 70 is not particularly limited.

The material for forming the EIL 70 may include a well-known material for forming an EIL, such as LiF, NaCl, CsF, $Li_2O$, or BaO. The deposition conditions of the EIL may vary according a used compound. However, in general, the conditions may be almost the same as the conditions for forming the HIL 30.

The thickness of the EIL 70 may be in the range of about 1 Å to about 100 Å. In some embodiment, the thickness of the ETL may be in the range of about 3 Å to about 90 Å. When the thickness of the EIL 70 is within these ranges, satisfactory electron injection properties may be obtained without a substantial increase in driving voltage.

The second electrode 80 is formed on the EIL 70. The second electrode 80 may be a cathode, which is an electron injection electrode. Here, a metal for forming the second electrode 80 may include a metal having low work function, such as metal, an alloy, an electric conducting compound, or a mixture thereof. In particular, the second electrode 80 may be formed as a thin film by using lithium (Li), magnesium (Mg), aluminum (Al), aluminum-lithium (Al—Li), calcium (Ca), magnesium-indium (Mg—In), or magnesium-silver (Mg—Ag), thus being transparent. In order to obtain a top-emission type OLED, the second electrode 80 may be formed as a transparent electrode by using ITO or IZO.

The OLED may be used in a display device and a monochrome or white light illumination device. The display device and the illumination device may further include at least one thin film transistor (TFT), and a first electrode of the OLED may contact one of a source electrode and a drain electrode that are included in the TFT.

An OLED according to an embodiment of the present invention will now be described in more detail with reference to the following Examples. These Examples are for illustrative purposes only and are not intended to limit the scope of the invention.

EXAMPLES

Synthesis Example 1

Synthesis of Compound 1

Synthesis Example 1-(1)

Synthesis of Intermediate 1-a

Intermediate 1-a was synthesized according to Reaction Scheme 1 below:

Reaction Scheme 1

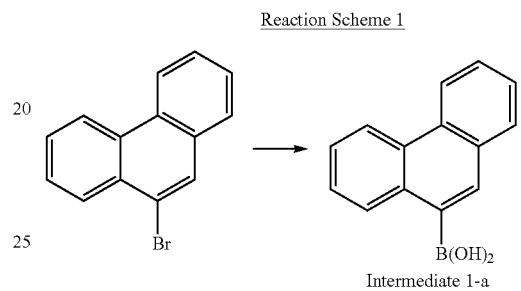

Intermediate 1-a 50 g (194 mmol) of 9-bromo phenanthrene was added to a round-bottom flask containing 500 ml of tetrahydrofuran, and a temperature of the round-bottom flask was then adjusted to be −78° C. in a nitrogen atmosphere. After 30 minutes, 146 ml (233 mmol) of normal butyl lithium was slowly dropped to the mixture, 28.3 g (274 mmol) of trimethylborate was slowly dropped thereto after 1 hour, and the temperature was raised to room temperature. The resultant mixture was stirred for about 12 hours at room temperature and 2N (normal) aqueous hydrochloric acid solution was dropped to the reaction solution until the solution becomes an acid solution, and the resultant solution was then extracted. The organic layer was separated and evaporated under reduced pressure. The residue was recrystallized with normal hexane and the resulting product was filtered and dried. As a result, 35 g of white solid Intermediate 1-a (yield: 81%) was obtained.

Synthesis Example 1-(2)

Synthesis of Intermediate 1-b

Intermediate 1-b was synthesized according to Reaction Scheme 2 below:

Reaction Scheme 2

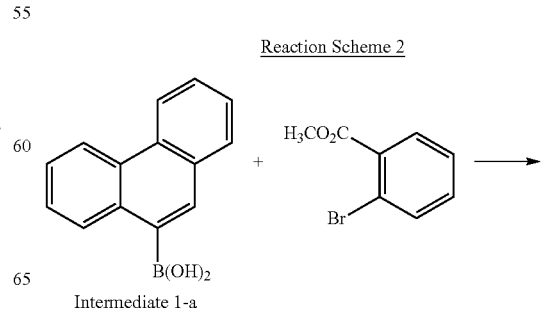

Intermediate 1-a

-continued

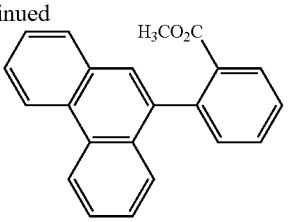

Intermediate 1-b

To a round-bottom flask was added 24 g (112 mmol) of methyl 2-bromobenzoate, 34.7 g (0.156 mmol) of Intermediate 1-a, 2.6 g (2 mmol) of tetrakistriphenylphosphinpalladium {Pd(PPh$_3$)$_4$}, 30.9 g (223 mmol) of potassium carbonate, 50 ml of water, 125 ml of toluene, and 125 ml of tetrahydrofuran and the resultant mixture was then refluxed for 12 hours. After the reaction was terminated, the reactant was subjected to a layer separation process to obtain an organic layer. The obtained organic layer was concentrated under reduced pressure, purified by column and then dried. As a result, 25 g of white solid Intermediate 1-b (yield: 72%) was obtained.

Synthesis Example 1-(3)

Synthesis of Intermediate 1-c

Intermediate 1-c was synthesized according to Reaction Scheme 3 below:

Reaction Scheme 3

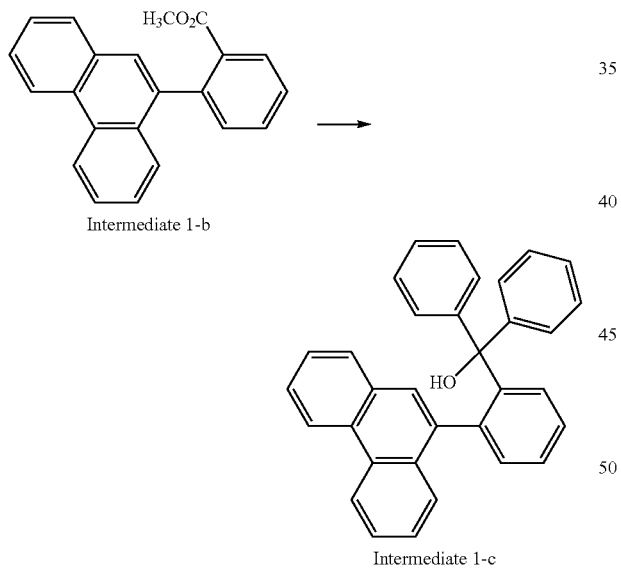

Intermediate 1-c 25 g (80 mmol) of Intermediate 1-b was added to a round-bottom flask containing 250 ml of tetrahydrofuran, and a temperature of the round-bottom flask was then reduced to −78° C. in a nitrogen atmosphere. After 30 minutes, 150 ml (240 mmol) of 1.6M phenyl lithium was slowly dropped to the mixture and the temperature was raised to room temperature after 1 hour. The resultant mixture was stirred at room temperature for about 2 hours and an aqueous ammonium chloride solution was added thereto. Thereafter, the resulting solution was extracted to obtain an organic layer and the obtained organic layer was then evaporated under reduced pressure. The residue was recrystallized with normal hexane and the resulting product was filtered and dried. As a result, 29 g of white solid Intermediate 1-c (yield: 83%) was obtained.

Synthesis Example 1-(4)

Synthesis of Intermediate 1-d

Intermediate 1-d was synthesized according to Reaction Scheme 4 below:

Reaction Scheme 4

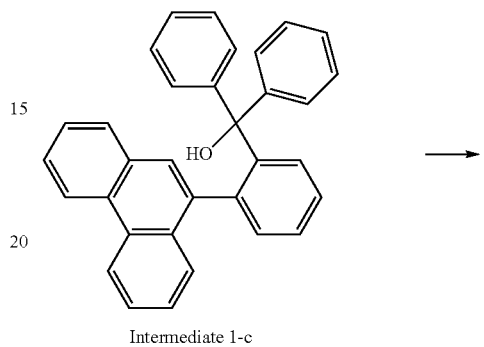

Intermediate 1-c

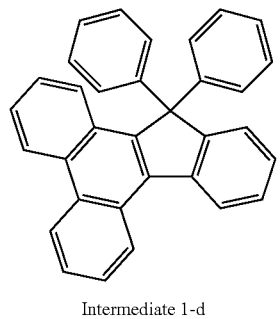

Intermediate 1-d 29 g (66 mmol) of Intermediate 1-c was added to a round-bottom flask containing 290 ml of acetic acid. Subsequently, a temperature of the round-bottom flask was raised to 80° C. and 1 to 2 droplets of an aqueous hydrochloric acid solution was added thereto, and the resultant solution was refluxed for about 2 hours and the temperature was adjusted to room temperature. The solid produced therefrom was filtered and dried. As a result, 27 g of white solid Intermediate 1-d (yield: 93%) was obtained.

Synthesis Example 1-(5)

Synthesis of Intermediate 1-e

Intermediate 1-e was synthesized according to Reaction Scheme 5 below:

Reaction Scheme 5

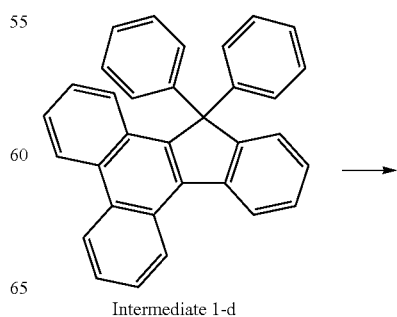

Intermediate 1-d

-continued

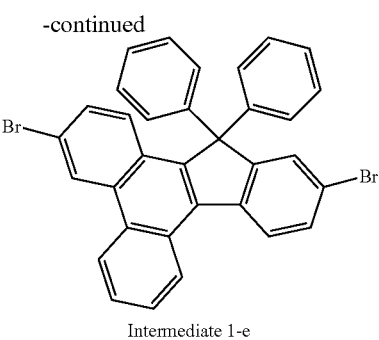

Intermediate 1-e 27 g (65 mmol) of Intermediate 1-d was added to a round-bottom flask containing 216 ml of chloroform and the mixture was stirred. Subsequently, 28.9 g (181 mmol) of bromine was diluted with 54 ml of chloroform, the diluted mixture was slowly dropped to the stirred mixture, and the resultant mixture was stirred at room temperature for 48 hours. Thereafter, solid produced therefrom was filtered and dried. As a result, 27 g of white solid Intermediate 1-e (yield: 93%) was obtained.

Synthesis Example 1-(6)

Synthesis of Compound 1

Compound 1 was synthesized according to Reaction Scheme 7 below:

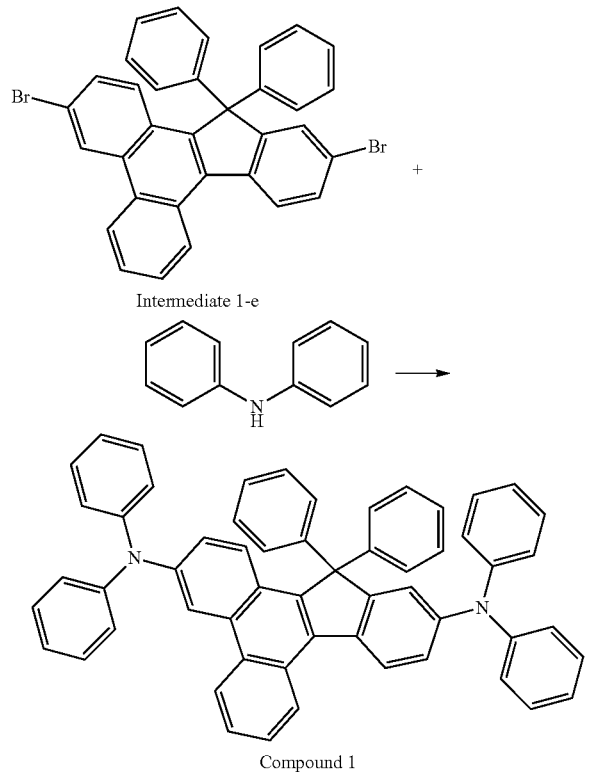

Reaction Scheme 7

Compound 1

To a round-bottom flask were added 10 g (17 mmol) of Intermediate 1-e, 7.6 g (45 mmol) of diphenyl amine, 0.2 g (0.7 mmol) of palladium acetate {Pd(OAc)$_2$}, 6.7 g (69 mmol) of sodium tertiary butoxide, 0.14 g (0.7 mmol) of tri-tertiary butylphosphine, and 100 ml of toluene and the mixture was maintained at a reaction temperature of 100° C. for 2 hours to induce a reaction therebetween. After the reaction was terminated, the reaction solution was filtered, the filtrate was concentrated, and the resulting filtrate was purified by column chromatography. Thereafter, the resulting product was recrystallized with toluene and methanol and solid produced therefrom was filtered and dried. As a result, 5.7 g of Compound 1 was obtained as a pale yellow solid (yield: 40%).

The produced compound was identified using NMR.

MS: m/z 752 [M]$^+$ $^1$H NMR (CDCl$_3$) δ 8.89 (d, 1H), 8.47 (d, 1H), 8.40 (s, 1H), 8.24 (d, 1H), 7.73 (t, 1H), 7.63 (m, 2H), 7.27 (m, 23H), 7.01 (m, 10H)

Synthesis Example 2

Synthesis of Compound 3

Synthesis Example 2-(1)

Synthesis of Intermediate 2-a

Intermediate 2-a was synthesized according to Reaction Scheme 8 below:

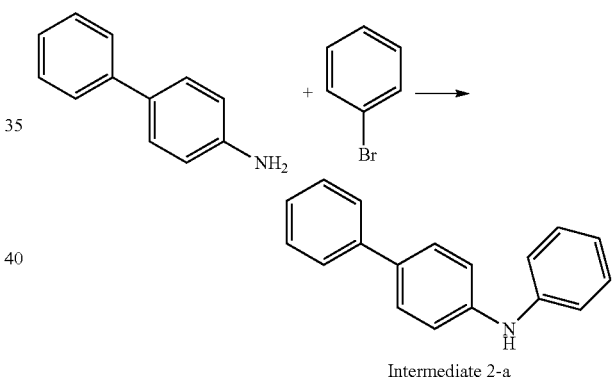

Reaction Scheme 8

Intermediate 2-a

To a round-bottom flask were added 16.3 g (96 mmol) of 4-amino biphenyl, 15.8 g (101 mmol) of bromobenzene, 0.32 g (1.4 mmol) of palladium acetate, 0.9 g (1.4 mmol) of 2,2-bis(diphenylphosphino)-1,1'-binaphthyl, 18.5 g (193 mmol) of sodium tertiary butoxide, and 160 ml of toluene and the mixture was refluxed for 24 hours. After the temperature was adjusted to be room temperature, the mixture was filtered, the filtrate was concentrated, and the resulting filtrate was purified by column chromatography. Thereafter, the resulting product was recrystallized with dichloromethane and methanol and solid produced therefrom was filtered and dried. As a result, 15 g of white solid Intermediate 2-a was obtained (yield: 60%).

Synthesis Example 2-(2)

Synthesis of Compound 3

3.7 g of Compound 3 was obtained as a pale yellow solid (yield: 31%) in the same manner as in Synthesis Example 1-(6), except that Intermediate 2-a was used instead of diphenyl amine.

The produced compound was identified using NMR.
MS: m/z 904 [M]+
1H NMR (CDCl3) δ 8.90 (d, 1H), 8.51 (m, 2H), 8.27 (d, 1H), 7.75 (t, 2H), 7.61 (m, 6H), 7.48 (m, 9H), 7.36 (m, 9H), 7.23 (m, 11H), 7.12 (m, 7H)

Synthesis Example 3

Synthesis of Compound 9

4.7 g of Compound 9 was obtained as a pale yellow solid (yield: 39%) in the same manner as in Synthesis Example 2, except that, in Synthesis Example 2-(1), 4-tertiary-butylaniline was used instead of 4-amino biphenyl and 1-bromo-4-tertiary-butylbenzene was used instead of bromobenzene.
The produced compound was identified using NMR.
MS: m/z 977 [M]+
1H NMR (CDCl3) δ 8.89 (s, 1H), 8.49 (d, 1H), 8.23 (s, 1H), 7.68 (m, 3H), 7.31 (m, 21H), 7.05 (m, 9H), 1.38 (s, 18H), 1.37 (s, 18H)

Synthesis Example 4

Synthesis of Compound 10

2.7 g of Compound 10 was obtained as a pale yellow solid (yield: 24%) in the same manner as in Synthesis Example 2, except that, in Synthesis Example 2-(1), 4-tertiary-butylaniline was used instead of 4-amino biphenyl and bromobenzene-$d_5$ was used instead of bromobenzene.
The produced compound was identified using NMR.
MS: m/z 875 [M]+
1H NMR (CDCl3) δ 8.91 (d, 1H), 8.45 (m, 2H), 8.26 (d, 1H), 7.67 (m, 3H), 7.30 (m, 15H), 7.07 (m, 6H)

Synthesis Example 5

Synthesis of Compound 11

6.4 g of Compound 11 was obtained as a pale yellow solid (yield: 67%) in the same manner as in Synthesis Example 2, except that, in Synthesis Example 2-(1), 4-tertiary-butylaniline was used instead of 4-amino biphenyl and 1-bromo-4-(trimethylsilyl)benzene was used instead of bromobenzene.
The produced compound was identified using NMR.
MS: m/z 1009 [M]+
1H NMR (CDCl3) δ 8.88 (d, 1H), 8.51 (d, 1H), 8.43 (S, 1H), 8.24 (d, 1H), 7.73 (t, 1H), 7.64 (m, 2H), 7.21 (m, 29H), 1.36 (s, 9H), 1.35 (S, 9H), 0.30 (s, 9H), 0.29 (s, 9H)

Synthesis Example 6

Synthesis of Compound 12

5.1 g of Compound 12 was obtained as a pale yellow solid (yield: 49%) in the same manner as in Synthesis Example 2, except that 1-bromo-4-tertiary-butylbenzene was used instead of bromobenzene in Synthesis Example 2-(1).
The produced compound was identified using NMR.
MS: m/z 1017 [M]+
1H NMR (CDCl3) δ 8.93 (s, 1H), 8.50 (m, 2H), 8.29 (d, 1H), 7.40 (m, 42H), 1.41 (s, 9H), 1.40 (s, 9H)

Synthesis Example 7

Synthesis of Compound 28

3.3 g of Compound 28 was obtained as a pale yellow solid (yield: 38%) in the same manner as in Synthesis Example 1, except that methyl magnesium bromide was used instead of phenyl lithium in Synthesis Example 1-(3).
The produced compound was identified using NMR.
MS: m/z 628 [M]+
1H NMR (CDCl3) δ 8.84 (s, 1H), 8.53 (m, 2H), 8.26 (s, 2H), 7.42 (m, 25H), 1.75 (s, 6H)

Synthesis Example 8

Synthesis of Compound 29

3.3 g of Compound 29 was obtained as a pale yellow solid (yield: 38%) in the same manner as in Synthesis Example 1, except that methyl magnesium bromide was used instead of phenyl lithium in Synthesis Example 1-(3) and Intermediate 2-a was used instead of diphenyl amine in Synthesis Example 1-(6).
The produced compound was identified using NMR.
MS: m/z 780 [M]+
1H NMR (CDCl3) δ 8.85 (s, 1H), 8.55 (m, 2H), 8.28 (s, 2H), 7.47 (m, 33H), 1.76 (s, 6H)

Synthesis Example 9

Synthesis of Compound 14

Synthesis Example 9-(1)

Synthesis of Intermediate 9-a

Intermediate 9-a was synthesized according to Reaction Scheme 9 below:

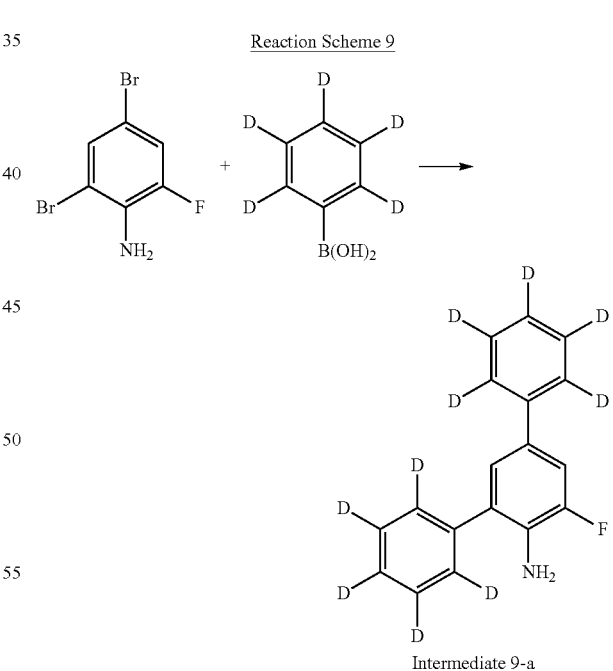

To a 1 L round-bottom flask were added 30 g (111.56 mmol) of 2,4-dibromo-6-fluoroaniline, 31.2 g (245.44 mmol) of phenylboronic acid-$d_5$, 61.9 g (446.27 mmol) of potassium carbonate, 2.6 g (2.20 mmol) of tetrakistriphenylphosphinpalladium, 120 ml of water, 300 ml of toluene, and 300 ml of tetrahydrofuran and the mixture was maintained at a reaction temperature of 80° C. for 24 hours to induce a reaction therebetween. After the reaction was terminated, the reaction product was subjected to a layer separation process to remove a water layer and separate an organic layer therefrom, and the obtained organic layer was concentrated under reduced pressure. The resulting product was purified by column chromatography by using hexane and dichloromethane and solid produced therefrom was dried. As a result, 24.2 g of white solid Intermediate 9-a was obtained (yield: 79.4%).

Synthesis Example 9-(2)

Synthesis of Intermediate 9-b

Intermediate 9-b was synthesized according to Reaction Scheme 10 below:

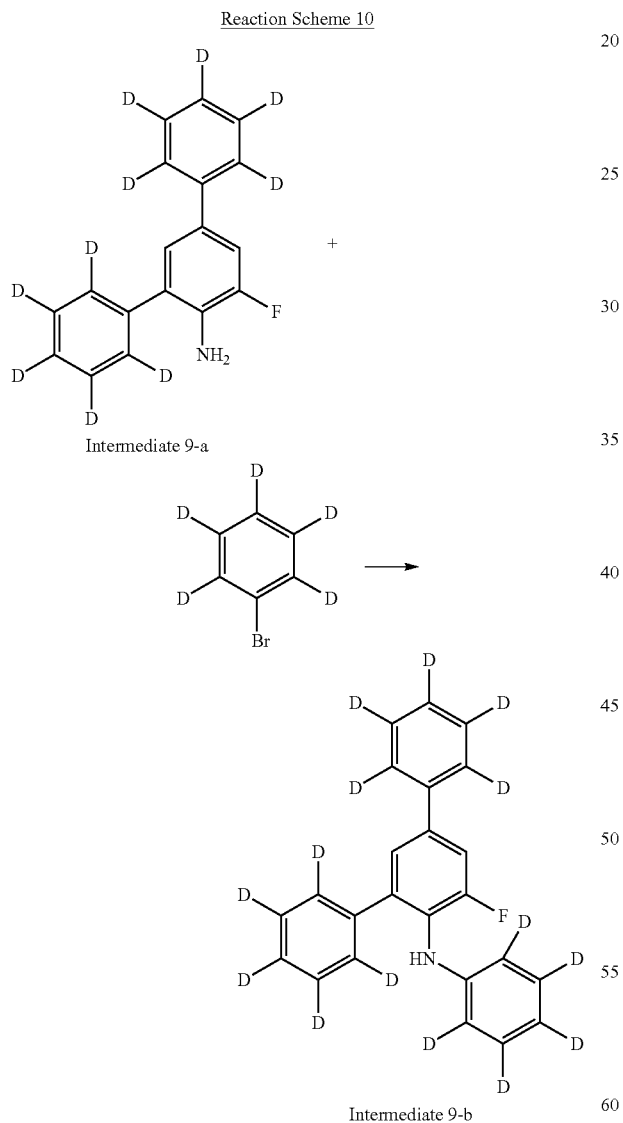

Intermediate 9-b

To a round-bottom flask were added 15 g (55 mmol) of Intermediate 9-a, 8.9 g (55 mmol) of bromobenzene-$d_5$, 0.25 g (1.1 mmol) of palladium acetate, 0.68 g (1.1 mmol) of 2,2-bis(diphenylphosphino)-1,1'-binaphthyl, 10.6 g (110 mmol) of sodium tertiary butoxide, and 150 ml of toluene and the mixture was refluxed for 24 hours. The resultant mixture was filtered, the filtrate was concentrated, and the resulting filtrate was purified by column chromatography. Thereafter, the resulting product was recrystallized with dichloromethane and methanol and solid produced therefrom was filtered and dried. As a result, 14 g of white solid Intermediate 9-b was obtained (yield: 72%).

Synthesis Example 9-(3)

Synthesis of Compound 14

3.1 g of Compound 14 was obtained as a pale yellow solid (yield: 24%) in the same manner as in Synthesis Example 1, except that Intermediate 9-b was used instead of diphenyl amine in Synthesis Example 1-(6).

The produced compound was identified using NMR.
MS: m/z 1123 [M]$^+$
$^1$H NMR (CDCl$_3$) δ 8.81 (s, 1H), 8.35 (d, 1H), 8.05 (s, 2H), 7.71 (t, 2H), 7.34 (m, 16H), 6.84 (d, 2H)

Synthesis Example 10

Synthesis of Compound 17

4.3 g of Compound 17 was obtained as a pale yellow solid (yield: 42%) in the same manner as in Synthesis Example 2, except that 4-cyanoaniline was used instead of 4-amino biphenyl in Synthesis Example 2-(1).

The produced compound was identified using NMR.
MS: m/z 803 [M]$^+$
$^1$H NMR (CDCl$_3$) δ 8.90 (d, 1H), 8.51 (m, 2H), 8.33 (d, 1H), 7.74 (m, 3H), 7.25 (m, 29H), 6.93 (d, 2H)

Synthesis Example 11

Synthesis of Compound 22

Synthesis Example 11-(1)

Synthesis of Intermediate 11-a

Intermediate 11-a was synthesized according to Reaction Scheme 11 below:

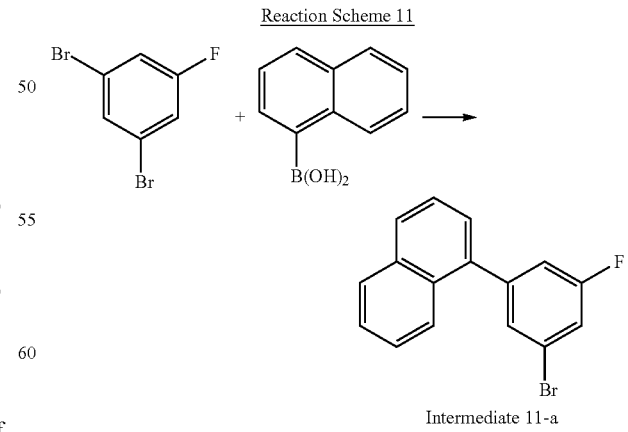

Intermediate 11-a

To a reactor were added 50 g (197 mmol) of 1,3-dibromo-5-fluorobenzene, 28.8 g (167 mmol) of 1-naphthyl boronic acid, 4.6 g (3.9 mmol) of tetrakistriphenylphosphinpalladium, 54.4 g (394 mmol) of potassium carbonate, 450 ml of toluene, and 150 ml of water and the mixture was refluxed. After the reaction was terminated, the resultant mixture was extracted to separate an organic layer. Thereafter, the organic layer was evaporated under reduced pressure and purified by column chromatography. As a result, 25 g of Intermediate 11-a was obtained in a transparent liquid state (yield: 42%).

Synthesis Example 11-(2)

Synthesis of Intermediate 11-b

Intermediate 11-b was synthesized according to Reaction Scheme 12 below:

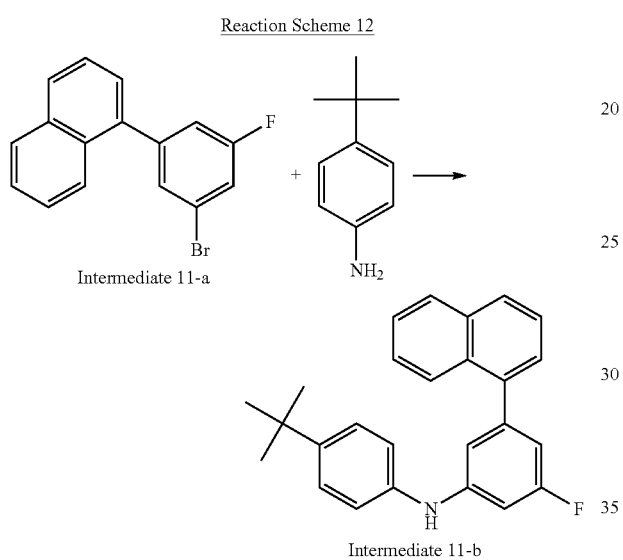

Reaction Scheme 12

Intermediate 11-a

Intermediate 11-b

Intermediate 11-b was synthesized in the same manner as in Synthesis Example 2-(1), except that 4-tert-butylaniline was used instead of 4-amino biphenyl and Intermediate 11-a was used instead of bromobenzene.

Synthesis Example 11-(3)

Synthesis of Compound 22

1.6 g of Compound 22 was obtained as a pale yellow solid (yield: 21%) in the same manner as in Synthesis Example 1, except that Intermediate 11-b was used instead of diphenyl amine in Synthesis Example 1-(6).
The produced compound was identified using NMR.
MS: m/z 1153 [M]$^+$
$^1$H NMR (CDCl$_3$) δ 8.88 (d, 1H), 8.56 (m, 2H), 8.28 (d, 1H), 7.88 (m, 6H), 7.71 (m, 3H), 7.30 (m, 30H), 6.86 (m, 5H), 1.35 (s, 9H), 1.34 (s, 9H)

Synthesis Example 12

Synthesis of Compound 26

2.7 g of Compound 26 was obtained as a pale yellow solid (yield: 36%) in the same manner as in Synthesis Example 1, except that 9,9-dimethyl-N-phenyl-9H-fluoren-2-amine was used instead of diphenyl amine in Synthesis Example 1-(6).
The produced compound was identified using NMR.
MS: m/z 985 [M]$^+$ $^1$H NMR (CDCl$_3$) δ 8.89 (s, 1H), 8.37 (m, 3H), 7.64 (m, 7H), 7.24 (m, 33H), 1.42 (s, 6H), 1.36 (s, 6H)

Synthesis Example 13

Synthesis of Compound 54

3.3 g of Compound 54 was obtained as a pale yellow solid (yield: 37%) in the same manner as in Synthesis Example 2, except that 2-bromo-9,9-dimethyl-9H-fluorene was used instead of bromobenzene in Synthesis Example 2-(1).
The produced compound was identified using NMR.
MS: m/z 1013 [M]$^+$
$^1$H NMR (CDCl$_3$) δ 8.86 (s, 1H), 8.50 (d, 1H), 8.30 (s, 2H), 7.53 (m, 39H), 1.76 (s, 6H), 1.49 (s, 12H)

Synthesis Example 14

Synthesis of Compound 64

Synthesis Example 14-(1)

Synthesis of Intermediate 14-a

Intermediate 14-a was synthesized according to Reaction Scheme 13 below:

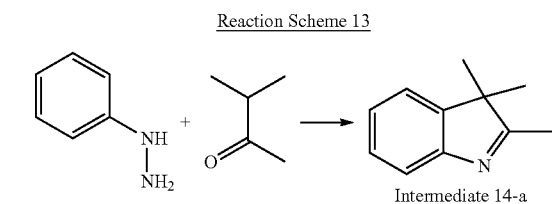

Reaction Scheme 13

Intermediate 14-a

To a reactor were added 500 ml of acetic acid and 120 g (1.39 mol) of 3-methyl-2-butanone and the temperature was raised to 60° C. Subsequently, 150 g (1.39 mol) of phenylhyrazine was slowly added to the mixture and the resultant mixture was refluxed. After the reaction was terminated, 500 ml of water was added to the mixture and the mixture was neutralized with sodium hydroxide. The resultant mixture was extracted several times with ethyl acetate and the obtained organic layer was evaporated under reduced pressure and the residue was purified by column chromatography. As a result, 156 g of Intermediate 14-a was obtained (yield: 71%).

Synthesis Example 14-(2)

Synthesis of Intermediate 14-b

Intermediate 14-b was synthesized according to Reaction Scheme 14 below:

←Reaction Scheme 14→

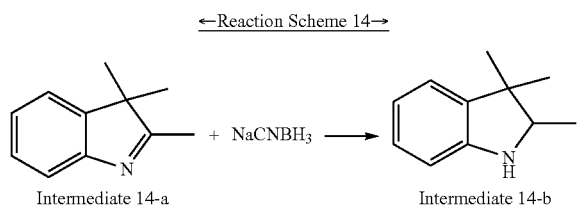

Intermediate 14-a

Intermediate 14-b 100 g (0.628 mol) of Intermediate 14-a and 500 ml of acetic acid were added to a reactor. Subsequently, 118 g (1.88 mol) of sodium cyanoborohydride was slowly added to the mixture so as not to incur severe heat generation. The resultant mixture was stirred for 5 hours, 300 ml of water was added thereto, and the mixed solution was made basic with sodium hydroxide. Thereafter, ethyl acetate was added to the resultant solution, the solution was extracted several times to separate an organic layer, and the obtained organic layer was concentrated. The resulting product was then purified by column chromatography. As a result, 55 g of Intermediate 14-b was obtained (yield: 54%).

Synthesis Example 14-(3)

Synthesis of Compound 64

1.8 g of Compound 64 was obtained as a pale yellow solid (yield: 34%) in the same manner as in Synthesis Example 1, except that Intermediate 14-b was used instead of diphenyl amine in Synthesis Example 1-(6).

The produced compound was identified using NMR.
MS: m/z 737 [M]$^+$
$^1$H NMR (CDCl$_3$) δ 8.90 (s, 1H), 8.76 (d, 1H), 8.57 (s, 1H), 8.43 (d, 1H), 7.78 (m, 3H), 7.16 (m, 21H), 4.01 (s, 1H), 3.83 (s, 1H), 1.37 (s, 3H), 1.35 (s, 3H), 1.26 (m, 6H), 1.14 (m, 6H)

Synthesis Example 15

Synthesis of Compound 68

Synthesis Example 15-(1)

Synthesis of Intermediate 15-a

Intermediate 15-a was synthesized according to Reaction Scheme 15 below:

Reaction Scheme 15

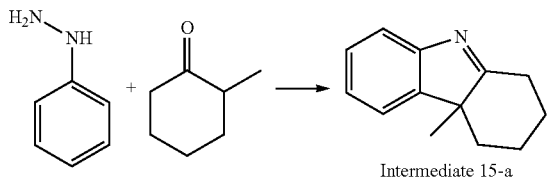

Intermediate 15-a

To a 500 ml round-bottom flask were added 50 g (0.462 mol) of phenylhydrazine and 170 ml of acetic acid and a temperature of the flask was raised to 60° C. Subsequently, 51.9 g (0.462 mol) of 2-methylcyclohexanone was added to the heated round-bottom flask. After the addition of the compound was terminated, the mixture was refluxed for 8 hours. After the reaction was terminated, 100 ml of water was added to the mixture and the resultant mixture was made basic with sodium hydroxide.

The resulting solution was extracted with water and ethyl acetate to separate an organic layer. The obtained organic layer was subjected to anhydrous treatment with magnesium sulfate and concentrated under reduced pressure. Thereafter, the resulting product was purified by column chromatograph by using hexane and ethyl acetate as a developing solvent. As a result, 72 g of Intermediate 15-a was obtained (yield: 84%).

Synthesis Example 15-(2)

Synthesis of Intermediate 15-b

Intermediate 15-b was synthesized according to Reaction Scheme 16 below:

Reaction Scheme 16

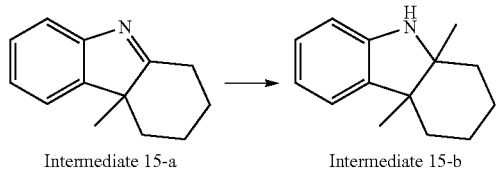

Intermediate 15-a        Intermediate 15-b 57 g (0.308 mol) of Intermediate 15-a obtained according to Reaction Scheme 15 was dissolved in 570 ml of toluene in a 2 L round-bottom flask with a nitrogen atmosphere, and the temperature was then reduced to −10° C. Subsequently, 300 ml (0.474 mol) of 1.6M methyllithium was slowly added to the solution and maintained at −10° C. for 3 hours to induce a reaction therebetween. After the reaction was terminated, water was slowly added to the reaction solution until the solution had no reactivity.

The resulting solution was extracted with water and ethyl acetate to separate an organic layer. The obtained organic layer was subjected to anhydrous treatment with magnesium sulfate and concentrated under reduced pressure. Thereafter, the resulting product was purified by column chromatograph by using hexane and ethyl acetate as a developing solvent. As a result, 47 g of Intermediate 15-b was obtained (yield: 76%).

Synthesis Example 15-(3)

Synthesis of Intermediate 15-c

Intermediate 15-b was synthesized according to Reaction Scheme 17 below:

Reaction Scheme 17

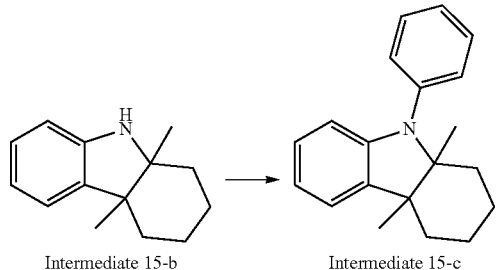

Intermediate 15-b        Intermediate 15-c

To a 1 L round-bottom flask were added 40 g (0.199 mol) of Intermediate 15-b obtained according to Reaction Scheme 16, 48.6 g (0.238 mol) of iodobenzene, 0.89 g (0.004 mol) of tris(dibenzylideneacetone)dipalladium(0), 2.47 g (0.004 mol) of 2,2-bis(diphenylphosphino)-1,1'-binaphthyl, 38.19 g (0.397 mol) of sodium tertiarybutoxide, and 400 ml of toluene and the mixture was refluxed for 8 hours. After the reaction was terminated, the resulting mixture was filtered with celite, and the filtrate was concentrated under reduced pressure. The resulting product was purified by column chromatography using hexane as a developing solvent. As a result, 44 g of Intermediate 15-c was obtained (yield: 79%).

Synthesis Example 15-(4)

Synthesis of Intermediate 15-d

Intermediate 15-d was synthesized according to Reaction Scheme 18 below:

Reaction Scheme 18

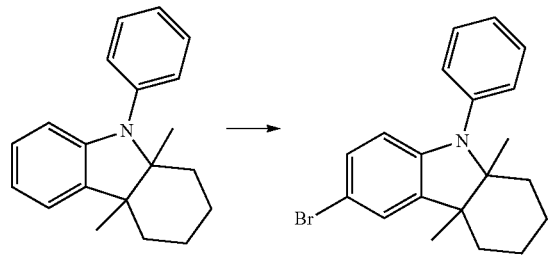

Intermediate 15-c Intermediate 15-d

To a 500 ml round-bottom flask were added 44 g (0.158 mol) of Intermediate 15-c obtained according to Reaction Scheme 17 and 130 ml of dimethylformamide and the temperature was reduced to 0° C. Subsequently, 25.2 g (0.142 mol) of N-bromosuccinimide was dissolved in 200 ml of dimethylformamide and the solution was slowly added to the mixture. After the addition of the solution was terminated, the temperature was raised to room temperature and the resulting solution was stirred for 2 hours.

After the reaction was terminated, the resultant solution was extracted with water and dichloromethane to separate an organic layer. The obtained organic layer was subjected to anhydrous treatment with magnesium sulfate and concentrated under reduced pressure. Thereafter, the resulting product was crystallized with hexane and crystal produced therefrom was filtered. As a result, 45 g of Intermediate 15-d was obtained (yield: 80%).

Synthesis Example 15-(5)

Synthesis of Intermediate 15-e

Intermediate 15-e was synthesized according to Reaction Scheme 19 below:

Reaction Scheme 19

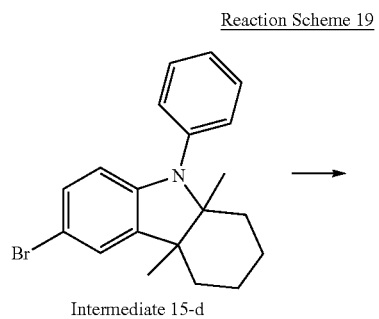

Intermediate 15-d

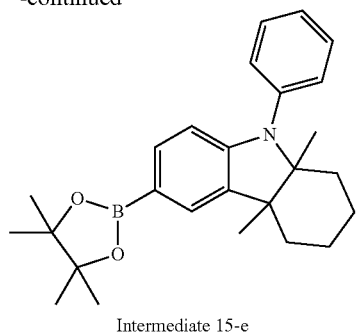

Intermediate 15-e

To a 1 L round-bottom flask were added 40 g (0.112 mol) of Intermediate 15-d obtained according to Reaction Scheme 18, 34 g (0.134 mol) of bis(pinacolato)diboron, 2.73 g (0.003 mol) of palladium(II) chloride-1-,1'-bis(diphenylphosphino)ferrocene, 32.9 g (0.335 mol) of potassium acetate, and 480 ml of toluene and the mixture was refluxed for 8 hours. After the reaction was terminated, the resultant mixture was filtered with celite and the filtrate was concentrated under reduced pressure. Thereafter, the resulting product was purified by column chromatography by using hexane and ethyl acetate as a developing solvent. As a result, 26 g of Intermediate 15-e was obtained (yield: 58%).

Synthesis Example 15-(6)

Synthesis of Compound 68

To a round-bottom flask were added 5.0 g (9 mmol) of Intermediate 15-e, 8.4 g (2.1 mmol) of Intermediate 1-e, 0.4 g (0.3 mmol) of tetrakistriphenylphosphinpalladium, 3.6 g (26 mmol) of potassium carbonate, 25 ml of 1,4-dioxane, 25 ml of toluene, and 10 ml of water, and the mixture was refluxed. After the reaction was terminated, water and hexane were added to the resultant mixture. Crystals produced therefrom were filtered. The crystals were recrystallized to obtain 5.3 g of Compound 68 (yield: 57%).

The produced compound was identified using NMR.

MS: m/z 969 [M]$^+$ $^1$H NMR (CDCl$_3$) δ 9.07 (d, 1H), 8.95 (m, 2H), 8.48 (d, 1H), 7.75 (m, 6H), 7.37 (m, 24H), 6.62 (s, 2H), 2.00 (m, 2H), 1.60 (m, 14H), 1.30 (s, 3H), 1.28 (s, 3H), 1.18 (s, 3H), 1.15 (s, 3H)

Example 1

ITO glass was patterned to have an emission area of 2 mm×2 mm and then washed. The ITO glass was placed in a vacuum chamber, CuPc was deposited on the ITO glass at a base pressure of 1×10$^{-7}$ torr to form a HIL having a thickness of 800 Å, and α-NPD was deposited on the HIL to form a HTL having a thickness of 300 Å. Compound BH01 and Compound 1 (3 wt %) were co-deposited on the HTL to form an EML having a thickness of 250 Å and Alq$_3$ was deposited on the EML to form an ETL having a thickness of 350 Å. Thereafter, a LiF EIL having a thickness of 5 Å was formed on the ETL and an Al electrode having a thickness of 500 Å was formed on the EIL, thereby completing the manufacturing of an OLED.

Examples 2 Through 8

OLEDs were manufactured in the same manner as in Example 1, except that Compounds 3, 9, 10, 11, 12, 28, and 29 were respectively used instead of Compound 1.

Comparative Example 1

An OLED was manufactured in the same manner as in Example 1, except that Compound A below was used instead of Compound 1.

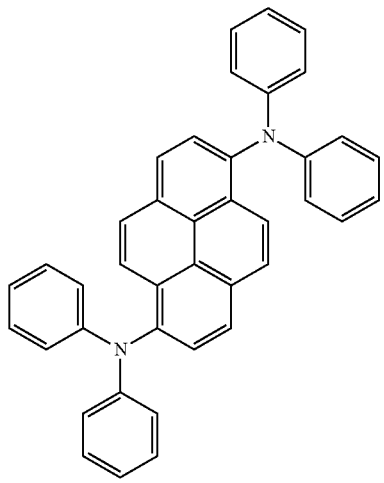

Compound A

Comparative Example 2

An OLED was manufactured in the same manner as in Example 1, except that Compound B below was used instead of Compound 1.

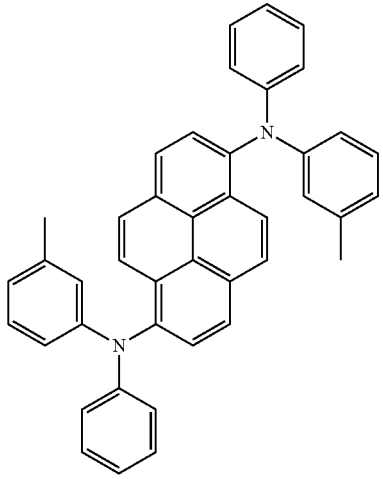

Compound B

Evaluation Example 1

Figure 2:
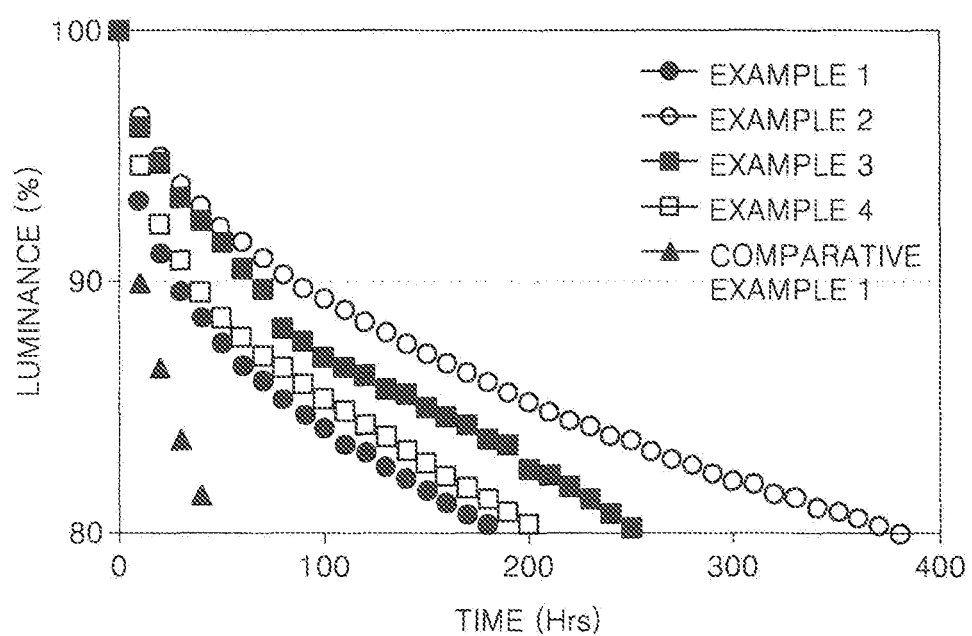
FIG. 2 is a graph showing lifetime characteristics of OLEDs manufactured according to Examples 1 through 4 and Comparative Example 1 according to an embodiment of the present invention.
Figure 3:
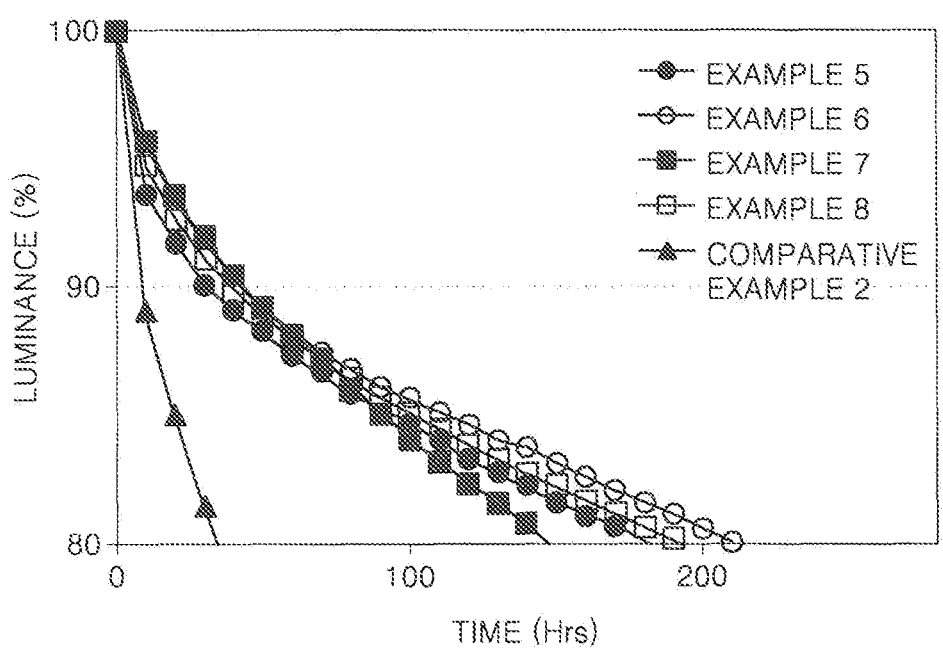
FIG. 3 is a graph showing lifetime characteristics of OLEDs manufactured according to Examples 5 through 8 and Comparative Example 2 according to an embodiment of the present invention.
Figure 4:
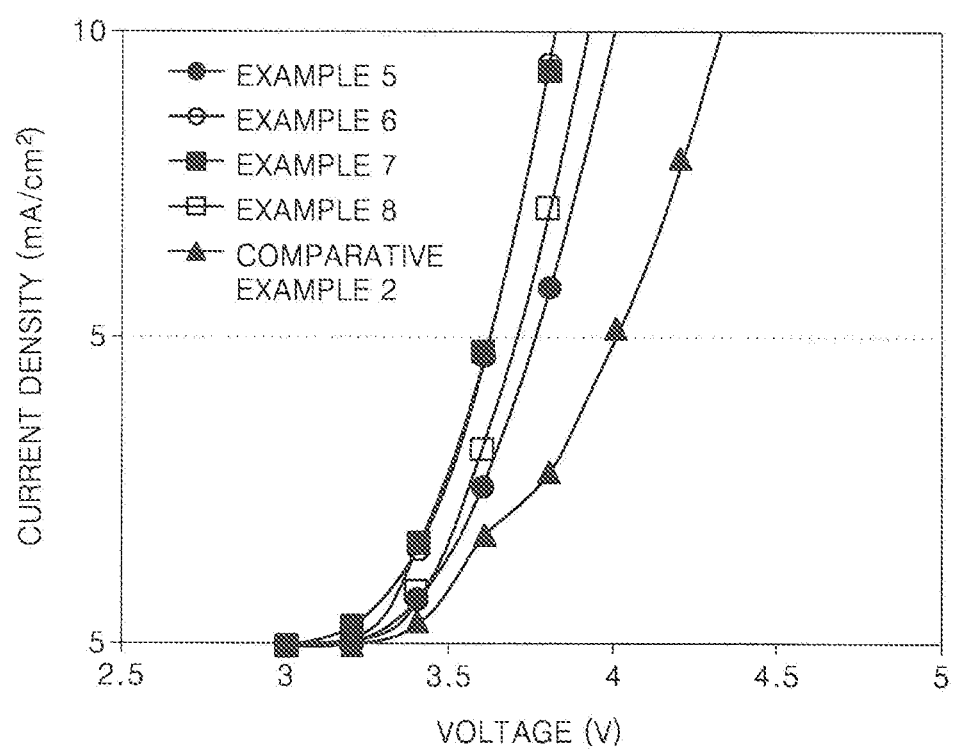
FIG. 4 is a graph showing changes in current density versus voltage characteristics of OLEDs of Examples 5 through 8 and Comparative Example 2 according to an embodiment of the present invention.
Figure 5:
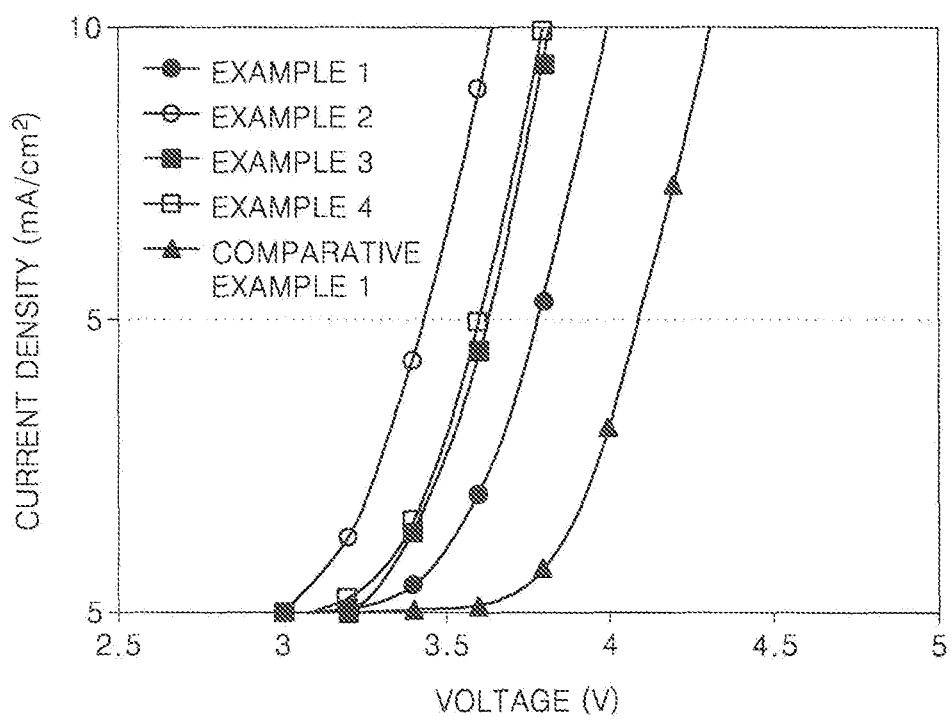
FIG. 5 is a graph showing changes in current density versus voltage characteristics of OLEDs of Examples 1 through 4 and Comparative Example 1 according to an embodiment of the present invention.

Driving voltage, current, luminance (measured at 0.4 mA), color coordinate, and lifetime (T80) of each of the OLEDs manufactured according to Examples 1 through 8 and Comparative Examples 1 and 2 were measured using PR650 Spectroscan Source Measurement Unit (manufactured by PhotoResearch), and the measurement results are shown in Table 1 below. In addition, lifetime data of the OLEDs are illustrated in FIGS. 2 and 3 and current density date of the OLEDs are illustrated in FIGS. 4 and 5. T80 indicates the time at which the luminance of each of the OLEDs is decreased to 80% of the initial luminance and it was measured at 3,000 nit.

TABLE 1

| | dopant | Vol. (V) | Current density (mA/cm$^2$) | External quantum efficiency | Luminance (cd/m$^2$) | CIEx | CIEy | T80 (hr) |
|---|---|---|---|---|---|---|---|---|
| Example 1 | 1 | 4.0 | 10 | 5.61 | 471 | 0.145 | 0.096 | 187 |
| Example 2 | 3 | 3.6 | 10 | 6.83 | 690 | 0.142 | 0.123 | 379 |
| Example 3 | 9 | 3.8 | 10 | 6.09 | 695 | 0.141 | 0.148 | 257 |
| Example 4 | 10 | 3.8 | 10 | 6.33 | 624 | 0.143 | 0.120 | 207 |
| Example 5 | 11 | 4.0 | 10 | 6.71 | 677 | 0.142 | 0.125 | 180 |
| Example 6 | 12 | 3.8 | 10 | 6.16 | 693 | 0.141 | 0.145 | 211 |
| Example 7 | 28 | 3.8 | 10 | 5.43 | 480 | 0.145 | 0.103 | 150 |
| Example 8 | 29 | 3.9 | 10 | 6.46 | 663 | 0.141 | 0.127 | 194 |
| Comparative Example 1 | A | 4.3 | 10 | 5.06 | 534 | 0.133 | 0.137 | 45 |
| Comparative Example 2 | B | 4.3 | 10 | 4.59 | 504 | 0.134 | 0.144 | 35 |

From the results as shown in Table 1 and FIGS. 2 through 5, it is confirmed that each of the OLEDs of Examples 1 through 8 has excellent driving voltage and external quantum efficiency, higher luminance, higher color purity, and longer lifetime, as compared to the OLEDs of Comparative Examples 1 and 2.

As described above, the condensed-cyclic compound of Formula 1 may have high thermal resistance and excellent luminous properties, and thus an OLED including the condensed-cyclic compound of Formula 1 may have excellent driving voltage, high efficiency, high luminance, excellent external quantum efficiency, and long lifetime.

Synthesis Example 21

Synthesis of Compound 2A

Synthesis Example 21-(1)

Synthesis of [Intermediate 2A-a]

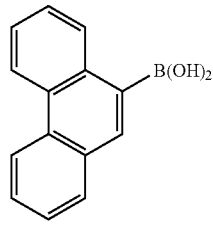

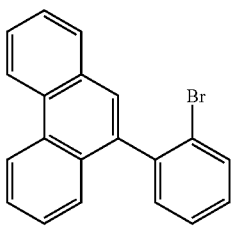

[Intermediate 2A-a]

1-bromo-2-iodobenzene (31.7 g, 112 mmol), 9-phenanthrilboronic acid (34.6 g, 156 mmol), tetrakistriphenylphosphinepalladium (2.6 g, 2 mmol), potassium carbonate (30.9 g, 223 mmol), 50 mL of water, 125 mL of toluene, and 125 mL of tetrahydrofurane were loaded into a round-bottom flask, and then, the mixture was refluxed for 12 hours. Once an organic layer was concentrated under reduced pressure, the resultant was subjected to column chromatography to obtain 26.9 g (yield of 72%) of [Intermediate 2A-a].

Synthesis Example 21-(2)

Synthesis of [Intermediate 2A-b]

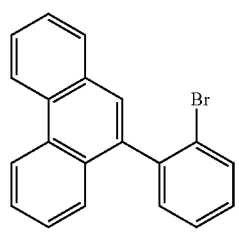

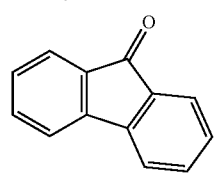

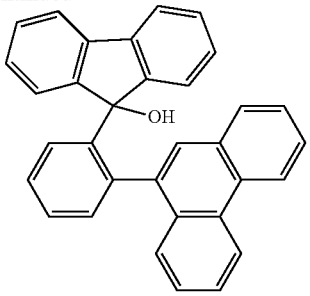

[Intermediate 2A-b]

[Intermediate 2A-a] (4.1 g, 12.2 mmol) was added to 50 mL of tetrahydrofurane, and then, at a temperature of −78° C., n-butyllithium (5.8 mL, 14.6 mmol) was added dropwise thereto. The resultant was stirred for about 1 hour. Then, at the same temperature, 9-fluorenone (1.9 g, 10.8 mmol) dissolved in 10 mL of tetrahydrofurane was slowly added dropwise thereto and the resultant was stirred for 2 hours, and then, stirred for 12 hours at room temperature. After extraction using ethyl acetate, the resultant was recrystallized by using diethylether to obtain 4.2 g (yield of 79%) of [Intermediate 2A-b].

Synthesis Example 21-(3)

Synthesis of [Intermediate 2A-c]

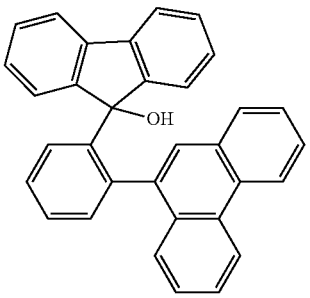

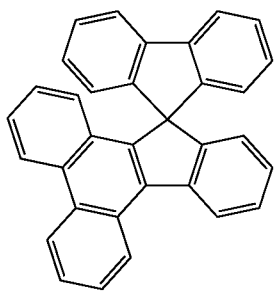

[Intermediate 2A-c]

[Intermediate 2A-b] (28.8 g, 66.3 mmol) was added to 300 mL of an acetic acid, and then, the temperature was raised to 80° C. and one or two drops of an HCl aqueous solution were added thereto, followed by two hours of refluxing. The temperature was dropped to room temperature, and the resultant was filtered to obtain 25.4 g (yield of 92%) of [Intermediate 2A-c].

Synthesis Example 21-(4)

Synthesis of [Intermediate 2A-d]

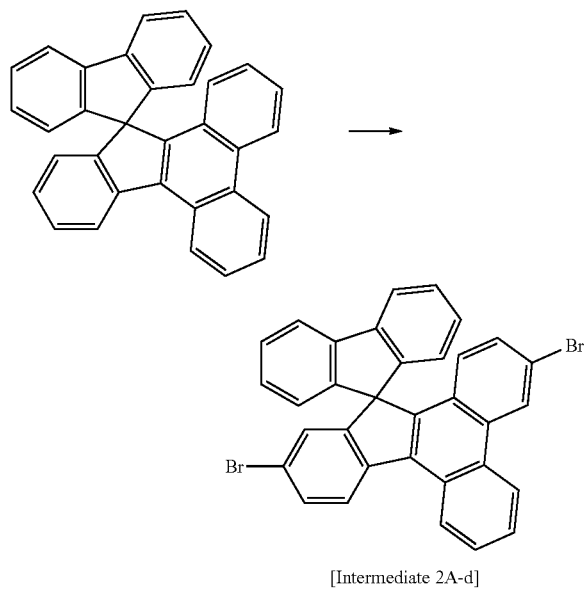

[Intermediate 2A-d]

[Intermediate 2A-c] (22.9 g, 0.055 mol) was added to 250 mL of dimethylformamide, and the resultant was stirred at a temperature of 0° C. n-bromosuccinimide (21.5 g, 0.121 mol) dissolved in 70 mL of dimethylformamide was added dropwise thereto, and the resultant was stirred for 12 hours. The reaction product was filtered by using distilled water and washed with hexane. Then, the resultant was dissolved in dichloromethane and heated, and then, subjected to an active charcoal treatment with acid white clay. Then, the resultant was washed with dichloromethane and re-crystallized by using hexane, thereby obtaining 23.7 g (yield of 75%) of [Intermediate 2A-d].

Synthesis Example 21-(5)

Synthesis of [Intermediate 2A-e]

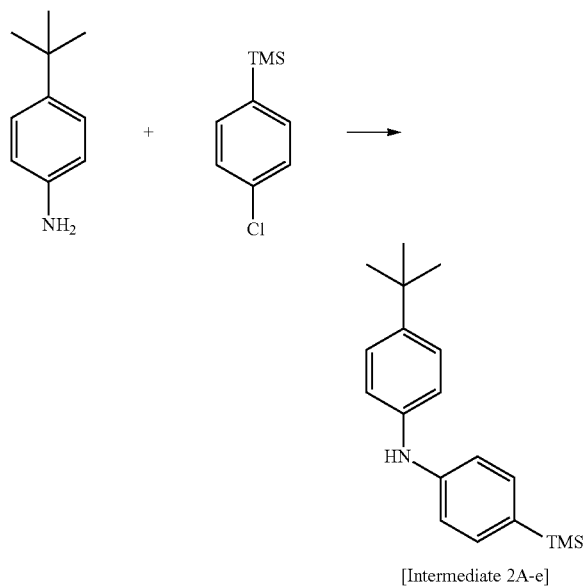

[Intermediate 2A-e]

(4-chlorophenyl)trimethylsilane (18.5 g, 0.1 mol), 4-amino-tertiarybutylbenzene (14.9 g, 0.1 mol), palladium acetate (0.08 g, 0.32 mmol), 2,2'-bis(diphenylphosphino)-1-1'-binaphthyl (0.26 g, 0.42 mmol), and sodium tertiarybutoxide (15.2 g, 0.16 mol) were added to 150 mL of toluene, and the mixture was refluxed for 12 hours. The resultant was cooled to room temperature, and then, washed by using methanol and re-crystallized by using dichloromethane and methanol, thereby obtaining 22.3 g (yield of 75%) of [Intermediate 2A-e].

Synthesis Example 21-(6)

Synthesis of [Compound 2A]

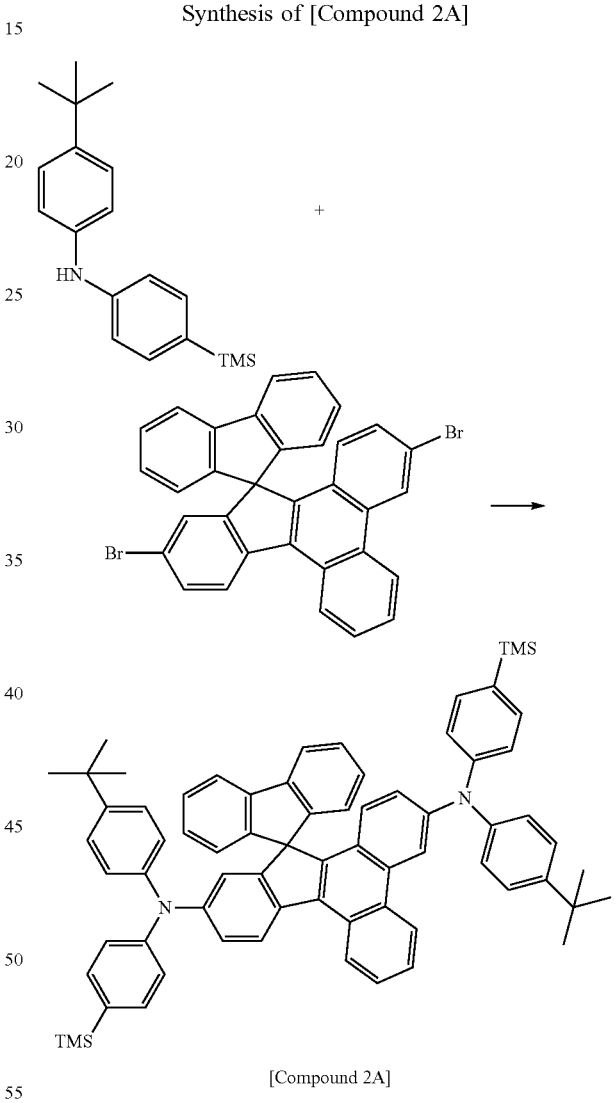

[Compound 2A]

[Intermediate 2A-d] (5.5 g, 9.5 mmol), [Intermediate 1-e] (7.4 g, 24.8 mmol), and palladium acetate (0.15 g, 0.67 mmol) were added to 80 mL of toluene, and the mixture was stirred at a temperature of 60° C. Tritertiarybutylphosphine (0.42 g, 1.9 mmol) and potassium tertiary butoxide (4.2 g, 38.1 mmol) were slowly added dropwise thereto, and then, reacted at a temperature of 100° C. for 2 hours. The reaction product was subjected to an extraction process using dichloromethane, followed by column chromatography, thereby obtaining 4.1 g (yield of 43%) of [Compound 2A].
MS (MALDI-TOF): m/z 1006.51 [M]$^+$

Synthesis Example 22

Synthesis of Compound 6A

Synthesis Example 22-(1)

Synthesis of Intermediate 6A-a

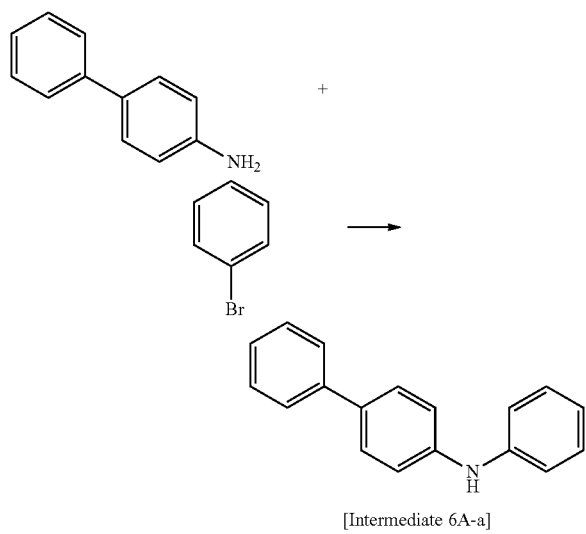

[Intermediate 6A-a]

4-amino biphenyl (16.3 g, 96 mmol), bromobenzene (15.8 g, 101 mmol), palladium acetate (0.32 g, 1.4 mmol), 2,2-bis diphenylphosphino-1,1'-binaphthyl (0.9 g, 1.4 mmol), sodium tertiary butoxide (18.5 g, 193 mmol), and 160 ml of toluene were added to a round-bottom flask, and then, the mixture was refluxed for 24 hours. The temperature was adjusted to be room temperature, and then, the resultant was filtered and the obtained filtrate was concentrated and purified by column chromatography. Thereafter, the resultant was re-crystallized by using dichloromethane and methanol, and filtered and dried, thereby producing 15 g (yield of 60%) of [Intermediate 6A-a], which was in the form of white solid.

Synthesis Example 22-(2)

Synthesis of [Compound 6A]

[Compound 6A] (yield of 45%) was obtained in the same manner as in Synthesis Example 21-(6), except that [Intermediate 6A-a] was used instead of [Intermediate 2A-e]

MS (MALDI-TOF): m/z 902.37 $[M]^+$.

Synthesis Example 23

Synthesis of Compound 8A

[Compound 8A] (yield of 47%) was obtained in the same manner as in Synthesis Example 21-(5), except that penta-deuterated iodobenzene was used instead of (4-chlorophenyl)trimethylsilane.

MS (MALDI-TOF): m/z 872.49 $[M]^+$

Synthesis Example 24

Synthesis of Compound 18A

[Compound 18A] (yield of 44%) was obtained in the same manner as in Synthesis Example 21, except that, in Synthesis Example 21-(5), 1-cyano-4-chlorobenzene was used instead of (4-chlorophenyl)trimethylsilane, and 2-methyl-5-aminopyridine was used instead of 4-amino-tertiarybutylbenzene.

MS (MALDI-TOF): m/z 830.32 $[M]^+$

Example 21

ITO glass was patterned such that an emission area thereof was a size of 2 mm×2 mm, and then, washed. The ITO glass was mounted on a vacuum chamber, and then, a base pressure was adjusted to be $1 \times 10^{-7}$ torr. Then, CuPc was deposited on the ITO glass to form a hole injection layer having a thickness of 800 Å, and α-NPD was deposited on the hole injection layer to form a hole transport layer having a thickness of 300 Å. Compound BH1 and Compound 2A (3 wt. %) were co-deposited on the hole transport layer to form an emission layer having a thickness of 250 Å, and then, $Alq_3$ was deposited on the emission layer to form an electron transport layer having a thickness of 350 Å. Subsequently, LiF electron injection layer having a thickness of 5 Å and Al electrode having a thickness of 500 Å were sequentially formed thereon, thereby completing the manufacture of an organic light-emitting diode.

Examples 22 to 24

Organic light-emitting diodes were manufactured in the same manner as in Example 21, except that Compounds 6A, 8A, and 18A were used instead of Compound 2A.

Evaluation Example 2

Driving voltage, current, luminance (measured at 0.4 mA), color coordinate, and lifetime (T80) of the organic light-emitting diodes manufactured according to Examples 21 to 24 and Comparative Examples 1 and 2 were measured by using PR650 Spectroscan Source Measurement Unit. (a product of PhotoResearch Company), and results thereof are shown in Table 2. T80 indicates a period of time that has elapsed when luminance reduces to 80% of the initial luminance, and herein, was measured at 3,000 nit.

TABLE 2

| | Dopant | Voltage (V) | Current density (mA/cm$^2$) | External quantum efficiency | Luminance (cd/m$^2$) | CIEx | CIEy | T80 (hr) |
|---|---|---|---|---|---|---|---|---|
| Example 21 | 2A | 3.6 | 10 | 7.67 | 645 | 0.142 | 0.112 | 412 |
| Example 22 | 6A | 3.6 | 10 | 7.12 | 674 | 0.142 | 0.120 | 397 |
| Example 23 | 8A | 3.7 | 10 | 6.99 | 661 | 0.141 | 0.118 | 378 |
| Example 24 | 18A | 3.7 | 10 | 6.56 | 624 | 0.141 | 0.121 | 325 |
| Comparative Example 1 | A | 4.3 | 10 | 5.06 | 534 | 0.133 | 0.137 | 45 |

TABLE 2-continued

| | Dopant | Voltage (V) | Current density (mA/cm$^2$) | External quantum efficiency | Luminance (cd/m$^2$) | CIEx | CIEy | T80 (hr) |
|---|---|---|---|---|---|---|---|---|
| Comparative Example 2 | B | 4.3 | 10 | 4.59 | 504 | 0.134 | 0.144 | 35 |

From the results as shown in Table 2, it is confirmed that each of the OLEDs of Examples 21 through 24 has excellent driving voltage and external quantum efficiency, higher luminance, higher color purity, and longer lifetime, as compared to the OLEDs of Comparative Examples 1 and 2.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A condensed-cyclic compound represented by Formula 1A below:

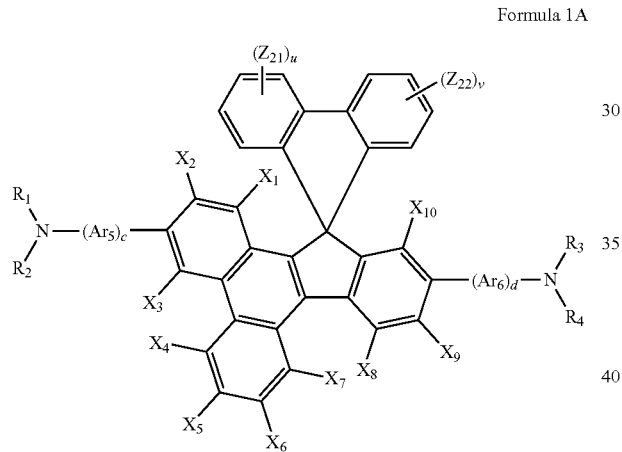

Formula 1A wherein $R_1$ is represented by $—(Ar_1)_{a1}—(R_{11})_{b1}$, $R_2$ is represented by $—(Ar_2)_{a2}—(R_{12})_{b2}$, $R_3$ is represented by $—(Ar_3)_{a3}—(R_{13})_{b3}$, and $R_4$ is represented by $—(Ar_4)_{a4}—(R_{14})_{b4}$;

$Ar_1$ through $Ar_4$ are each independently a substituted or unsubstituted $C_6$-$C_{60}$ aromatic linking group or a substituted or unsubstituted $C_2$-$C_{60}$ heteroaromatic linking group;

$Ar_5$ and $Ar_6$ are each independently a substituted or unsubstituted $C_6$-$C_{60}$ arylene group or a substituted or unsubstituted $C_2$-$C_{60}$ heteroarylene group;

$R_{11}$ through $R_{14}$ are each independently non-covalent electron pairs, hydrogen, deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, or a substituted or unsubstituted $C_2$-$C_{60}$ condensed-cyclic group;

a1 through a4 are each independently an integer of 0 to 3;
b1 through b4 are each independently an integer of 1 to 5;
c and d are each independently an integer of 0 to 3;
$X_1$ through $X_{10}$ are each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, $—Si(R_{21})(R_{22})(R_{23})$, or $—N(R_{24})(R_{25})$;

$R_{21}$ through $R_{25}$ are each independently hydrogen, deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group;

$Z_{21}$ and $Z_{22}$ are each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, or a substituted or unsubstituted $C_1$-$C_{60}$ alkoxy group;

u is an integer of 1 to 4; and
v is an integer of 1 to 6.

2. The condensed-cyclic compound of claim 1, wherein $R_{11}$ through $R_{14}$ are each independently hydrogen, deuterium, a substituted or unsubstituted $C_1$-$C_{10}$ alkyl group, a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted cyclopentyl group, a substituted or unsubstituted cyclohexyl group, a substituted or unsubstituted cycloheptyl group, a substituted or unsubstituted dihydronaphthyl group, a substituted or unsubstituted tetrahydronaphthyl group, or a substituted or unsubstituted dihydro-indenyl group.

3. The condensed-cyclic compound of claim 1, wherein $Ar_1$ through $Ar_4$ are each independently a substituted or unsubstituted benzene linking group, a substituted or unsubstituted pentalene linking group, a substituted or unsubstituted indene linking group, a substituted or unsubstituted naphthalene linking group, a substituted or unsubstituted azulene linking group, a substituted or unsubstituted heptalene linking group, a substituted or unsubstituted indacene linking group, a substituted or unsubstituted acenaphthylene linking group, a substituted or unsubstituted fluorene linking group, a substituted or unsubstituted phenalene linking group, a substituted or unsubstituted phenanthrene linking group, a substituted or unsubstituted anthracene linking group, a substituted or unsubstituted fluoranthene linking group, a substituted or unsubstituted triphenylene linking group, a substituted or unsubstituted pyrene linking group, a substituted or unsubstituted crycene linking group, a substituted or unsubstituted naphthacene linking group, a substituted or unsubstituted pycene linking group, a substituted or unsubstituted perylene linking group, a substituted or unsubstituted pentacene linking group, or a substituted or unsubstituted hexacene linking group.

4. The condensed-cyclic compound of claim 1, wherein $a_1$ through $a_4$ are each independently 0, 1, or 2, and $b_1$ through $b_4$ are each independently 1 or 2.

5. The condensed-cyclic compound of claim 1, wherein $R_{11}$ through $R_{14}$ are each independently one of hydrogen; deuterium; a $C_1$-$C_{10}$ alkyl group; a phenyl group; a naphthyl group; a phenanthrenyl group; a fluorenyl group; a pyrenyl group; a cyclopentyl group; a cyclohexyl group; a tetrahydronaphthyl group; a dihydro-indenyl group; and a phenyl group, a naphthyl group, a phenanthrenyl group, a fluorenyl group, a pyrenyl group, a cyclopentyl group, a cyclohexyl group, a tetrahydronaphthyl group, and a dihydro-indenyl group that are substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, and —Si($Q_1$)($Q_2$)($Q_3$);

$Q_1$ through $Q_3$ are each independently a $C_1$-$C_{10}$ alkyl group or a $C_6$-$C_{14}$ aryl group;

$Ar_1$ through $Ar_4$ are each independently represented by one of Formulae 3A through 3G below:

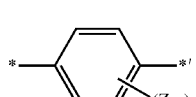

Formula 3A

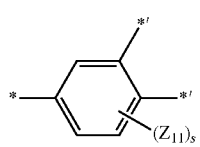

Formula 3B

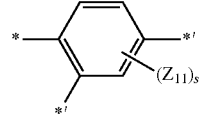

Formula 3C

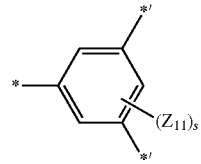

Formula 3D

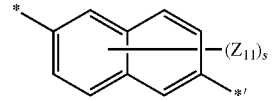

Formula 3E

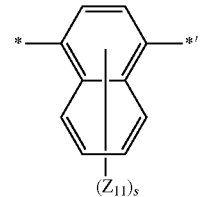

Formula 3F

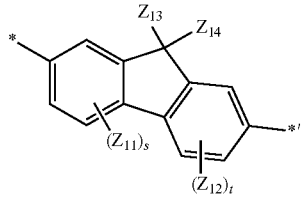

Formula 3G wherein $Z_{11}$ through $Z_{14}$ are each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

s is an integer of 1 to 6; and t is an integer of 1 to 3.

6. The condensed-cyclic compound of claim 1, wherein at least one of a combination of $R_1$ and $R_2$ and a combination of $R_3$ and $R_4$ in Formula 1 is linked to each other.

7. The condensed-cyclic compound of claim 1, wherein at least one of —N($R_1$)($R_2$) and —N($R_3$)($R_4$) in Formula 1 is represented by one of Formulae 5A through 5F:

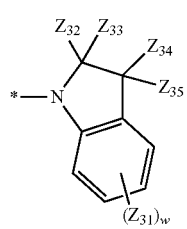

Formula 5A

-continued

Formula 5B

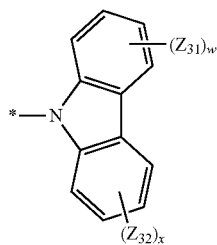

Formula 5C

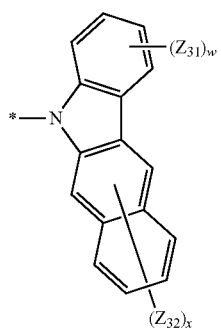

Formula 5D

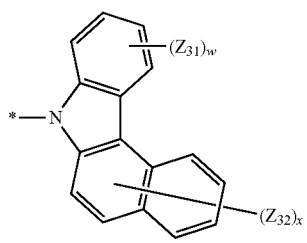

-continued

Formula 5E

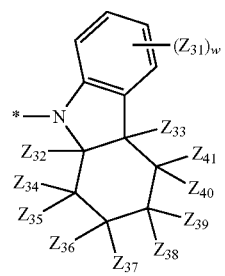

Formula 5F

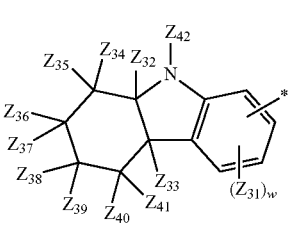

wherein $Z_{31}$ through $Z_{42}$ are each independently hydrogen, deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, or a substituted or unsubstituted $C_1$-$C_{60}$ alkoxy group, or a substituted or unsubstituted $C_6$-$C_{60}$ aryl group; and w and x are each independently an integer of 1 to 8.

8. The condensed-cyclic compound of claim 1, wherein the condensed-cyclic compound is one of Compounds 1A to 3A, 74 and 5A to 30A:

<Compound 1A>

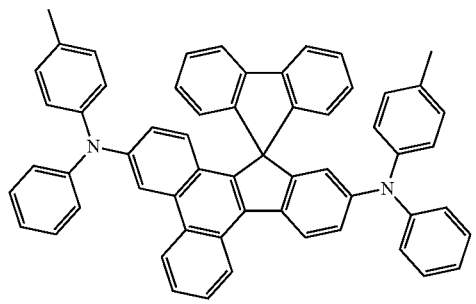

<Compound 2A>

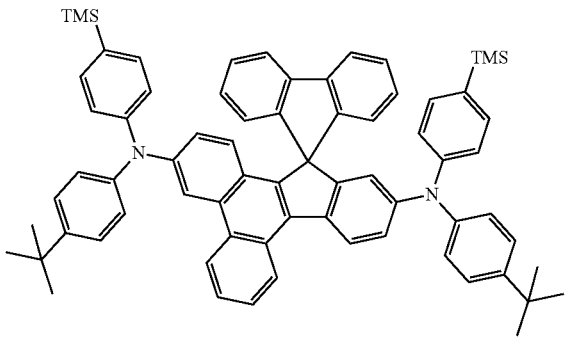

-continued
<Compound 3A>
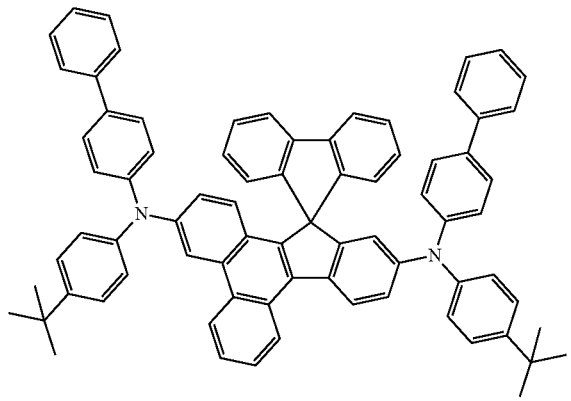
<Compound 74>
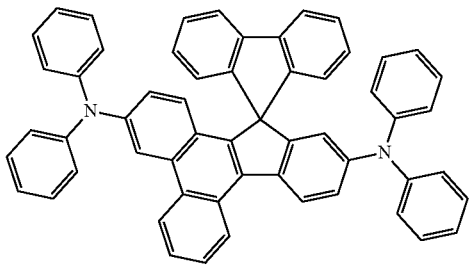
<Compound 5A>
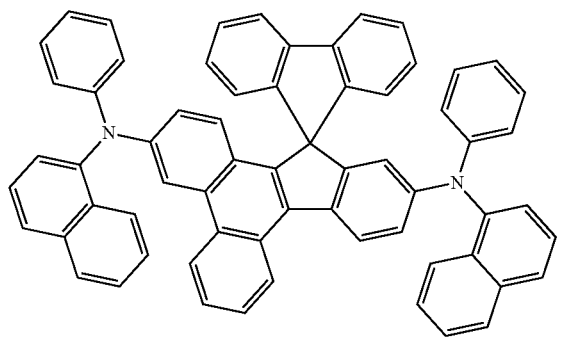
<Compound 6A>
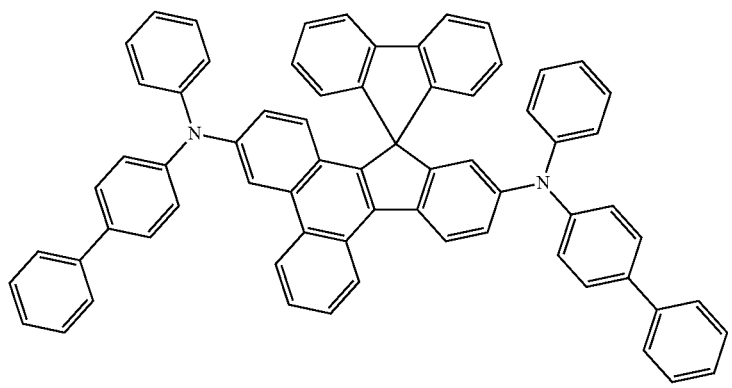
<Compound 7A>
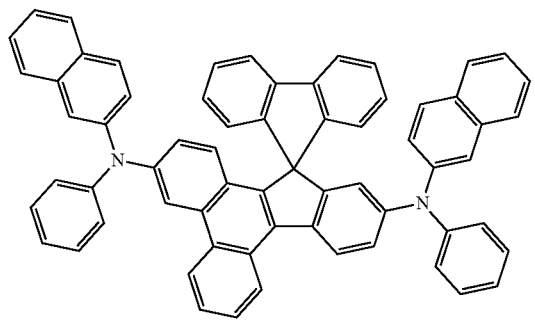
<Compound 8A>
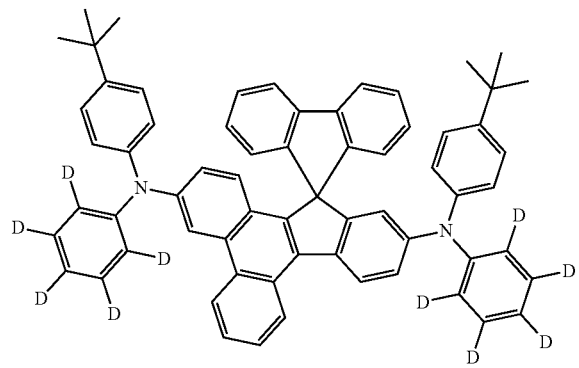

-continued
<Compound 9A>
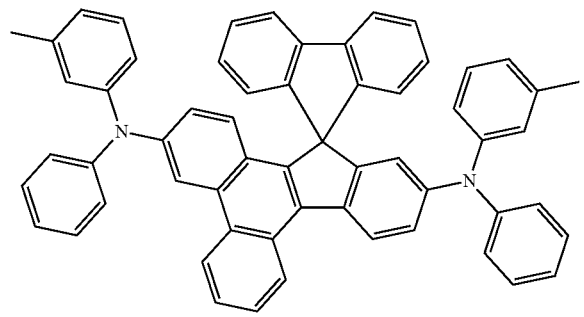
<Compound 10A>
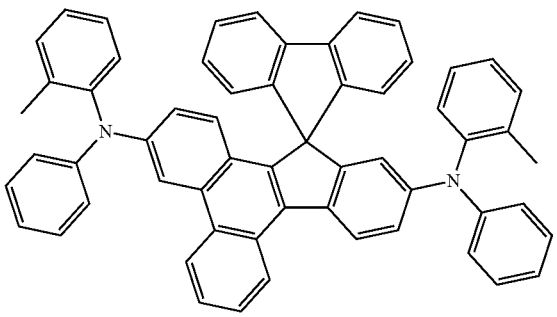
<Compound 11A>
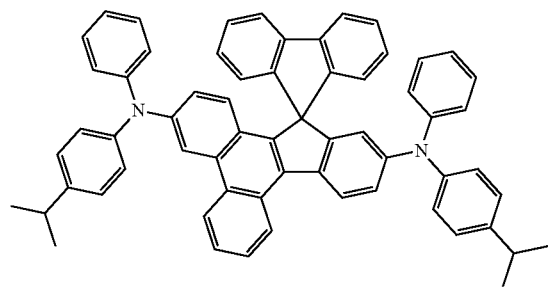
<Compound 12A>
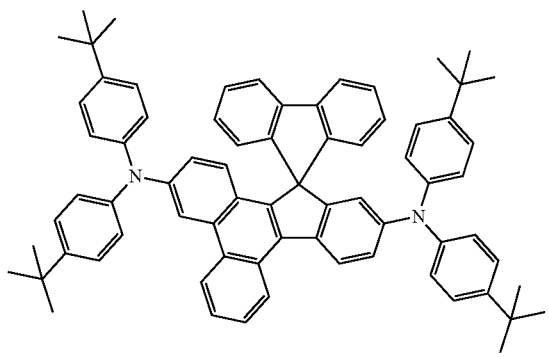
<Compound 13A>
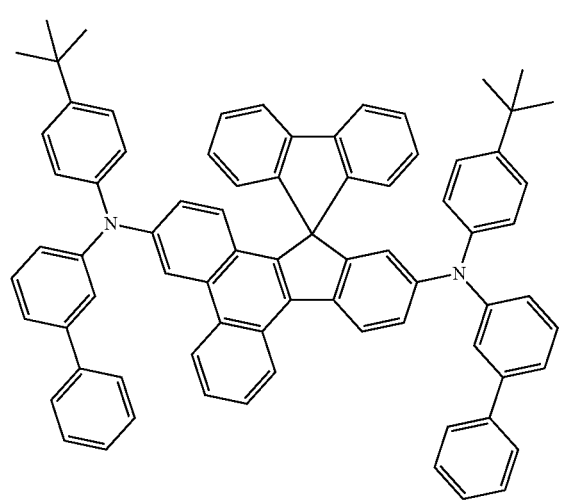

<Compound 14A>
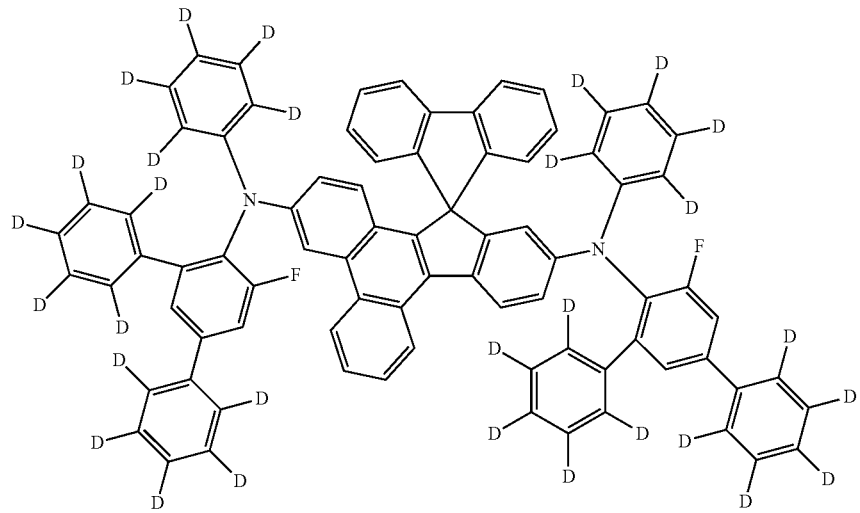
<Compound 15A>
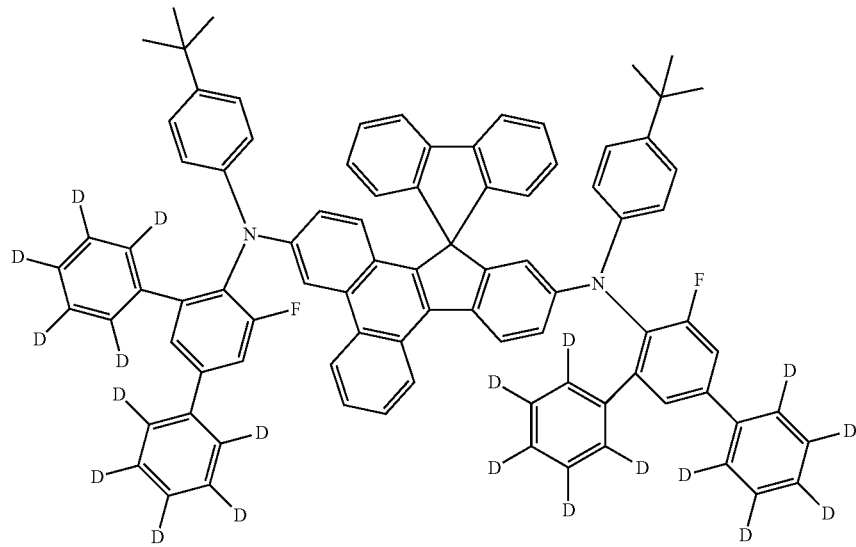
<Compound 16A>
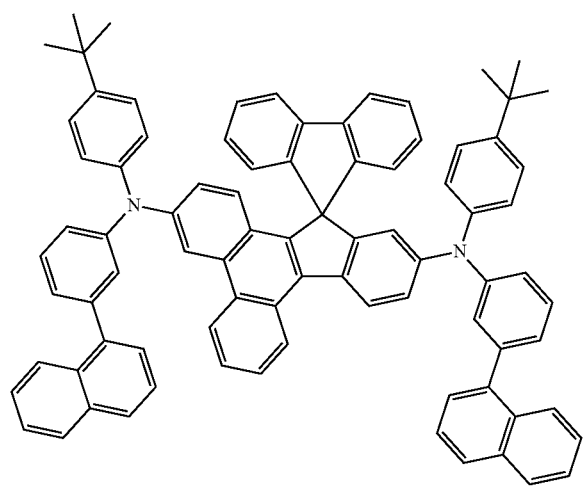
<Compound 17A>
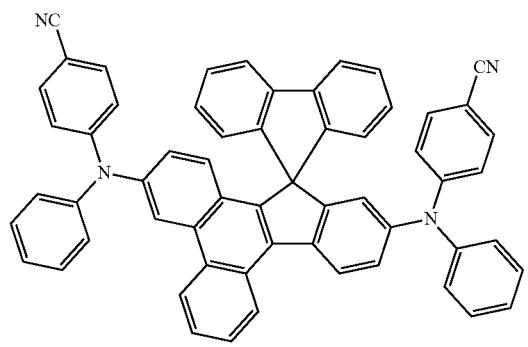

-continued
<Compound 18A>
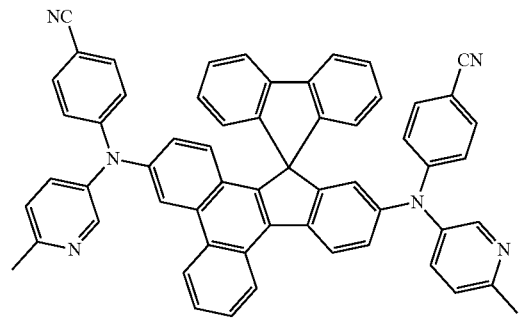
<Compound 19A>
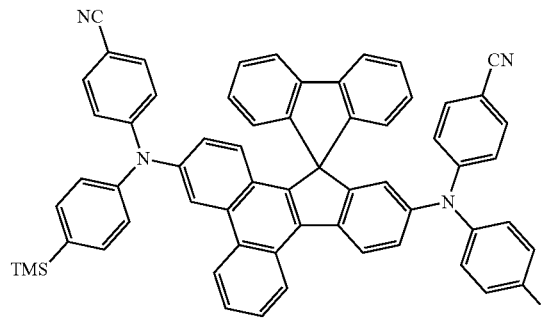
<Compound 20A>
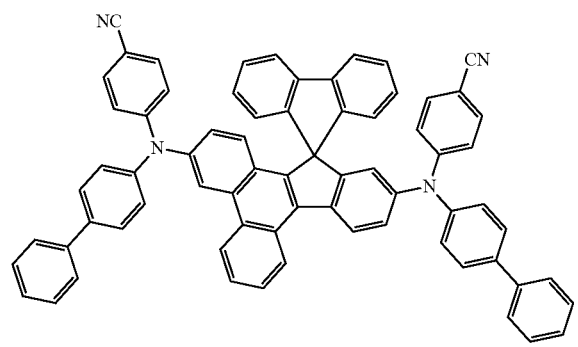
<Compound 21A>
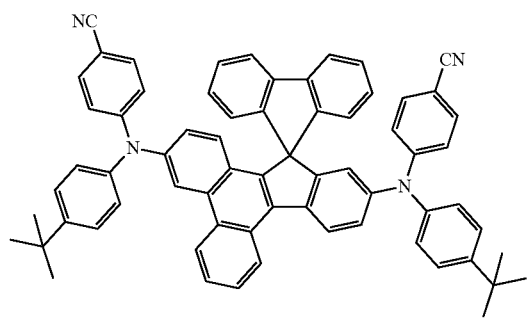
<Compound 22A>
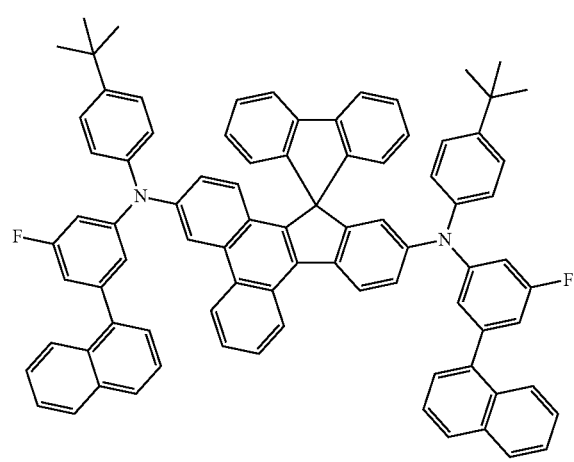
<Compound 23A>
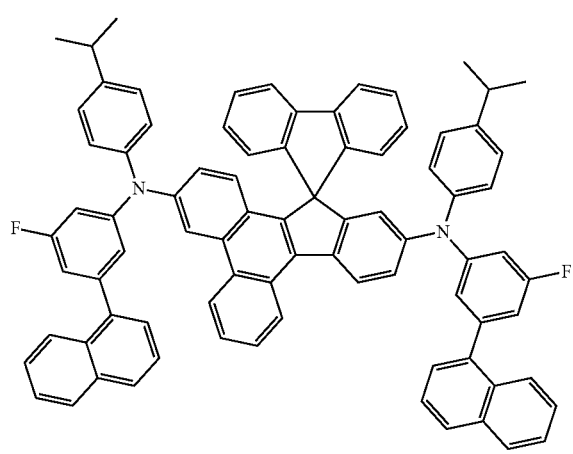
<Compound 24A>
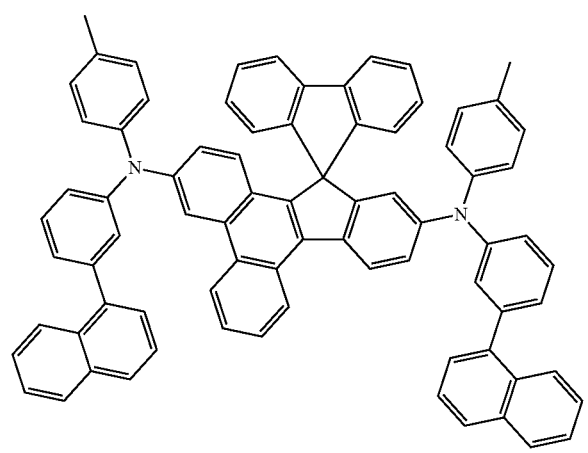
<Compound 25A>
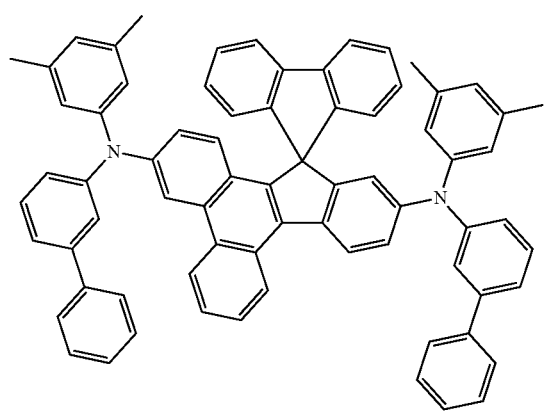

-continued

<Compound 26A>

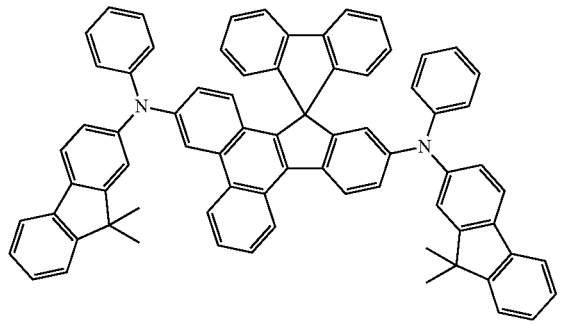

<Compound 27A>

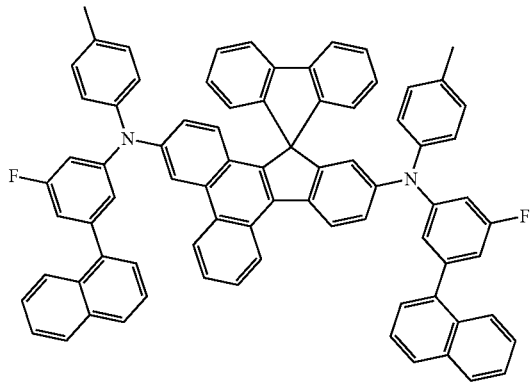

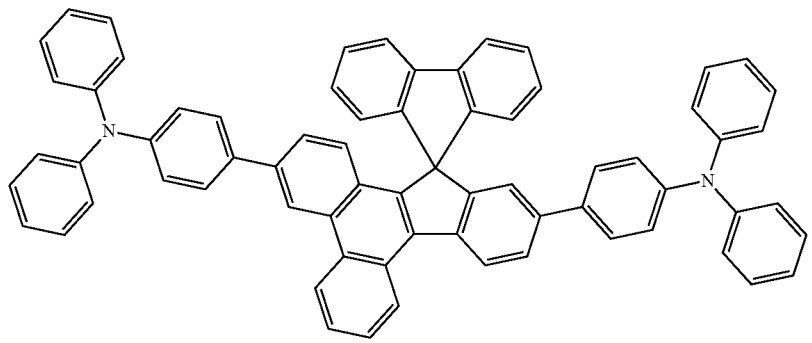

<Compound 29A>

<Compound 28A>

<Compound 30A>

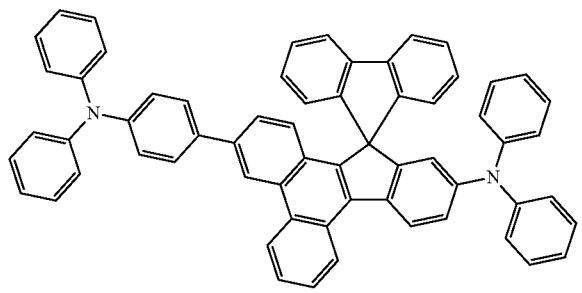

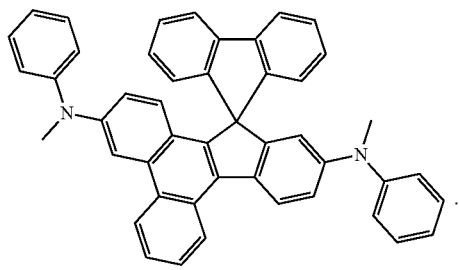

9. An organic light-emitting diode comprising:
a first electrode;
a second electrode facing the first electrode; and
an organic layer interposed between the first electrode and the second electrode; wherein the organic layer comprises at least one of the condensed-cyclic compound according to claim 1.

10. The organic light-emitting diode of claim 9, wherein the organic layer comprises a hole injection layer, a hole transport layer, a functional layer having hole injection and hole transport abilities, an emission layer, an electron transport layer, an electron injection layer, or any combination thereof.

11. The organic light-emitting diode of claim 10, wherein the emission layer comprises the condensed-cyclic compound.

12. The organic light-emitting diode of claim 11, wherein the emission layer further comprises a host and the condensed-cyclic compound in the emission layer acts as a dopant.

13. The organic light-emitting diode of claim 12, wherein the host comprises an anthracene-based compound represented by Formula 60 below:

Formula 60

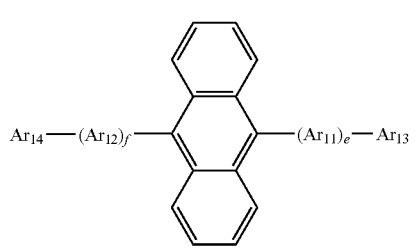

wherein $Ar_{11}$ and $Ar_{12}$ are each independently a substituted or unsubstituted $C_6$-$C_{60}$ arylene group;
$Ar_{13}$ and $Ar_{14}$ are each independently a substituted or unsubstituted $C_1$-$C_{10}$ alkyl group or a substituted or unsubstituted $C_6$-$C_{60}$ aryl group; and
e and f are each independently an integer of 0 to 5.

14. The organic light-emitting diode of claim 10, wherein the electron transport layer comprises an electron transport organic compound and a metal-containing material.

15. The organic light-emitting diode of claim 14, wherein the metal-containing material is a lithium complex.

16. The organic light-emitting diode of claim 10, wherein the organic layer comprises a hole injection layer, a hole transport layer, a functional layer having hole injection and hole transport abilities, or any combination thereof, and at least one of the hole injection layer, the hole transport layer, and the functional layer having hole injection and hole transport abilities comprises a charge-generating material.

* * * * *